(12) United States Patent
Metcalfe et al.

(10) Patent No.: US 12,743,968 B2
(45) Date of Patent: Sep. 22, 2026

(54) FRACTURE MODELS, SYSTEMS AND ASSOCIATED METHODS

(71) Applicant: ARTHREX, INC., Naples, FL (US)

(72) Inventors: Nick Metcalfe, Bonita Springs, FL (US); David Knopf, Bonita Springs, FL (US); Michael Moreland, Fort Myers, FL (US); Scott William Doody, Bonita Springs, FL (US); Steven Jim DeLeon, Naples, FL (US); Benjamin David Bernarding, Allison Park, PA (US); Shervin F. Kazemi, Naples, FL (US); David Yang, Bedford, MA (US); Gage Weimer, Ruskin, FL (US)

(73) Assignee: ARTHREX, INC., Naples, FL (US)

( * ) Notice: Subject to any disclaimer, the term of this patent is extended or adjusted under 35 U.S.C. 154(b) by 315 days.

(21) Appl. No.: 18/415,794

(22) Filed: Jan. 18, 2024

(65) Prior Publication Data

US 2024/0242634 A1 Jul. 18, 2024

Related U.S. Application Data

(60) Provisional application No. 63/480,361, filed on Jan. 18, 2023.

(51) Int. Cl.

*G09B 23/34* (2006.01)
*A61B 34/00* (2016.01)
*A61B 34/10* (2016.01)

(52) U.S. Cl.

CPC .............. *G09B 23/34* (2013.01); *A61B 34/10* (2016.02); *A61B 34/25* (2016.02); *A61B 2034/105* (2016.02)

(58) Field of Classification Search

CPC ........ G09B 23/34; G09B 23/30; A61B 34/10; A61B 34/25; A61B 2034/105; A61B 17/8866

(Continued)

(56) References Cited

U.S. PATENT DOCUMENTS

| | | | | |
|---|---|---|---|---|
| 6,315,780 | B1 * | 11/2001 | Lalonde ............... | A61B 17/282 606/86 R |
| 6,471,519 | B1 | 10/2002 | Biermann et al. | |

(Continued)

FOREIGN PATENT DOCUMENTS

| | | |
|---|---|---|
| EP | 3536354 | 9/2019 |
| RU | 197305 | 4/2020 |

(Continued)

OTHER PUBLICATIONS

Neijhoft, J., Henrich, D., Mors, K., Marzi, I., Janko, M. (2022). Visualization of complicated fractures by 3D-printed models for teaching and surgery: hands-on transitional fractures of the ankle. European Journal of Trauma and Emergency Surgery. 2022. pp. 3923-3931. (Year: 2022).*

(Continued)

*Primary Examiner* — Peter S Vasat
*Assistant Examiner* — Stephen Alvesteffer
(74) *Attorney, Agent, or Firm* — Carlson, Gaskey & Olds, P.C.

(57) ABSTRACT

This disclosure relates to surgical systems, devices and methods for planning and implementing surgical procedures, including repair of fractures. The systems and methods disclosed herein may be utilized to establish physical models of anatomy.

20 Claims, 50 Drawing Sheets

(58) Field of Classification Search
USPC .................................................. 434/262–275
See application file for complete search history.

(56) References Cited

U.S. PATENT DOCUMENTS

| | | | | |
|---|---|---|---|---|
| 7,699,615 | B2 | 4/2010 | Sakezles | |
| 7,780,451 | B2 * | 8/2010 | Willobee | G09B 23/32 434/267 |
| 7,857,626 | B2 | 12/2010 | Toly | |
| 8,210,852 | B2 | 7/2012 | Miller et al. | |
| 8,425,234 | B2 | 4/2013 | Sakezles | |
| 8,568,148 | B2 | 10/2013 | Miller et al. | |
| 8,843,229 | B2 | 9/2014 | Vanasse et al. | |
| 9,741,263 | B2 | 8/2017 | Iannotti et al. | |
| 9,805,624 | B2 | 10/2017 | Reihsen et al. | |
| 10,553,130 | B2 | 2/2020 | Poniatowski et al. | |
| 10,588,752 | B2 | 3/2020 | Winslow et al. | |
| 10,973,535 | B2 | 4/2021 | Iannotti et al. | |
| 11,033,336 | B2 | 6/2021 | Bohl | |
| 11,403,966 | B2 | 8/2022 | Tatum et al. | |
| 11,443,654 | B2 | 9/2022 | Grant et al. | |
| 11,450,237 | B2 | 9/2022 | Grant et al. | |
| 11,850,002 | B2 | 12/2023 | Walach et al. | |
| 2013/0085590 | A1 | 4/2013 | Bryan et al. | |
| 2014/0272881 | A1 | 9/2014 | Barsoum | |
| 2017/0249440 | A1 | 8/2017 | Lang et al. | |
| 2017/0296205 | A1 | 10/2017 | Iannotti et al. | |
| 2018/0005548 | A1 * | 1/2018 | Blair-Pattison | G09B 23/34 |
| 2019/0142520 | A1 | 5/2019 | VanDyken | |
| 2019/0220974 | A1 | 7/2019 | Mathaneswaran et al. | |
| 2019/0239973 | A9 | 8/2019 | Esterberg et al. | |
| 2020/0015893 | A1 | 1/2020 | Walach | |
| 2021/0012681 | A1 | 1/2021 | Holz et al. | |
| 2021/0196290 | A1 | 7/2021 | Iannotti et al. | |
| 2021/0233429 | A1 | 7/2021 | Barber et al. | |
| 2021/0241656 | A1 | 8/2021 | Barber et al. | |
| 2021/0244474 | A1 | 8/2021 | Barber et al. | |
| 2021/0280087 | A1 | 9/2021 | Logan | |
| 2022/0270517 | A1 | 8/2022 | Fink et al. | |

FOREIGN PATENT DOCUMENTS

| | | | |
|---|---|---|---|
| RU | 197305 U1 * | 4/2020 | A61B 17/80 |
| WO | 2006034018 | 3/2006 | |
| WO | 2015089118 | 6/2015 | |
| WO | 2019158470 | 8/2019 | |
| WO | 2020123706 | 6/2020 | |
| WO | 2020163358 | 8/2020 | |
| WO | 2020231654 | 11/2020 | |
| WO | 2021127410 | 6/2021 | |
| WO | 2021237367 | 12/2021 | |
| WO | 2022152681 | 7/2022 | |

OTHER PUBLICATIONS

International Search Report & Written Opinion for International Application No. PCT/US2024/011930 mailed Apr. 24, 2024.

Neijhoft, J., Henrich, D., Mors, K., Marzi, I., Janko, M. (2022). Visualization of complicated fractures by 3D-printed models for teaching and surgery: hands-on transitional fractures of the ankle. European Journal of Trauma and Emergency Surgery. 2022. pp. 3923-31.

Paramasivam, V., Sindhu, Singh, G., Santhanakrishnan, S. (2020). 3D printing of human anatomical models for preoperative surgical planning. ScienceDirect. Procedia Manufacturing 48. pp. 684-690.

International Search Report and Written Opinion for International Application No. PCT/US2022/046041 filed Nov. 25, 2022.

Product Brochure. AO/OTA Fracture and Dislocation Classification. 2018. Retrieved from: https://www.aofoundation.org/trauma/clinical-library-and-tools/journals-and-publications/classification.

Kellam, JF, Meinberg, EG, Agel, J., Karam, MD, Roberts, CS. (2018). Fracture and dislocation classification compendium—2018. J Ortho Trauma. vol. 32(1). Supplement. Jan. 2018.

Marmor, MT, Agel, J, Dumpe, J, Kellam, JF, Marecek, GS, Meinberg, E, Nguyen, MP, Sims, S, Soles, Gl, Karam, MD. (2021). Comparison of the Neer classification to the 2018 update of the Orthopedic Trauma Association/AO fracture classification for classifying proximal humerus fractures. OTAI 2022. pp. 1-7.

International Prelminary Report on Patentability for International Application No. PCT/US2024/011930 mailed Jul. 31, 2025.

* cited by examiner

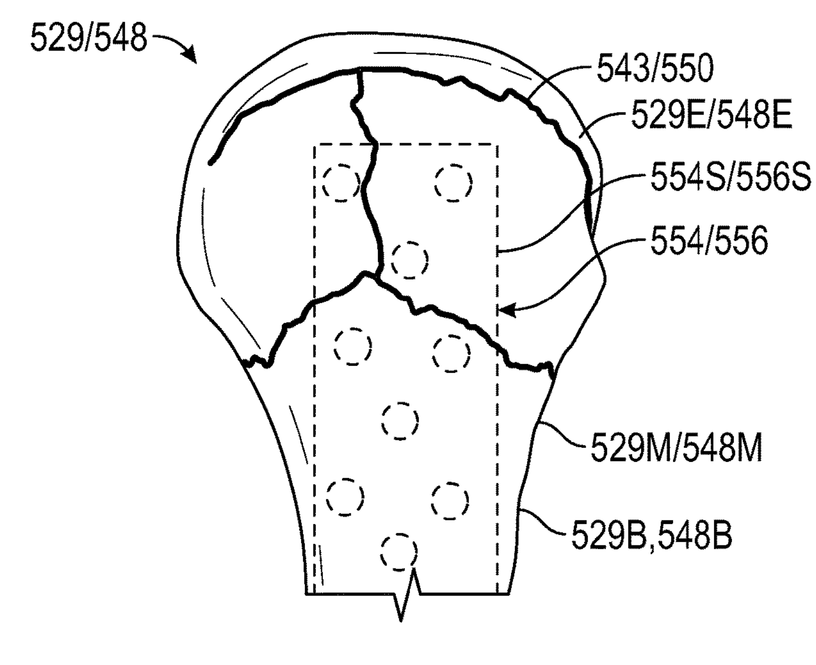
FIG. 22
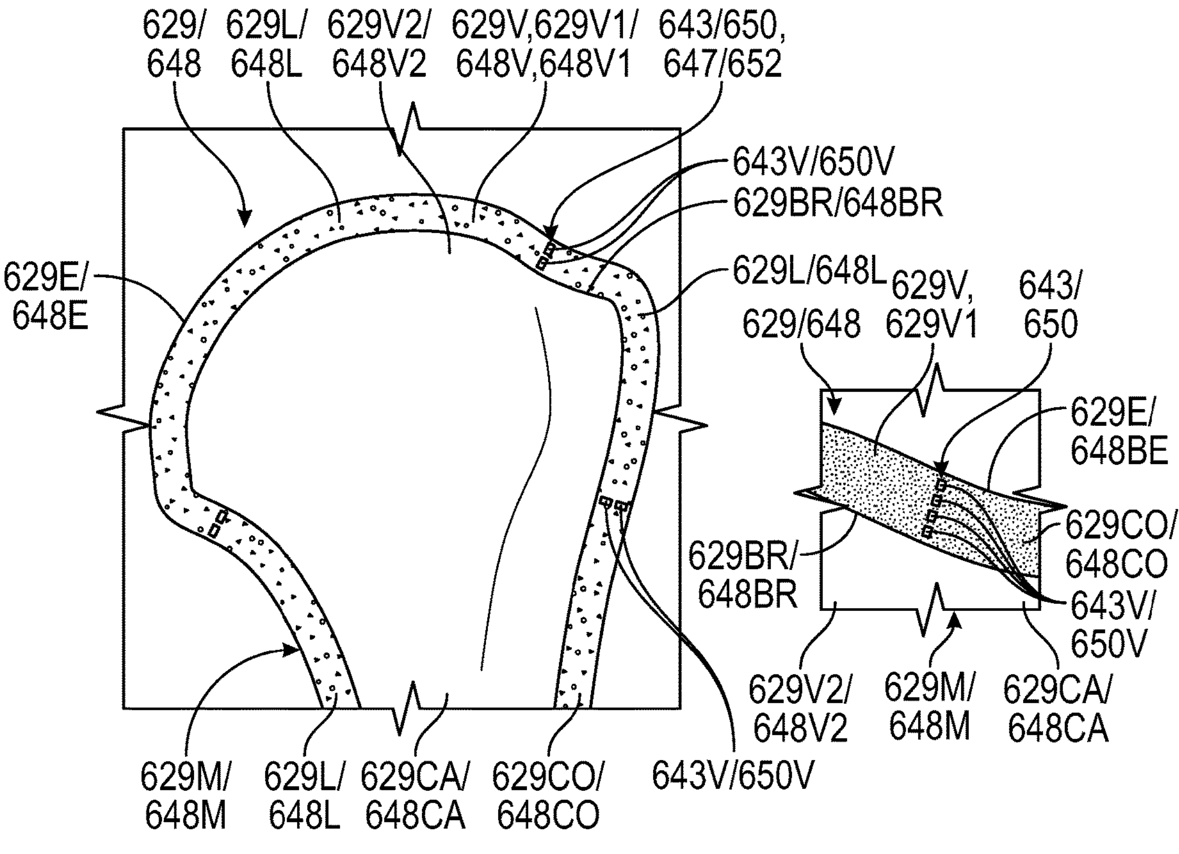
FIG. 23
FIG. 24

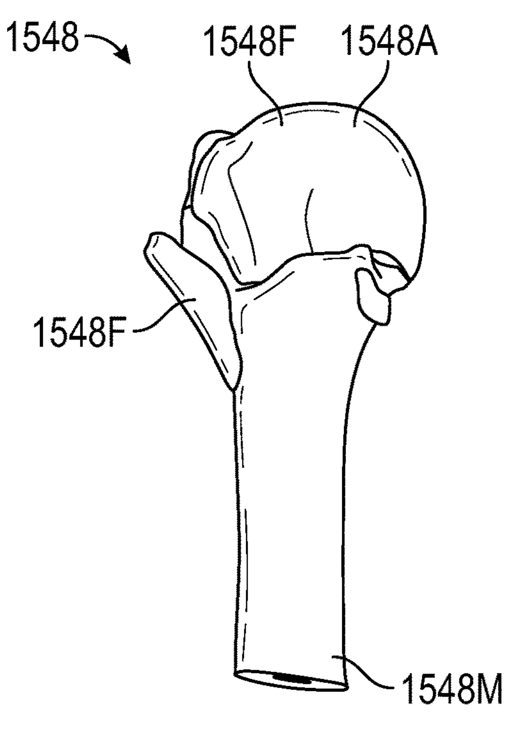
FIG. 42A
1548
1548F
1548A
1548F
1548F
1548M
FIG. 42B
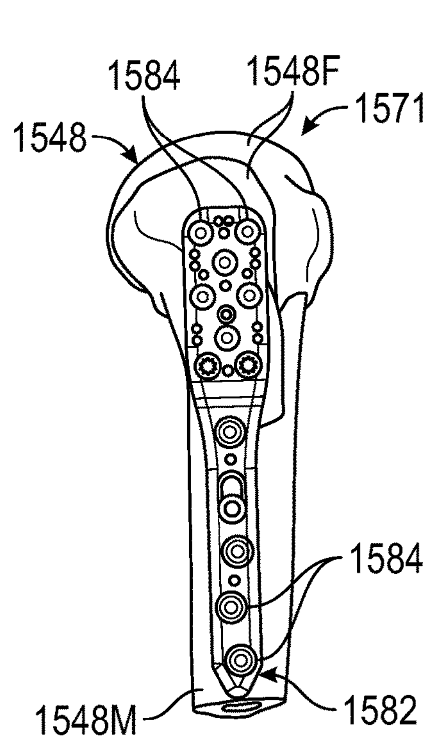
FIG. 42C
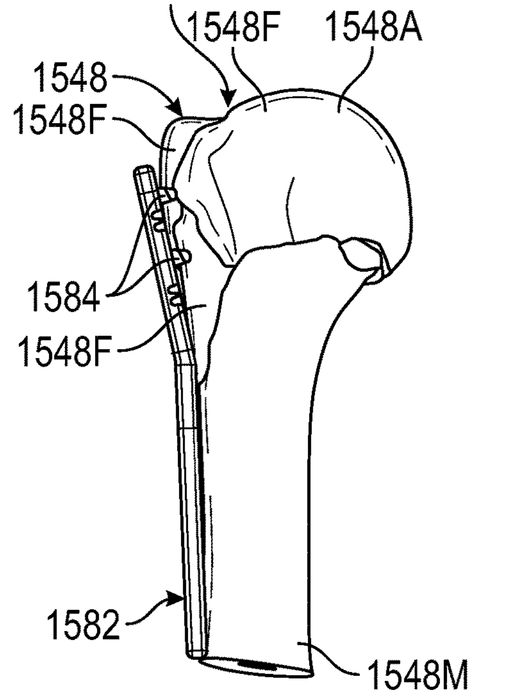
FIG. 42D

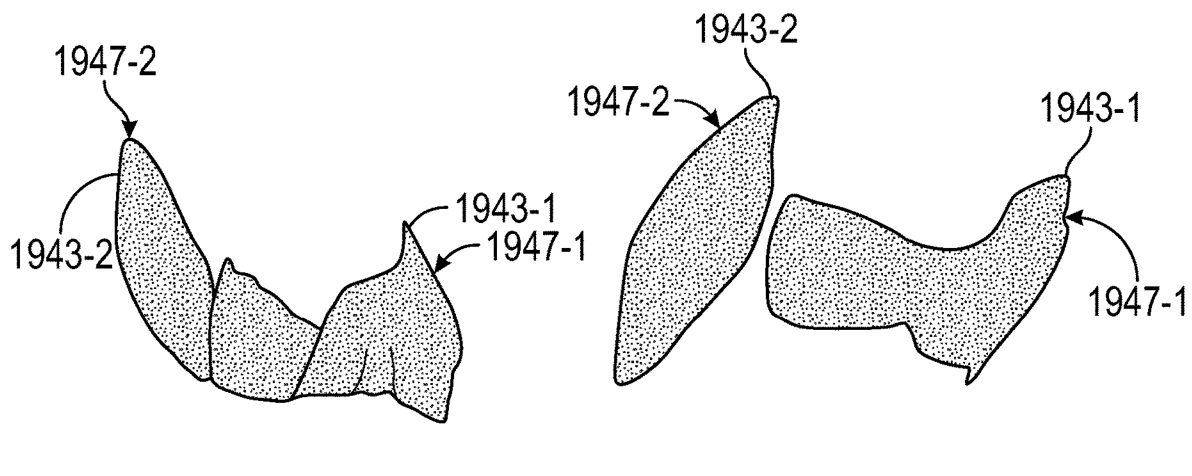
FIG. 50
FIG. 51
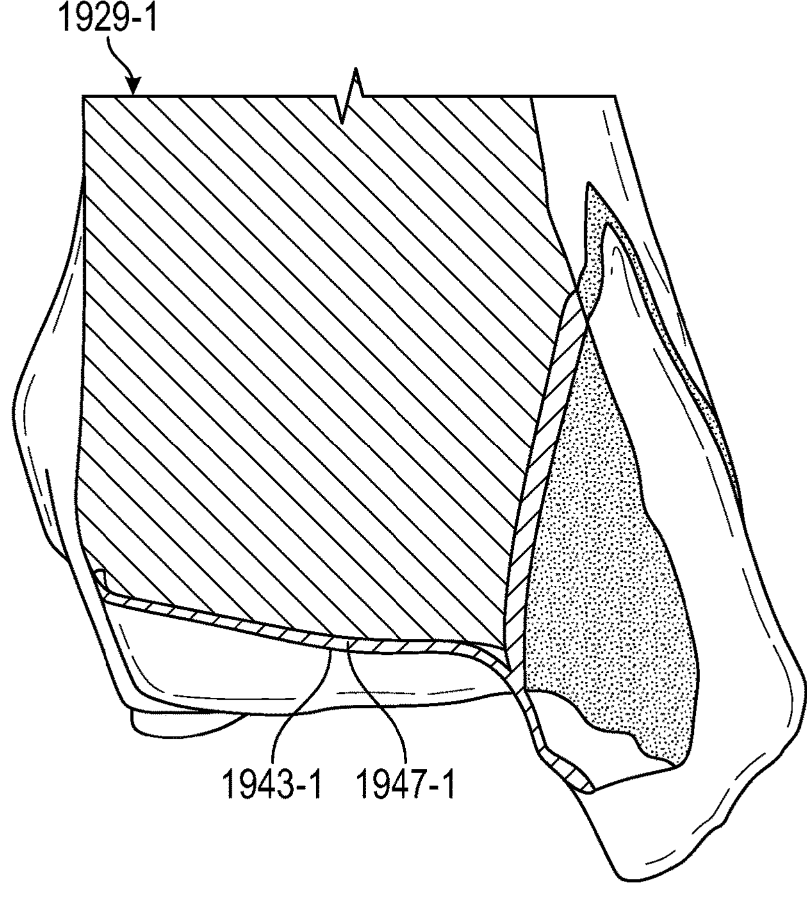
FIG. 52

FRACTURE MODELS, SYSTEMS AND ASSOCIATED METHODS

CROSS-REFERENCE TO RELATED APPLICATION

This application claims the benefit of U.S. Application No. 63/480,361, filed on Jan. 18, 2023, incorporated by reference herein in its entirety.

BACKGROUND

This disclosure relates to surgical systems, devices and methods for planning and implementing surgical procedures utilizing physical models of anatomy.

Patients may experience a fracture of one or more bones due to trauma. A surgeon may reduce the fracture and may secure the fragments of the bone with an implant to restore functionality to the patient.

Surgeons may prepare for an orthopaedic surgery by performing a procedure on a cadaveric or saw bone specimen.

SUMMARY

This disclosure relates to systems, devices and methods of performing a surgical procedure. The systems may be utilized for performing one or more surgical procedures on physical anatomical models representative of anatomy. The physical anatomical models may be severable along a fracture path to establish one or more fragments. The physical anatomical models and associated fracture paths may be established based on virtual anatomical models of anatomy.

A physical anatomical model according to an implementation may include a main body including an external surface that may be associated with an anatomical profile of a bone. The main body may include a fracture path that may establish one or more localized regions. The main body may be severable along the fracture path to establish one or more fragments that may be associated with a respective one of the one or more localized regions.

An orthopaedic system according to an implementation may include a physical anatomical model including a main body having a fracture path. A fracture tool may be adapted to cause the main body to sever along the fracture path to establish one or more fragments.

A system for rehearsing a surgical procedure according to an implementation may include a computing device including a processor coupled to memory. The processor may be configured to access a virtual anatomical model from the memory. The virtual anatomical model may be associated with an anatomy. The processor may be configured to cause the virtual anatomical model to be displayed in a graphical user interface. The processor may be configured to assign a fracture pattern to the virtual anatomical model based on one or more parameters. The processor may be configured to generate a configuration associated with a physical anatomical model that may be representative of the virtual anatomical model. The configuration may specify a fracture path established according to the assigned fracture pattern.

A method of establishing a physical anatomical model for a surgical procedure according to an implementation may include selecting a virtual anatomical model associated with an anatomy. The method may include assigning a fracture pattern to the virtual anatomical model based on one or more parameters. The method may include generating a configuration associated with a physical anatomical model that may be representative of the virtual anatomical model. The configuration may specify a fracture path established according to the assigned fracture pattern.

The present disclosure may include any one or more of the individual features disclosed above and/or below alone or in any combination thereof.

The various features and advantages of this disclosure will become apparent to those skilled in the art from the following detailed description. The drawings that accompany the detailed description can be briefly described as follows.

BRIEF DESCRIPTION OF THE DRAWINGS

FIG. 22 discloses another implementation of an anatomical model relative to an indicator.

FIGS. 23-24 disclose another implementation of an anatomical model incorporating one or more voids.

FIGS. 42A-42B disclose fragmentary states of a physical anatomical model.

FIGS. 42C-42D disclose an implant positioned and secured to the physical anatomical model of FIG. 42B.

FIGS. 50-51 disclose isolated views of the fracture volumes of FIG. 48 at different orientations.

FIG. 52 discloses a sectional view of one of the virtual anatomical models and the associated fracture volume of FIG. 48.

Like reference numbers and designations in the various drawings indicate like elements.

DETAILED DESCRIPTION

Figure 1:
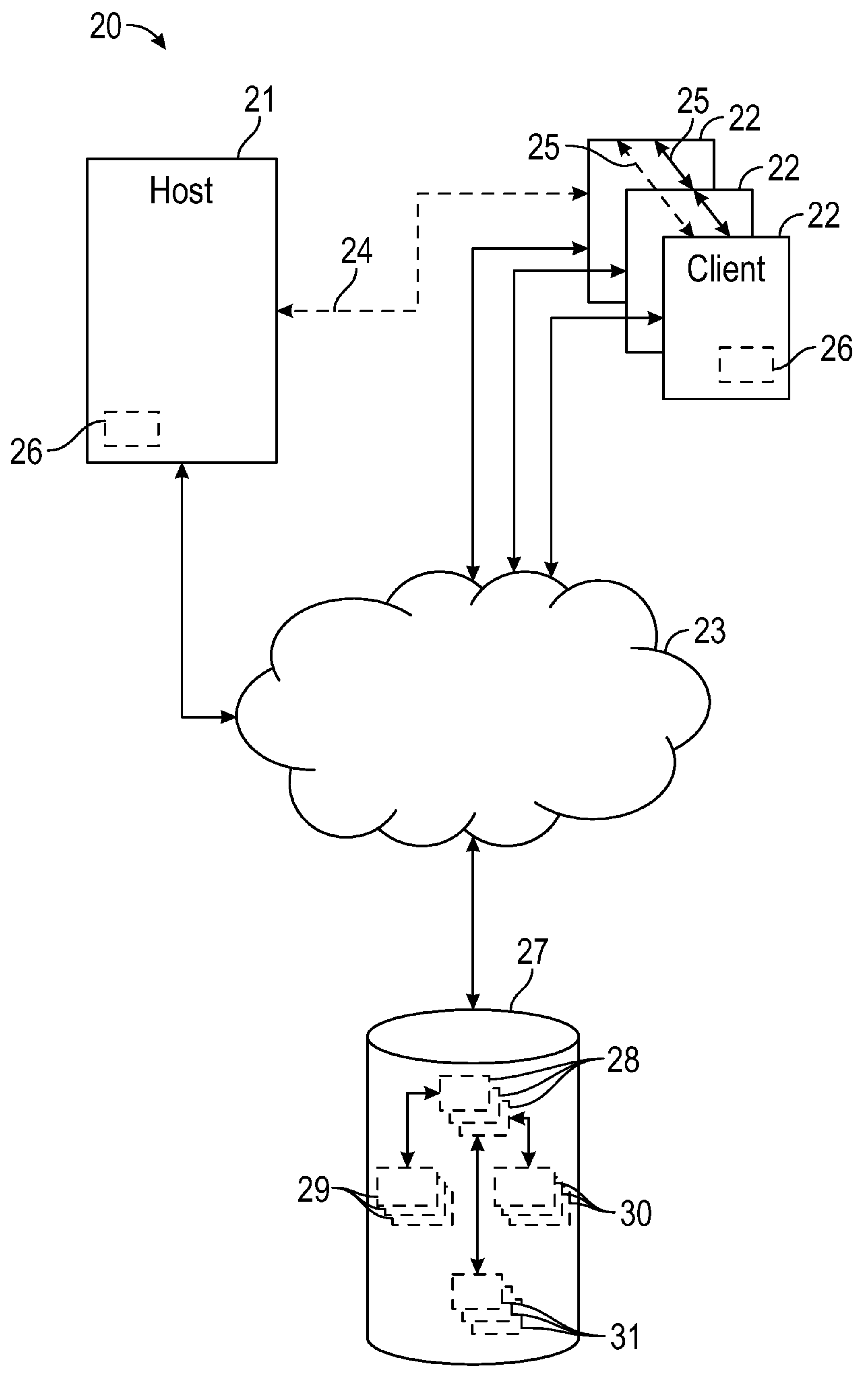
FIG. 1 discloses an exemplary planning system.

This disclosure relates to surgical systems, devices and methods for planning and implementing surgical procedures utilizing physical models of anatomy. Physical anatomical models may be utilized to rehearse and train for various surgical procedures, including the repair of fractures.

The disclosed techniques may be utilized to provide the surgeon a training experience that may be targeted or tailored to the surgeon based on procedure, skill set, experience, etc. The surgeon may select a particular configuration of a virtual anatomical model that may be fabricated or otherwise formed to establish a physical anatomical model based on the anatomy or pathology that the surgeon may intend to treat. In scenarios, the surgeon may not be familiar with a particular fracture type or other deformity and may choose to train utilizing that configuration of the physical anatomical model. The surgeon may utilize the physical anatomical model to train with particular instrumentation, implants and other devices that may be intended for a planned surgery to treat a patient. Once training on the physical anatomical model is completed, the surgeon may select a more challenging case in a subsequent training cycle.

The surgeon, assistant or other user may interact with a graphical user interface (GUI) to select various parameters or characteristics of the physical anatomical model. The parameters may include anatomy, patient, fracture classification, case, etc., to establish a desired configuration of the physical anatomical model. The surgeon may tailor or select one or more variables or parameters specific to a fracture classification scheme, depending on what the surgeon would like to train. The specified parameters may be represented in the physical anatomical model.

The surgeon may interact with the user interface to select a desired case associated with a respective virtual anatomical model. The surgeon may interact with the user interface to select a prior case. The surgeon may select a case corresponding to an intended patient or may select a prior or hypothetical case that may closely correspond to a particular fracture classification.

Various techniques may be utilized to establish the physical anatomical models, including any of the techniques disclosed herein. A virtual fracture pattern (e.g., virtual fracture path) and/or virtual fracture volume may be established relative to a virtual anatomical model. The fracture pattern may be established based on one or more parameters of a fracture classification scheme. The virtual fracture volume may be established along or otherwise adjacent to the fracture pattern. A physical fracture path and/or physical fracture volume may be established based on the virtual fracture pattern and/or virtual fracture volume, which may be incorporated in the physical anatomical model. The fracture volume may establish a relatively weaker localized region of the physical anatomical model, which may facilitate fragmentation of the physical anatomical model. The surgeon may reassemble (e.g., reduce) the fragment(s) of the physical anatomical model. The surgeon may secure the fragment(s) to each other and/or a remainder of the physical anatomical model, such as with a bone plate or another implant. The anatomical model may incorporate one or more indicators for facilitating evaluation of the repair.

A fracture tool may be utilized to engage and establish a fragmentation state of the physical anatomical model. The surgeon or clinical user may manipulate the fracture tool to establish one or more fragments. The fracture tool may exert a compressive force on the physical anatomical model to cause the physical anatomical model to fracture along a fracture path and/or fracture volume to establish the fragment(s).

The repaired physical anatomical model may serve as an artifact for the surgeon. The surgeon may leave a training facility with a revised physical anatomical model once training is completed. The surgeon may refer to the revised physical anatomical model prior to and during a surgical procedure on a respective patient.

A physical anatomical model according to an implementation may include a main body including an external surface that may be associated with an anatomical profile of a bone. The main body may include a fracture path that may establish one or more localized regions. The main body may be severable along the fracture path to establish one or more fragments that may be associated with a respective one of the one or more localized regions.

In any implementations, the fracture path may include one or more segments. Each of the one or more segments may establish a loop about the respective localized region.

In any implementations, the fracture path may be established according to a predetermined fracture pattern.

In any implementations, the main body may include a first volume and a second volume. The first volume may establish the external surface of the main body and may be representative of cortical bone. The second volume may be representative of cancellous bone.

In any implementations, the external surface along at least one of the localized regions may be associated with an articular surface of a joint.

In any implementations, the fracture path may extend along a boundary region between the first volume and the second volume. The main body may include a fracture volume established along the fracture path such that the fracture volume may be at least partially embedded in the first volume. The main body may be severable along the fracture volume to establish the one or more fragments.

In any implementations, the first volume may have a first property. The fracture volume may have a second property that may differ from the first property.

In any implementations, the first property may include a first material strength. The second property may include a second material strength that may be less than the first material strength.

In any implementations, one or more extensions may extend from the external surface of the main body adjacent to the fracture path. The one or more extensions may be representative of soft tissue.

In any implementations, the main body may include one or more indicators that may be associated with the fracture path.

In any implementations, the one or more indicators may include a plurality of graduations that may be distributed along a length of the fracture path.

In any implementations, the one or more indicators may include an indication path along the external surface of the main body. The indication path may be dimensioned to follow a length of the fracture path.

In any implementations, the main body may include a fracture volume that may be established along the fracture path. The main body may be severable along the fracture volume to establish the one or more fragments. The one or more indicators may include a visual contrast between the main body and the fracture volume.

In any implementations, the fracture volume may be spaced apart from the external surface of the main body.

In any implementations, the one or more indicators may include a shape established along the external surface of the main body. The shape may span between at least two of the localized regions.

In any implementations, the shape may be a silhouette associated with a perimeter of an orthopaedic implant securable to adjacent bone fragments.

In any implementations, a fracture volume may be associated with the fracture path. The fracture volume may extend substantially through the main body such that the main body may be severable along the fracture volume to establish the one or more fragments.

In any implementations, the main body may have a first property. The fracture volume may have a second property that may differ from the first property.

In any implementations, the fracture volume may include at least one indicator adapted to selectively communicate a state of the physical anatomical model in response to an external force.

In any implementations, the fracture volume may include a compressible material.

In any implementations, the fracture volume may be adapted to release an amount of fluid in response to the external force exceeding a preselected limit.

In any implementations, the fracture volume may be adapted to release one or more objects in response to the external force exceeding a preselected limit.

In any implementations, the main body may include a polymeric material.

In any implementations, the anatomical profile of the bone may be associated with a long bone.

An orthopaedic system according to an implementation may include a physical anatomical model including a main body having a fracture path. A fracture tool may be adapted to cause the main body to sever along the fracture path to establish one or more fragments.

In any implementations, the main body may include a first volume and a second volume. The first volume may establish an external surface of the main body and may be representative of cortical bone. The second volume may be representative of cancellous bone.

In any implementations, the fracture tool may include a clamp having a first clamp element and a second clamp element. The first clamp element may include a plurality of configurable engagement elements that may be dimensioned to engage selectable contact points along the main body. Each of the engagement elements may be adapted to cooperate with the second clamp element to apply a compressive force at the respective contact point to cause the main body to sever along the fracture path to establish the one or more fragments.

In any implementations, a plurality of contact indicators may be established along an external surface of the main body adjacent to the respective contact points. Each of the contact indicators may be associated with a respective one of the engagement elements.

A system for rehearsing a surgical procedure according to an implementation may include a computing device including a processor coupled to memory. The processor may be configured to access a virtual anatomical model from the memory. The virtual anatomical model may be associated with an anatomy. The processor may be configured to cause the virtual anatomical model to be displayed in a graphical user interface. The processor may be configured to assign a fracture pattern to the virtual anatomical model based on one or more parameters. The processor may be configured to generate a configuration associated with a physical anatomical model that may be representative of the virtual anatomical model. The configuration may specify a fracture path established according to the assigned fracture pattern.

In any implementations, the processor may be configured to generate the configuration such that the physical anatomical model may be severable along the fracture path to establish one or more fragments.

In any implementations, the processor may be configured to generate a fracture volume that may follow a length of the fracture pattern. The configuration may be established according to the fracture volume.

In any implementations, the fracture pattern may include a first fracture path and a second virtual fracture path that may be spaced apart from each other. The fracture volume may be bounded between the first and second fracture paths.

In any implementations, the fracture volume may be associated with a weaker material than an adjacent portion of the virtual anatomical model.

In any implementations, the configuration may specify one or more indicators associated with the fracture path.

In any implementations, the one or more parameters may be associated with a predefined fracture classification scheme. The processor may be configured to assign the fracture pattern to the virtual anatomical model in response to setting the one or more parameters associated with the predefined fracture classification scheme.

In any implementations, the virtual anatomical model may include a first volume and a second volume. The first volume may be representative of cortical bone. The second volume may be representative of cancellous bone.

In any implementations, the processor may be configured to generate the fracture pattern. The fracture pattern may extend along a boundary region between the first volume and the second volume.

In any implementations, the processor may be configured to generate a fracture volume that may follow a length of the fracture pattern. The configuration may be established according to the fracture volume.

In any implementations, the configuration may specify one or more indicators associated with the fracture path.

In any implementations, the one or more indicators may include at least one or more of an indication path that may follow a length of the fracture path, a plurality of graduations that may be distributed along the length of the fracture path, a shape that may span across the fracture path, and a visual contrast between the fracture path and an adjacent portion of the physical anatomical model.

In any implementations, the at least one indicator may include a silhouette. The silhouette may be associated with a perimeter of an orthopaedic implant securable to adjacent bone fragments.

In any implementations, the processor may be configured to generate a fracture volume based on the fracture pattern such that the fracture volume may extend substantially through a main body of the physical anatomical model such that the main body may be severable along the fracture volume to establish one or more fragments.

In any implementations, the main body may have a first property. The fracture volume may have a second property that may differ from the first property.

In any implementations, the fracture volume may include at least one indicator associated with a state of the physical anatomical model.

In any implementations, the fracture volume may include a compressible material.

A method of establishing a physical anatomical model for a surgical procedure according to an implementation may include selecting a virtual anatomical model associated with an anatomy. The method may include assigning a fracture pattern to the virtual anatomical model based on one or more parameters. The method may include generating a configuration associated with a physical anatomical model that may be representative of the virtual anatomical model. The configuration may specify a fracture path established according to the assigned fracture pattern.

In any implementations, the one or more parameters may be associated with a predefined fracture classification scheme. The step of assigning the fracture pattern may occur in response to setting the one or more parameters associated with the predefined fracture classification scheme.

In any implementations, the method may include causing the virtual anatomical model and the assigned fracture pattern to be displayed in a graphical user interface.

In any implementations, the method may include setting the one or more parameters in response to user interaction with the graphical user interface.

In any implementations, the method may include forming the physical anatomical model based on the configuration. The fracture path may establish one or more localized regions of the physical anatomical model. The physical anatomical model may be severable along the fracture path to establish one or more fragments associated with the respective localized regions.

In any implementations, the forming step may include printing layers of material on each other to establish the physical anatomical model.

In any implementations, the physical anatomical model may include a first volume and a second volume. The first volume may be representative of cortical bone. The second volume may be representative of cancellous bone.

In any implementations, the configuration may specify a fracture volume that may follow a length of the fracture path. The physical anatomical model may be severable along the fracture volume to establish the one or more fragments.

In any implementations, the configuration may specify one or more indicators associated with the fracture path.

In any implementations, the one or more indicators may include a plurality of contact indicators that may be distributed along the physical anatomical model. Each of the contact indicators may be associated with a respective contact element of a fracture tool. A main body of the physical anatomical model may be severable along the fracture path to establish one or more fragments in response to causing the fracture tool to apply an amount of force at a contact point along the physical anatomical model adjacent to the respective contact indicator.

In any implementations, the configuration may specify a fracture volume that may span between opposite sides of the fracture path such that the fracture volume may extend substantially through a main body of the physical anatomical model. The physical anatomical model may be severable along the fracture volume to establish one or more fragments.

FIG. 1 illustrates a planning system 20 that may be utilized for planning surgical procedures according to an implementation. The system 20 may be used for planning orthopaedic procedures, including pre-operatively, intra-operatively and/or post-operatively to create, edit, execute and/or review surgical plans. The system 20 may be used for training and rehearsing for various surgical procedures, including prior cases and surgical plans for patients and hypothetical cases.

The system 20 may include a host computer 21 and one or more client computers 22. The host computer 21 may be configured to execute one or more software programs. In implementations, the host computer 21 may include more than one computer jointly configured to process software instructions serially or in parallel.

The host computer 21 may be in communication with one or more networks such as a network 23 comprised of one or more computing devices. The network 23 may be a private local area network (LAN), a private wide area network (WAN), the Internet, or a mesh network.

The host computer 21 and each client computer 22 may include one or more of a computer processor, memory, storage means, network device and input and/or output devices and/or interfaces. The input devices may include a keyboard, mouse, etc. The output device may include a monitor, speakers, printers, etc. The memory may include UVPROM, EEPROM, FLASH, RAM, ROM, DVD, CD, a hard drive, or other computer readable medium which may store data and/or other information relating to the features and techniques disclosed herein. The host computer 21 and each client computer 22 may be a desktop computer, laptop computer, smart phone, tablet, or any other computing device. The interface may facilitate communication with the other systems and/or components of the network 23.

Each client computer 22 may be configured to communicate with the host computer 21 directly via a direct client interface 24 or over the network 23. The client computers 22 may be configured to execute one or more software programs, such as various surgical tools. Each client computer 22 may be operable to access and locally and/or remotely execute a planning environment 26. The planning environment 26 may be a standalone software package or may be incorporated into another surgical tool. The planning environment 26 may be configured to communicate with the host computer 21 either over the network 23 or directly through the direct client interface 24. In implementations, the client computers 22 may be configured to communicate with each other directly via a peer-to-peer interface 25.

The planning environment 26 may provide a display or visualization of one or more virtual anatomical models 29 and related images and/or one or more implant models 30 via one or more graphical user interfaces (GUI). Each anatomical model 29, implant model 30, and related images and other information may be stored in one or more files or records according to a specified data structure.

The system 20 may include at least one storage system 27, which may be operable to store or otherwise provide data to other computing devices. The storage system 27 may be a storage area network device (SAN) configured to communicate with the host computer 21 and/or the client computers 22 over the network 23. In implementations, the storage system 27 may be incorporated within or directly coupled to the host computer 21 and/or client computers 22. The storage system 27 may be configured to store one or more of computer software instructions, data, database files, configuration information, etc.

In implementations, the system 20 may be a client-server architecture configured to execute computer software on the host computer 21, which may be accessible by the client computers 22 using either a thin client application or a web browser executing on the client computers 22. The host computer 21 may load the computer software instructions from local storage, or from the storage system 27, into memory and may execute the computer software using the one or more computer processors.

The system 20 may include one or more databases 28. The databases 28 may be stored at a central location, such as the storage system 27. In implementations, one or more databases 28 may be stored at the host computer 21 and/or may be a distributed database provided by one or more of the client computers 22. Each database 28 may be a relational database configured to associate one or more anatomical models 29 and/or one or more implant models 30 to each other and/or a surgical plan 31. Each surgical plan 31 may be associated with a respective patient. Each anatomical model 29, implant model 30 and surgical plan 31 may be assigned a unique identifier or database entry. The database 28 may be configured to store data corresponding to the anatomical models 29, implant models 30 and surgical plans 31 in one or more database records or entries, and/or may be configured to link or otherwise associate one or more files corresponding to each respective anatomical model 29, implant model 30 and surgical plan 31. Anatomical models 29 stored in the database(s) 28 may correspond to respective patient anatomies from prior and/or planned surgical cases, and may be arranged into one or more predefined categories such as sex, age, ethnicity, size, defect category, procedure type, etc. The anatomical models 29 and/or implant models 30 may be associated with respective instrumentation and devices to implement the associated surgical plan 31.

Each anatomical model 29 may include information obtained from one or more medical devices or tools, such as a computerized tomography (CT), magnetic resonance imaging (MRI) machine and/or X-ray machine, that may obtain one or more images of a patient. The anatomical model 29 may include one or more digital images and/or coordinate information relating to an anatomy of the patient obtained or derived from the medical device(s). In implementations, one or more of the anatomical models 29 may be created by a designer and may represent a hypothetical anatomy. Each implant model 30 may include coordinate information associated with a predefined design. The planning environment 26 may incorporate and/or interface with one or more modeling packages, such as a computer aided design (CAD) package, to render the models 29, 30 as two-dimensional (2D) and/or three-dimensional (3D) volumes or constructs. Each anatomical model 29 and implant model 30 may correspond to 2D and/or 3D geometry, and may be utilized to generate a wireframe, mesh and/or solid construct in a display.

The implant models 30 may correspond to implants and components of various configurations, shapes, sizes, procedures, instrumentation, etc. Each implant may include one or more components that may be situated at a surgical site including plates, anchors, screws, nails, suture, grafts, etc. Each implant model 30 may correspond to a single component or may include two or more components that may be configured to establish an assembly. The implant models 30 may include base plates coupled to an articulation member, bone plates configured to interconnect adjacent bones or bone fragments, intermedullary nails, suture anchors, etc. The articulation member may have an articular surface dimensioned to mate with an articular surface of an opposed bone or implant.

Each surgical plan 31 may be associated with one or more of the anatomical models 29 and/or implant models 30. The surgical plan 31 may include one or more revisions to the anatomical model 29 and information relating to a position of an implant model 30 relative to the original and/or revised anatomical model 29. The surgical plan 31 may include coordinate information relating to the revised anatomical model 29 and a relative position of the implant model 30 in predefined data structure(s). Revisions to each anatomical model 29, implant model 30 and surgical plan 31 may be stored in the database 28 automatically and/or in response to user interaction with the system 20.

One or more surgeons, assistants and other clinical users may be provided with a planning environment 26 via the client computers 22 and may simultaneously access each anatomical model 29, implant model 30 and surgical plan 31 stored in the database(s) 28. Each user may interact with the planning environment 26 to create, view and/or modify various aspects of the surgical plan 31. Each client computer 22 may be configured to store local instances of the anatomical models 29, implant models 30 and/or surgical plans 31, which may be synchronized in real-time or periodically with the database(s) 28. The planning environment 26 may be a standalone software package executed on a client computer 22 or may be provided as one or more services executed on the host computer 21.

Figure 2:
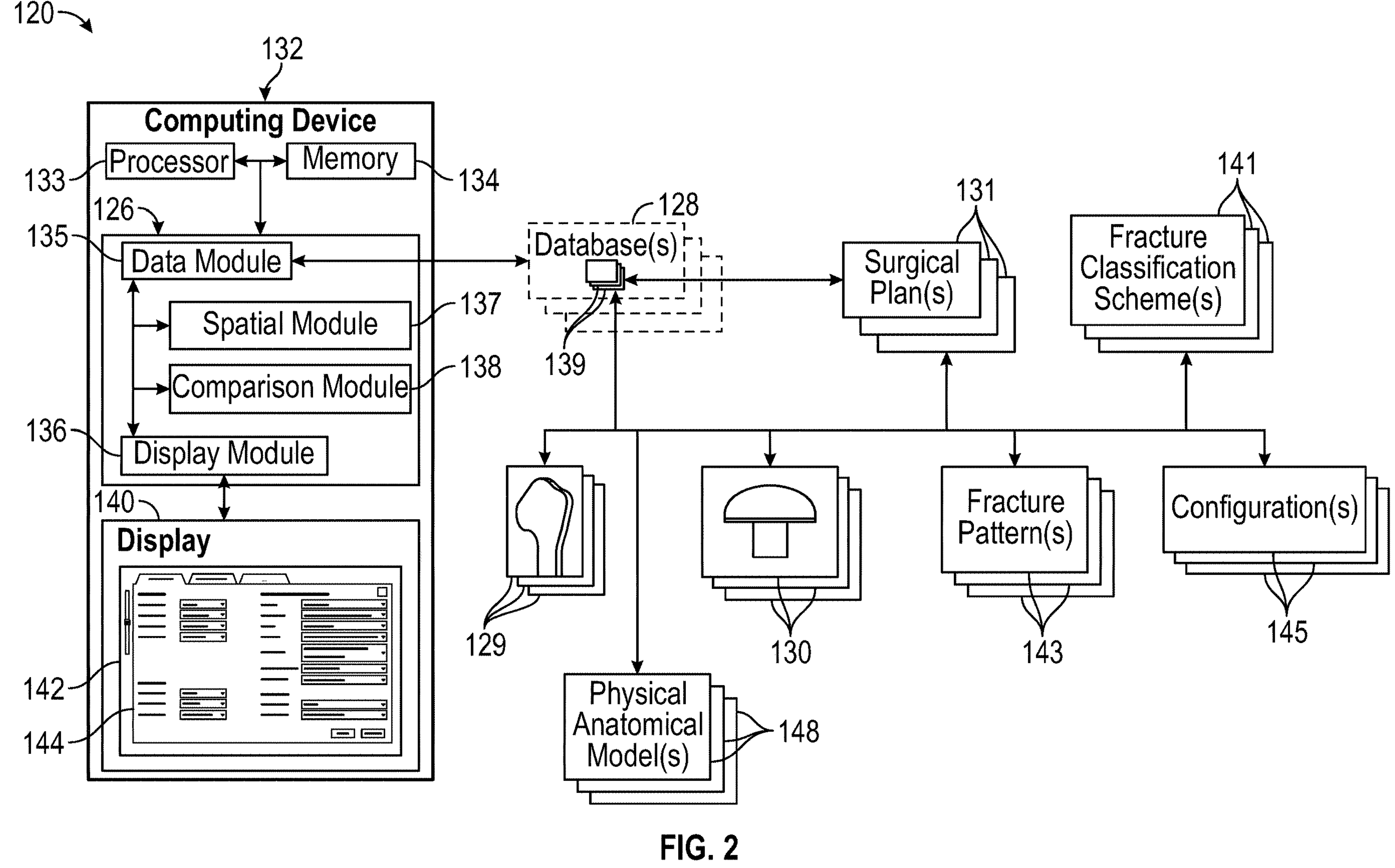
FIG. 2 discloses another exemplary planning system including a user interface.

FIG. 2 illustrates a surgical system 120 according to an implementation. The system 120 be utilized to facilitate planning, rehearsing and/or training for a surgical procedure. The system 120 may be utilized to plan, rehearse, train and implement various orthopaedic and other surgical procedures, such as an arthroplasty to repair a joint. The system 120 may be utilized in planning a resection or revision of one or more bones. The system 120 may be utilized in planning placement of an implant to restore functionality to a bone and/or joint, such as a shoulder joint during an anatomical or reverse shoulder procedure. The system 120 may be utilized in planning the repair of a fracture of one or more bones, including one or more long bones such as a humerus. Although the planning systems and methods disclosed herein primarily refer to repair of a shoulder, it should be understood that the planning system 120 may be utilized in the repair of other locations of the patient and other surgical procedures including repair of other joints such as an ankle, wrist, hand, hip or knee, and including repair of other tissue such as cartilage, muscles, tendons and ligaments.

The system 120 may be configured to generate one or more physical anatomical models, including any of the physical anatomical models disclosed herein. The surgeon may perform one or more modifications to the physical anatomical model to rehearse or train for a surgical procedure. The system 120 may be configured to generate configuration(s) associated with respective physical anatomical model(s). The configuration may be utilized in the formation of a physical anatomical model. Each physical anatomical model may be representative of a virtual anatomical model 129, including a substantially or generally corresponding geometry, texture density, porosity, color, etc. as the virtual anatomical model 129. The virtual anatomical model 129 may be associated with an anatomy, such as the anatomy of a patient and/or a hypothetical anatomy. The anatomical models 129 may include one or more anatomical features. The anatomical features may be representative of anatomy, including one or more bones including cartilage, cortical and/or cancellous bone tissue, soft tissue including muscle, ligaments and/or tendons, etc., and/or other tissue.

The system 120 may include a computing device 132. The computing device 132 may include at least one processor 133 coupled to memory 134. The computing device 132 may include any of the computing devices disclosed herein, such as the host computer 21 and/or client computer 22 of FIG. 1. The processor 133 may be configured to execute a planning environment 126 for creating, editing, executing and/or reviewing one or more surgical (e.g., pre-operative) plans 131 during pre-operative, intra-operative and/or post-operative phases of a surgical procedure. The processor 133 may be configured to access one or more virtual anatomical models 129 from a storage location such as the memory 134. The anatomical model 129 and surgical plan 131 may be associated with an actual case for a patient or may be a hypothetical case established for rehearsal and/or training surgeons, assistants medical staff and other clinical users.

The planning environment 126 may include at least a data module 135, display module 136, spatial module 137 and comparison module 138. The processor 133 may be configured to execute the data module 135, display module 136, spatial module 137 and comparison module 138. Although four modules are disclosed in the implementation of FIG. 2, it should be understood that fewer or more than four modules may be utilized and/or one or more of the modules may be combined to provide the disclosed functionality.

The data module 135 may be configured to access, retrieve and/or store data and other information in the database(s) 128 corresponding to one or more virtual anatomical model(s) 129, implant model(s) 130 and/or surgical plan(s) 131. The data and other information may be stored in the database 128 as one or more records or entries 139. In implementations, the data and other information may be stored in one or more files that may be accessible by referencing one or more objects or memory locations referenced by the records 139.

The memory 134 may be configured to access, load, edit and/or store instances of one or more anatomical models 129, implant models 130 and/or surgical plans 131 in response to one or more commands from the data module 135. The data module 135 may be configured to cause the memory 134 to store a local instance of the anatomical model(s) 129, implant model(s) 130 and/or surgical plan(s) 131 which may be synchronized with records 139 in the database(s) 128.

The display module 136 may be configured to display data and other information relating to one or more surgical plans 131 in at least one graphical user interface (GUI) 142. The computing device 132 may be coupled to a display device 140. The display module 136 may be configured to cause the display device 140 to display the virtual anatomical model 129 in the user interface 142. A surgeon or other clinical user may interact with the user interface 142 via the planning environment 126 to create, edit and/or review aspects of one or more anatomical models 129. The surgeon or other user may interact with the user interface 142 via the planning environment 126 to create, edit, execute and/or review aspects of one or more surgical plans 131.

Each surgical plan 131 may be associated with one or more (e.g., original) virtual anatomical models 129 prior to any revisions, which may substantially or generally approximate an anatomy. Each surgical plan 131 may be associated with one or more (e.g., revised) virtual anatomical models 129 that may incorporate one or more revisions to the anatomy and/or an associated physical anatomical model. The original and revised anatomical models 129 may be associated with each other in the surgical plan 131. In implementations, the revisions may be stored as one or more parameters of the original anatomical model 129.

The planning system 120 may be configured to generate a link to a surgical plan 131. The surgeon, assistant or other clinical user may interact with the link to review and edit the surgical plan 131. Interacting with the link may cause the planning system 120 to display or otherwise present aspects of the surgical plan 131 in the graphical user interface 142.

The planning system 120 may be utilized to generate a physical instance of a virtual anatomical model 129 that a surgeon may utilize for rehearsing or training for the repair of a fracture. The surgeon may interact with a fractured state of a physical anatomical model, which may be associated with the virtual anatomical model 129. Each fracture may be classified according to one or more fracture classification schemes 141. Various fracture classification schemes may be utilized in accordance with the teachings disclosed herein, including predefined industry classification schemes and/or user-defined classification schemes. Industry defined classification schemes may include the Müller AO Classification of fractures, the Neer Classification, and the AO Foundation and Orthopaedic Trauma Association (AO/OTA) Fracture Classification Scheme. The AO/OTA Fracture Classification Scheme may include a 2018 revision of the AO/OTA Fracture and Dislocation Classification Compendium released by the AO Foundation. The Neer Classification may be utilized to classify fractures of the proximal humerus. Other fracture classification schemes may be utilized in accordance with the teachings disclosed herein, including any known classification scheme recognized in the medical community.

The planning system 120 may be adapted to access one or more fracture classification schemes 141. The comparison module 138 may be adapted to access one or more fracture patterns (e.g., virtual fracture path) 143. Various techniques may be utilized to establish the fracture pattern 143, including any of the techniques disclosed herein. The planning system 120 may be adapted to associate each fracture patterns 143 with one or more of the fracture classification schemes 141. The data module 135 may be configured to access, retrieve and/or store data and other information in the database(s) 128 corresponding to one or more fracture classification schemes 141 and/or fracture patterns 143. The fracture classification schemes 141 and/or fracture pattern 143 may be predefined and/or may be established by the comparison module 138. In implementations, the planning system 120 may generate one or more fracture classification schemes 141 and/or fracture patterns 143 automatically and/or in response to user input. The fracture patterns 143 may be generated utilized various techniques, such as finite element analysis (FEA) and other parametric modeling.

The comparison module 138 may be adapted to associate each anatomical model 129 with one or more fracture classification schemes 141 and/or fracture patterns 143. The comparison module 138 may be adapted to assign one or more fracture classification schemes 141 to each fracture pattern 143, either automatically and/or in response to user interaction with the user interface 142 and/or another portion of the planning system 120. The data module 135 may be adapted to store and/or access an instance of each anatomical model 129 and an associated fracture classification scheme 141 and/or fracture pattern 143 in the database(s) 128 or another memory location. The comparison module 138 may be adapted to generate, revise or otherwise associate a surgical plan 131 with an anatomical model 129, fracture classification scheme 141 and/or fracture pattern 143.

Each fracture classification scheme 141 and/or fracture pattern 143 may be stored in a respective predefined data structure(s) in the database 128 or another portion of the system 120. The data and other information associated with the respective fracture classification scheme 141 and/or fracture pattern 143 may be stored in the database 128 as one or more respective records or entries 139. In implementations, the data and other information may be stored in one or more files that may be accessible by referencing one or more objects or memory locations referenced by the records 139. The memory 134 may be configured to access, load, edit and/or store instances of one or more fracture classification schemes 141 and/or fracture patterns 143 in response to one or more commands from the data module 135. The data module 135 may be configured to cause the memory 134 to store a local instance of the fracture classification scheme(s) 141 and/or fracture pattern(s) 143, which may be synchronized with records 139 in the database(s) 128.

The planning system 120 may be utilized to establish one or more physical anatomical models 148, including any of the physical anatomical models disclosed herein. The physical anatomical model 148 may be representative of an associated virtual anatomical model 129.

Figure 3:
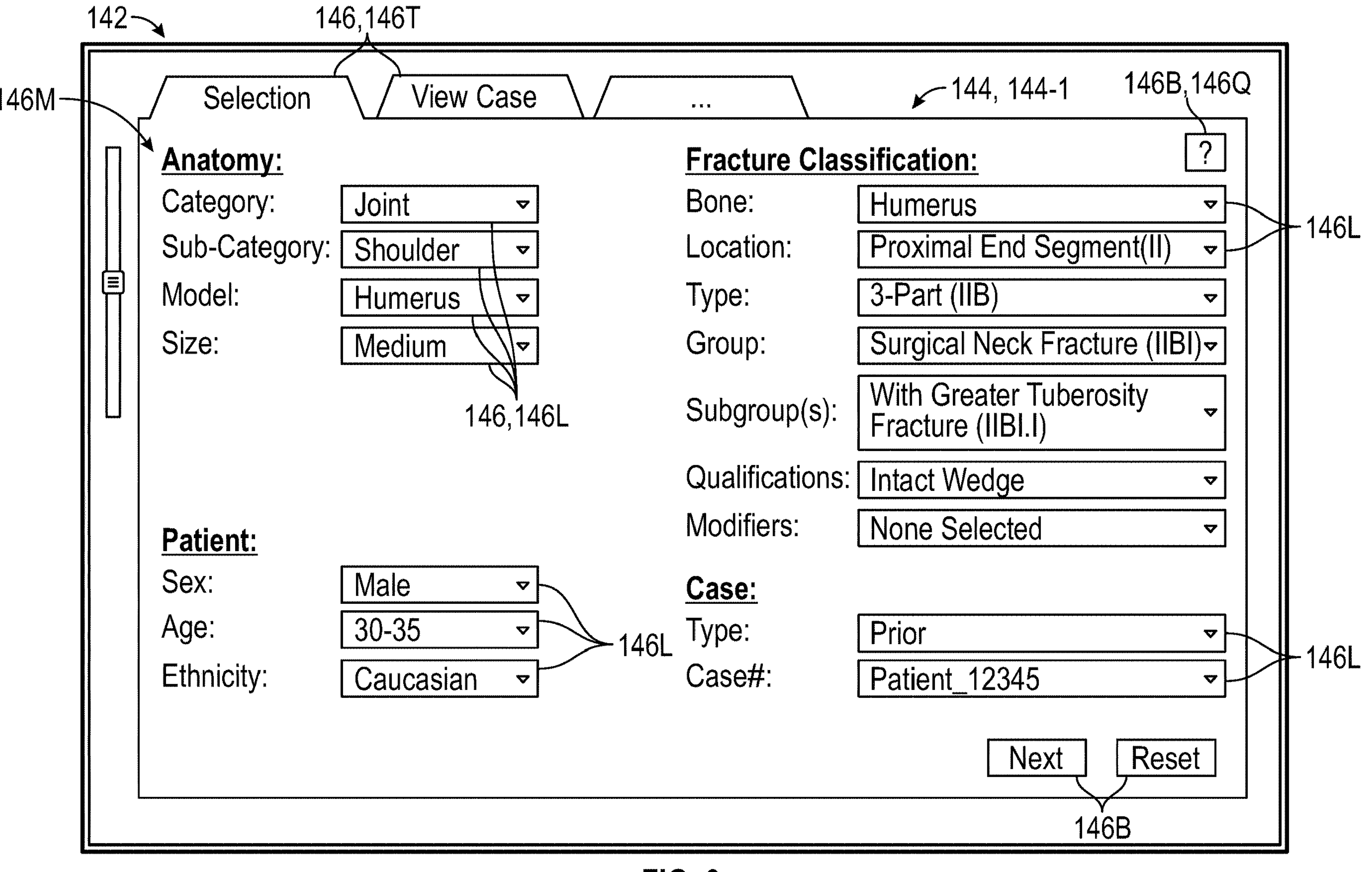
FIG. 3 discloses the user interface of FIG. 2 including a display window including various parameters.

Referring to FIG. 3, with continuing reference to FIG. 2, the user interface 142 may include one or more display windows 144 and one or more objects 146, such as a first display window 144-1. The objects 146 may include graphics such as menus, tabs, lists, entry fields and buttons accessible by user interaction, such as tabs 146T, buttons 146B, drop-down lists 146L, menus 146M, directional indicators 146D, 146R (e.g., FIG. 5), and graphics associated with respective display window(s) 144. In implementations, one or more entries may be specified in respective entry fields, including any parameters associated with the lists 146L. Geometric objects, including selected virtual anatomical model(s) 129, implant model(s) 130, fracture pattern(s) 143 and/or other information relating to a surgical plan 131 may be displayed in one or more of the display windows 144.

The comparison module 138 may be configured to assign a fracture pattern 143 to the virtual anatomical model 129 based on one or more parameters, including any of the parameters disclosed herein. The parameters may be associated with a predefined fracture classification scheme 141. The comparison module 138 may be configured to assign the fracture pattern 143 to the virtual anatomical model 129 in response to setting one or more parameters associated with the fracture classification scheme 141.

The surgeon or clinical user may interact with the display window 144 and/or another portion of the user interface 142 to select one or more anatomical models 129. Various parameters may be utilized to select the anatomical model(s) 129. The anatomical models 129 may be categorized by anatomy, patient, defect (e.g., fracture classification), case, etc. The parameters may be associated with respective objects 146 of the user interface 142. The parameters of the display window 144 may be interconnected to provide a filtering feature such that each selection of a parameter may cause the remaining parameter(s) to be filtered to depict available options. Each parameter may be associated with a set of anatomical models 129 accessible by the planning environment 126.

The display module 136 may be adapted to present one or more parameters associated with the anatomy, patient, fracture classification scheme and/or case to the surgeon or clinical user in the display window 144. The surgeon or clinical user may interact with the user interface 142 to select or otherwise specify one or more of the parameters. Anatomical parameters may be arranged in one or more lists 146L by category (e.g., joint, etc.), sub-category (e.g., shoulder, ankle, hip, hand, foot, etc.), model (e.g., glenoid, humerus, femur, pelvis, tibia, etc.) and anatomical size (e.g., small, medium, large). The categories may be subdivided by gross anatomy including surface anatomy (e.g., the external body), regional anatomy (e.g., specific regions of the body), and systemic anatomy (e.g., specific organ systems). The data module 135 may be adapted to cause the display module 136 to populate entries associated with the virtual anatomical model(s) 129 and other parameters including category, sub-category, model and/or size in respective lists 146L. The spatial module 137 may be configured to scale a geometry of the selected anatomical model 129 in response to selection of an anatomical size. The surgeon or clinical user may select or otherwise specify the anatomical parameters including category, sub-category, model and/or size of the anatomy in response to interaction with the display window 144 and/or another portion of the user interface 142. Each list 146L may be associated with one or more virtual anatomical model(s) 129. The anatomical model 129 may be associated with an anatomy of a patient, such as a prior case or a planned case, and/or a hypothetical anatomy. The surgeon or clinical user may select or otherwise specify parameter(s) associated with respective virtual anatomical model(s) 129.

The anatomical models 129 may be categorized by patient parameters. Various patient parameters may be utilized, such as sex, age and ethnicity. The patient parameters may be presented in respective lists 146L. The data module 135 may be adapted to cause the display module 136 to populate one or more patient parameters associated in the respective lists 146L. The data module 135 may be adapted to cause the display module 136 to populate entries associated with the anatomy and other parameters including category, sub-category, model and/or size in the respective lists 146L in response to specifying parameters associated with the patient population.

Case parameters may include case type (e.g., prior, planned and hypothetical), case number, etc. The surgeon may interact with the list(s) 146L and/or another portion of the user interface 142 to select and/or review a particular case, such as a prior, planned or hypothetical case associated with a surgical plan 131, which may be filtered by the data module 135 based on previous selection(s) of the parameters. The surgeon may interact with the user interface 142 to review prior cases, including prior cases for a particular surgical procedure, anatomy and/or group of patients. The planning system 120 may be configured to provide analysis of the prior case such as biometric testing of a repaired joint, finite element analysis (FEA), etc. The surgeon or clinical user may select a virtual anatomical model 129 corresponding to an intended patient. The selected virtual anatomical model 129 may correspond to an acquired CT scan of the patient. The surgeon may select a virtual anatomical model 129 that may be associated with a particular classification.

The data module 135 may be adapted to cause the display module 136 to populate entries associated with a case, such as type (e.g., prior, planned or hypothetical) and/or case number in respective lists 146L. The data module 135 may be adapted to cause the display module 136 to populate entries associated with the case and other parameters including type and/or case number in the respective lists 146L in response to specifying parameters associated with the patient population.

The surgical plan 131 may be associated with an anatomical model 129 prior to any revisions and may be associated with another (e.g., revised) anatomical model 129 incorporating one or more revisions based on implementation of an associated surgical procedure. Revisions may include removal of material utilizing one or more drilling, milling, resection, reaming and cutting operations. Revisions may include one or more fragmentary states of the anatomical model 129, including prior to and/or subsequent to registration of any associated fragments.

The display module 136 may be adapted to present one or more parameters of a fracture classification scheme 141 associated with the virtual anatomical model 129 in the user interface 142. The display module 136 may be adapted to display the parameter(s) associated with the classification scheme 141 in the first display window 144-1. The display module 136 may be configured present one or more parameters of a respective classification scheme 141 in response to selection of a bone type and/or fracture location. The display module 136 may be adapted to present one or more parameters associated with the classification scheme 141 in response to selection of a bone type (e.g., humerus, femur, tibia, etc.) and/or fracture location (e.g., proximal humeral fracture location) from one or more menus 146L and/or another portion of the user interface 142. The data module 135 may be adapted to cause the display module 136 to populate entries associated with parameter(s) of a fracture classification scheme 141 in respective lists 146L and/or other portion of the user interface 142. The fracture classification scheme 141 may be selected automatically and/or manually in response to one or more selections associated with anatomy, patient and/or case. The entries may include bone type (e.g., humerus), location (e.g., proximal end segment), type (e.g., two-part, three-part or four-part), group (e.g., surgical neck fracture) and subgroup(s) (e.g., with greater tuberosity fracture) and other parameters of the associated fracture classification scheme 141 such as qualifier(s) and/or modifier(s) in respective lists 146L.

The data module 135 may be adapted to access a virtual anatomical model 129 from memory, such as the memory 134 and/or database 128, in response to selecting one or more parameters in the display window 144 of the graphical user interface 142. The data module 135 may be configured to select an anatomical model 129 from memory, such as the database 128 or memory 134, in response to user interaction with the display window 144 or another portion of the user interface 142. The data module 135 may select a fracture pattern 143 in response to one or more of the parameters of the fracture classification scheme 141 of the selected virtual anatomical model 129 being selected or otherwise specified.

Figure 4:
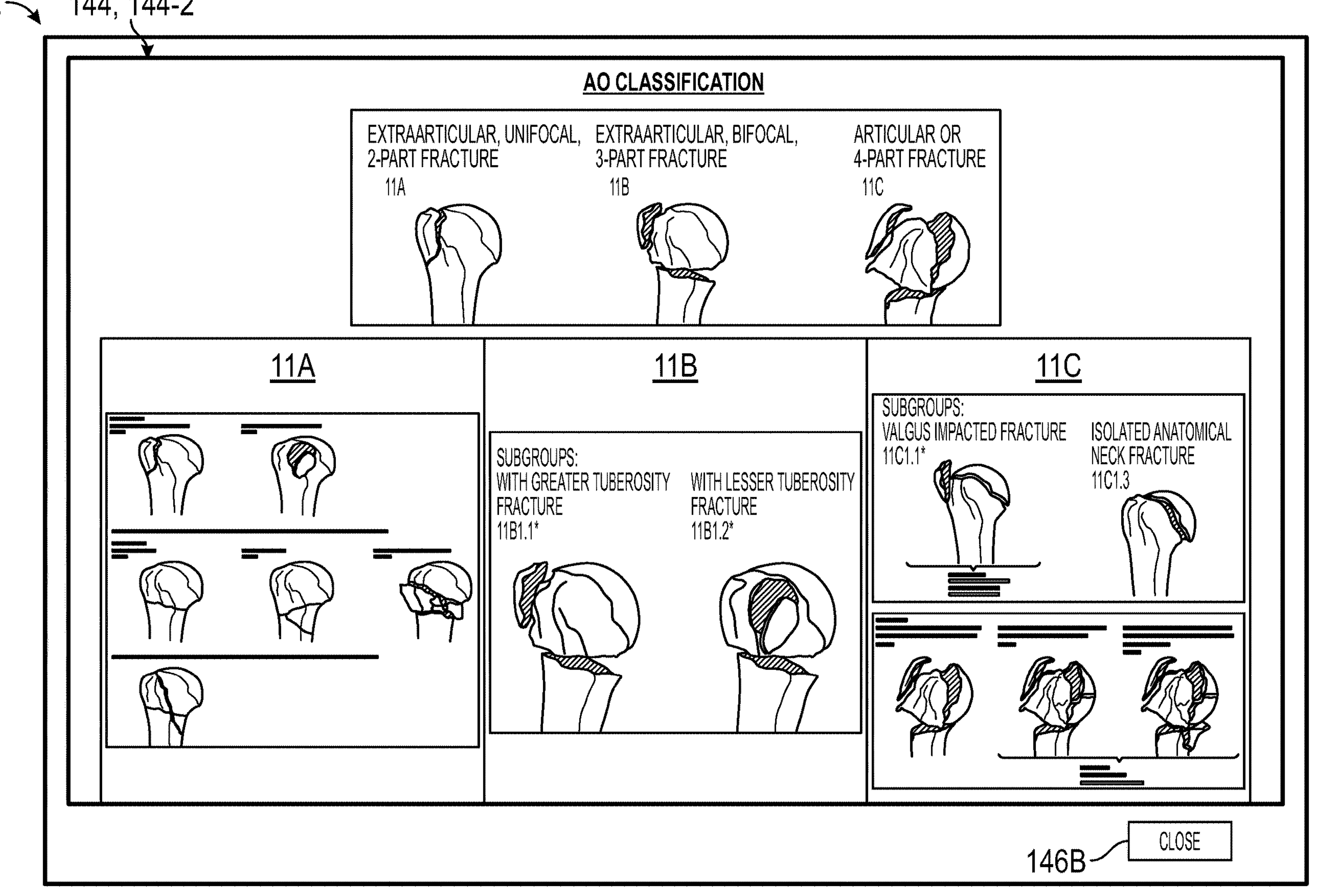
FIG. 4 discloses a display window of the user interface of FIG. 2 including a help screen presenting fracture classification information.

The surgeon or clinical user may select the virtual anatomical model 129 according to a severity of various defects, such as mild, severe, non-pathological, fractures, etc. Defect parameters may be established for the various defects and may be arranged by classification, subclassification, etc. The surgeon, assistant or other user may interact with a button 146B (see, e.g., question mark button 146Q) for an explanation of the defect parameters (see, e.g., second display window 144-2 of FIG. 4). In implementations, selection of a virtual anatomical model 129 from the list 146L may cause a help screen to be generated and displayed with one or more fracture classification options in response to selection of the button 146Q. The fracture classification options may be associated with a respective fracture classification scheme 141, including any of the fracture classification schemes disclosed herein. The surgeon or clinical user may select from the various classification parameters to rehearse and/or train for a surgical procedure, including the treatment of a fractured bone.

Figure 5:
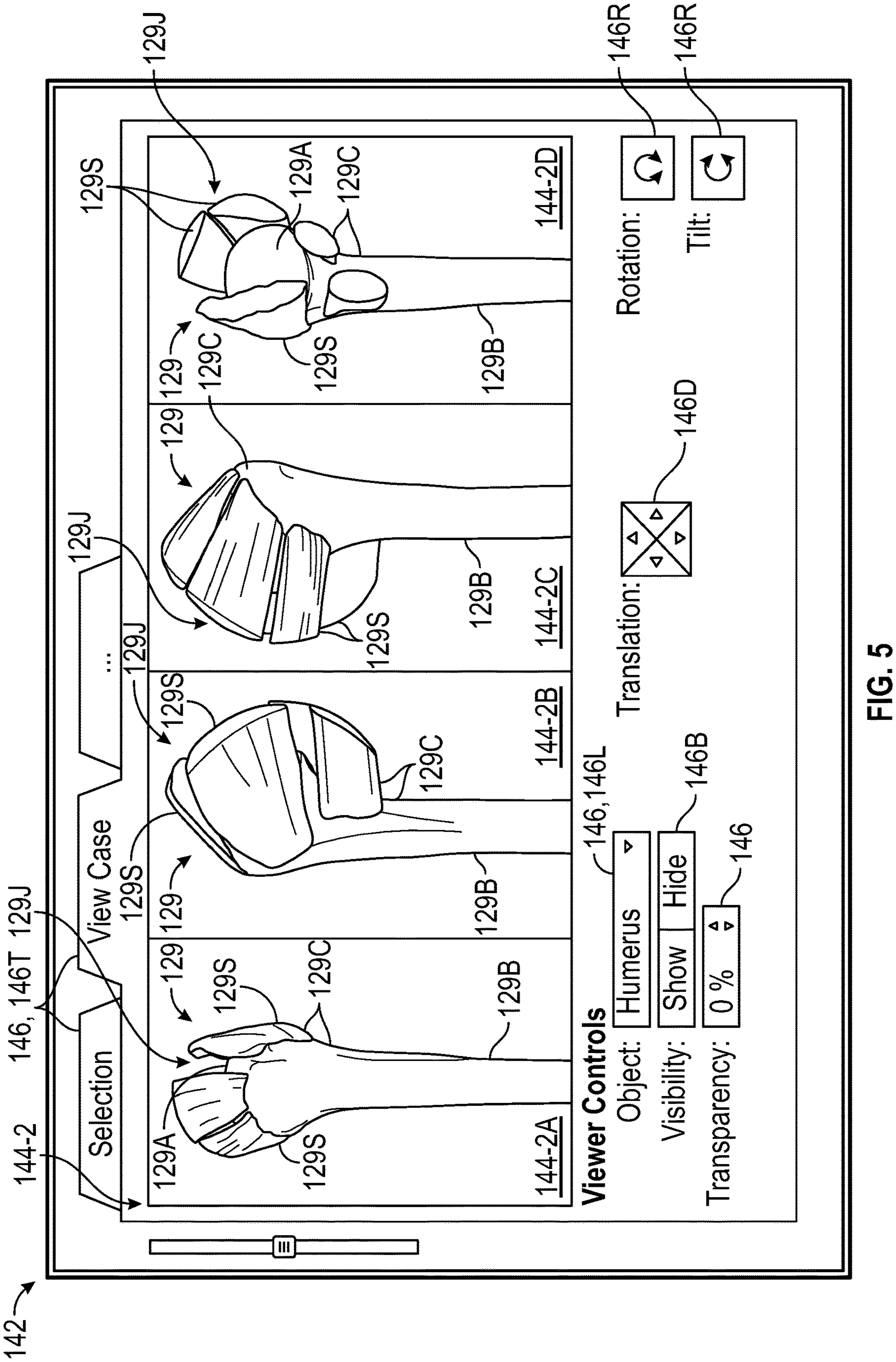
FIG. 5 discloses the user interface of FIG. 2 including display windows depicting a virtual anatomical model.

Referring to FIG. 5, with continuing reference to FIG. 2, a selected virtual anatomical model 129 may be displayed in one or more display windows 144 of the user interface 142. In the implementation of FIG. 5, the various views of the virtual anatomical model 129 may be displayed in display windows 144-2, such as a second set of display windows 144-2A through 144-2D. Each virtual anatomical model 129 may include one or more components 129C. The components 129C may include various representations of tissue, such as bone and soft tissue. Bone(s) may be represented by respective bone volume(s) 129B. Soft tissue(s) may be represented by respective soft tissue volume(s) 129S. Various representations of soft tissue may be utilized, such as tendons, ligaments, musculature and other soft tissue. The anatomical model 129 may establish a portion of a joint 129J. The bone volume(s) 129B may include at least articular surface 129A that may be dimensioned to cooperate with an adjacent articular surface to establish the joint 129J. Although four display windows 144-2A to 144-2D are shown in FIG. 5, it should be understood that fewer or more than four display windows 144 may be utilized in accordance with the teachings disclosed herein. The surgeon or clinical user may interact with one or more of the objects 146 to observe various aspects of the anatomical model 129. In implementations, the surgeon or clinical user may interact with list(s) 146L to select the respective anatomical object (e.g., humerus).

Figure 6:
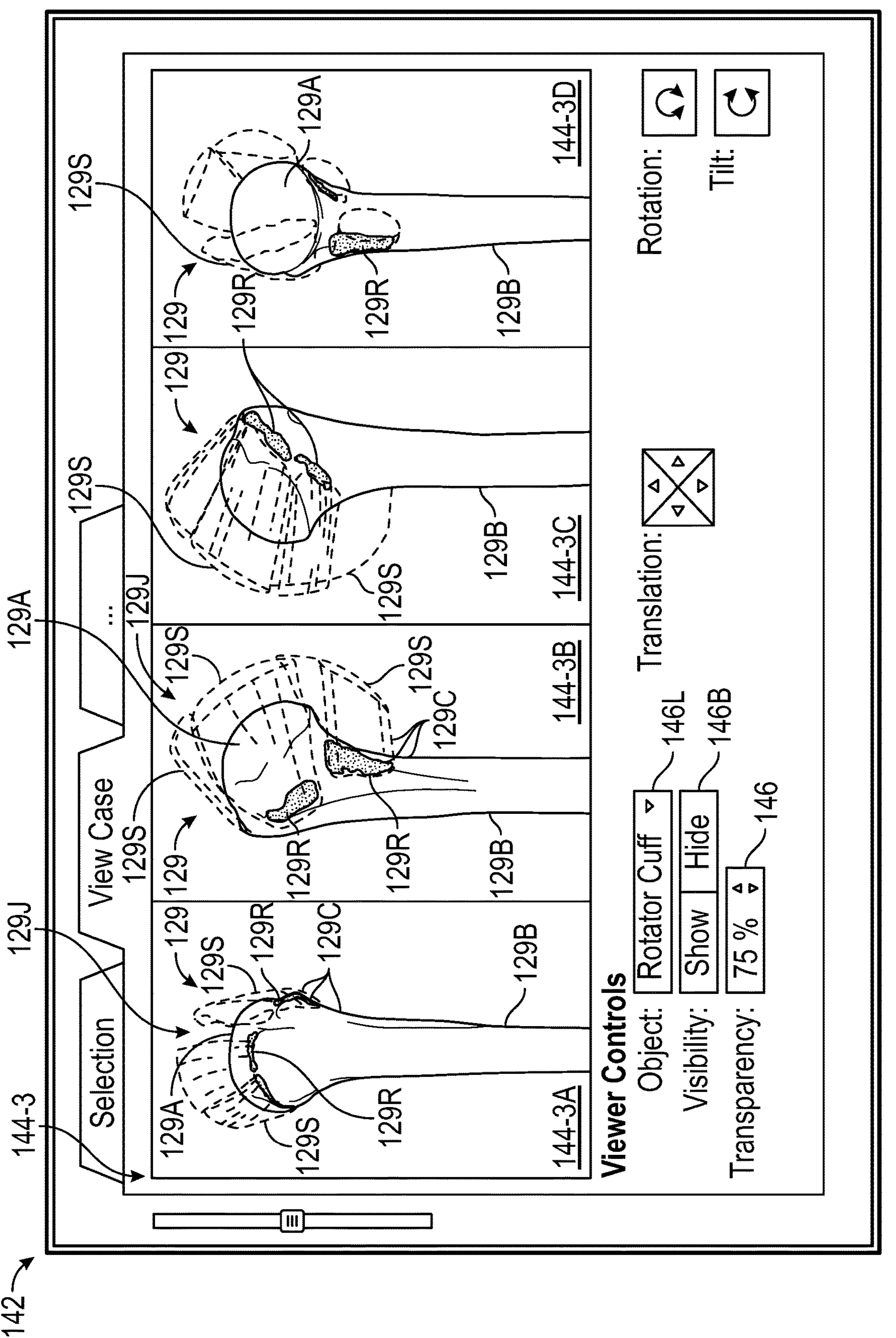
FIGS. 6-8 disclose the user interface of FIG. 2 including display windows depicting aspects of the virtual anatomical model of FIG. 5.
Figure 7:
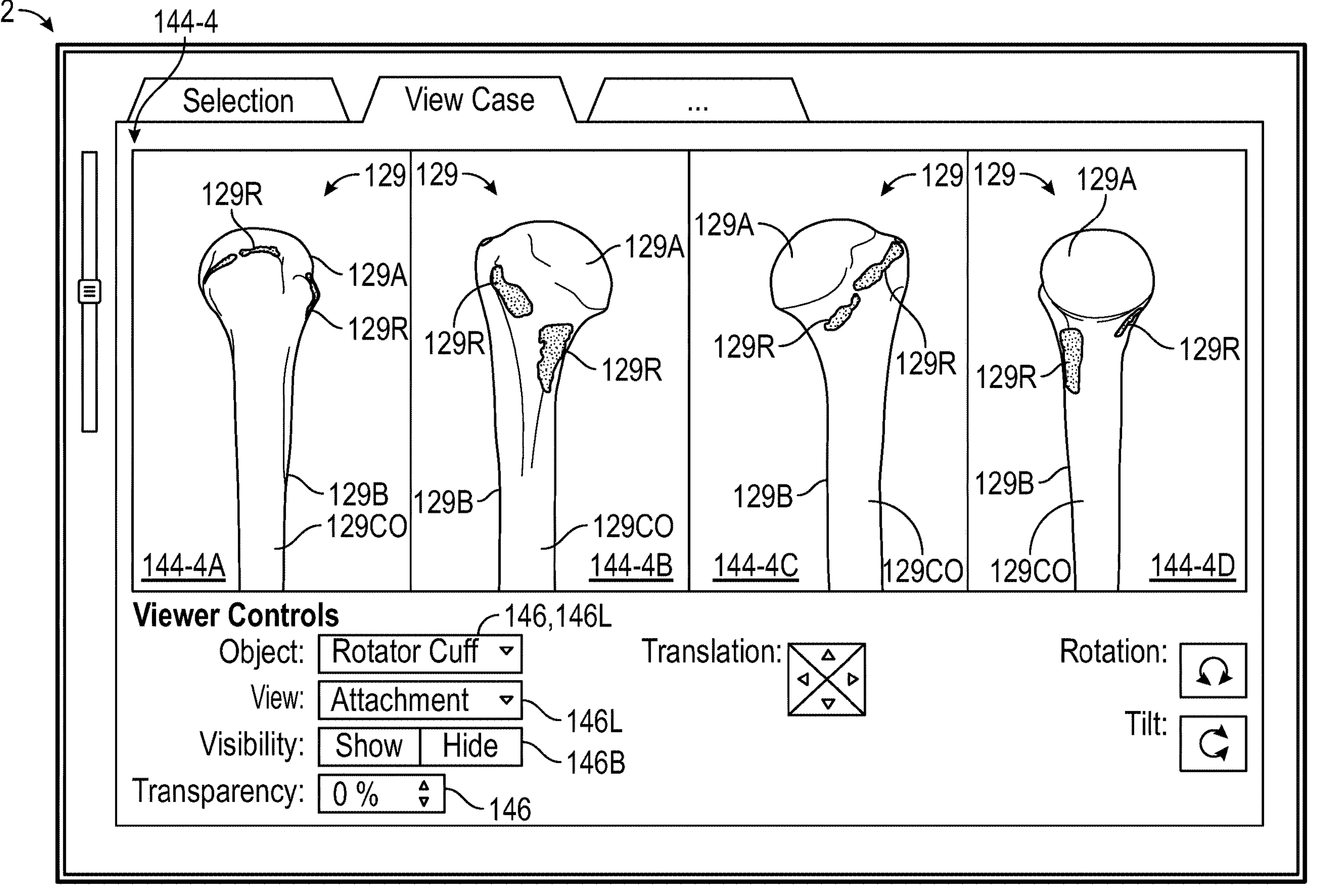

Referring to FIG. 6, with continuing reference to FIGS. 2 and 5, the surgeon or clinical user may interact with the user interface 142 to observe one or more aspects of the anatomical model 129. The user interface 142 may include one or more display windows 144-3, such as a third set of display windows 144-3A to 144-3D. The user may interact with a list 146L to select a specific portion of the soft tissue 129S, such as a rotator cuff. The display module 136 may be adapted to display one or more components 129C of the anatomical model 129, such as attachment regions 129R. The attachment regions 129R may be established along an interface between the bone volume 129B and the respective soft tissue volume 129S. The surgeon or clinical user may interact with one of the objects 146 to specify a transparency of one or more of these selected components 129C, such as one or more of the soft tissue volume 129S. Referring to FIG. 7, with continuing reference to FIGS. 2-3 and 6, the surgeon or clinical user may interact with the user interface 142 such as by interacting with one of the buttons 146B or another object 146 to select an attachment view within a list 146L such that the display module 136 may display a view of the attachment regions 129R with the soft tissue omitted (see, e.g., FIG. 6). The attachment regions 129R may be displayed in one or more display windows 144-4, such as a fourth set of display windows 144-4A to 144-4D.

Figure 8:
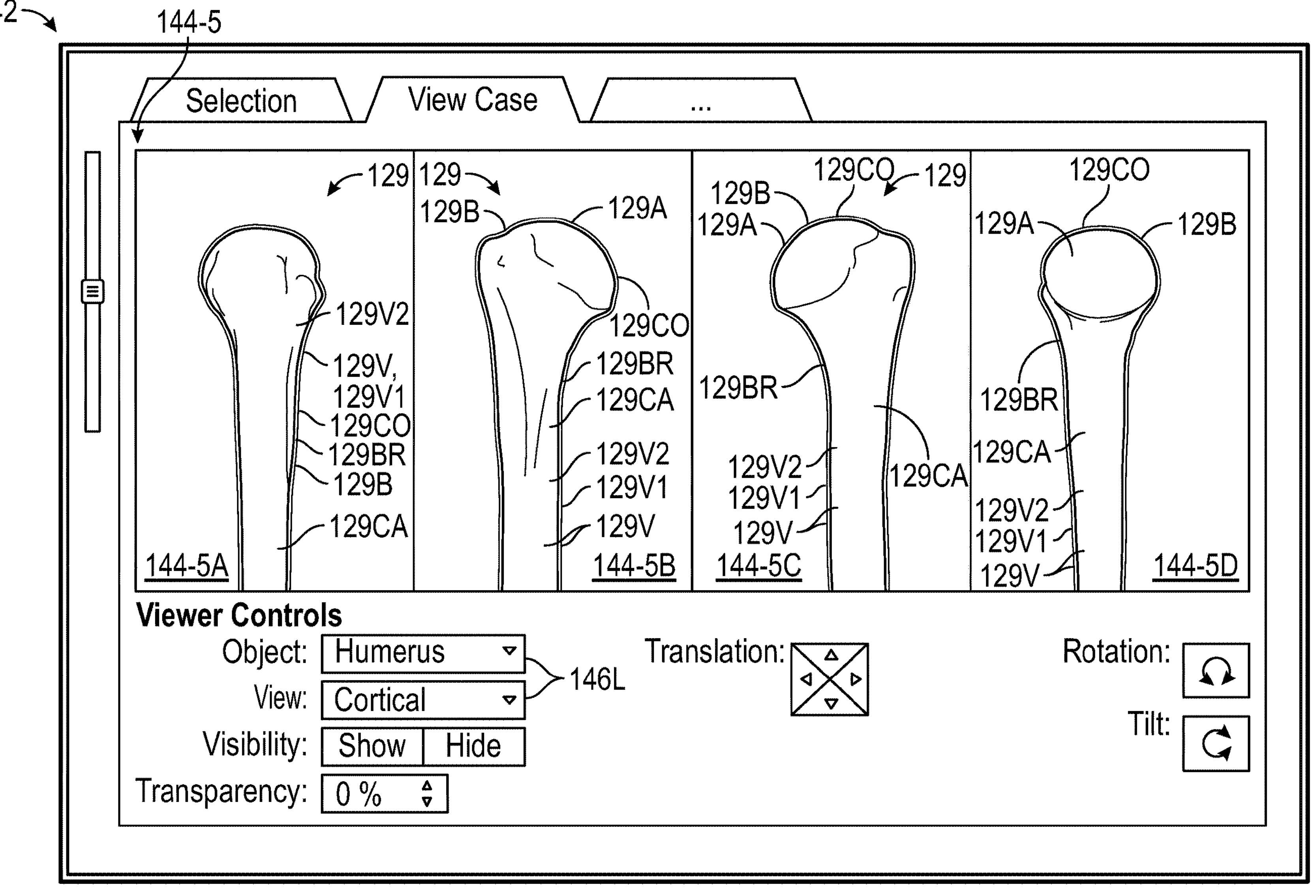

Referring to FIG. 8, with continuing reference to FIGS. 2, and 7, the surgeon or clinical user may interact with the user interface 142 to observe an isolated view of the bone volume 129B. The virtual anatomical model 129 may be displayed in one or more display windows 144-5, such as a set of fifth display windows 144-5A to 144-5D. The display module 136 may be adapted to display one or more aspects of the bone volume 129B, such as a cortical bone volume 129CO and/or cancellous bone volume 129CA. In implementations, the cortical bone volume 129CO may be displayed in phantom, and the cancellous bone volume 129CA may be displayed as a two-dimensional or three-dimensional solid.

The virtual anatomical model 129 may include one or more volumes 129V. One or more characteristics of the volumes 129V may be the same or may differ. The characteristics may include any of the characteristics disclosed herein, such as material composition and/or construction. In implementations, the volumes 129V may include a first volume 129V1 and a second volume 129V2. The first (e.g., cortical bone) volume 129V1 may be representative of cortical bone. The second (e.g., cancellous bone) volume 129V2 may be representative of cancellous bone. The cortical bone volume 129CO may establish the first volume 129V1. The cancellous bone volume 129CA may establish the second volume 129V2. The first volume 129V1 and the second volume 129V2 may include one or more characteristics that may be the same or may differ, such as material composition and/or construction. In implementations, the first and second volumes 129V1, 129V2 may differ in density. The different densities may be associated with different bone densities of an associated anatomy.

Figure 9:
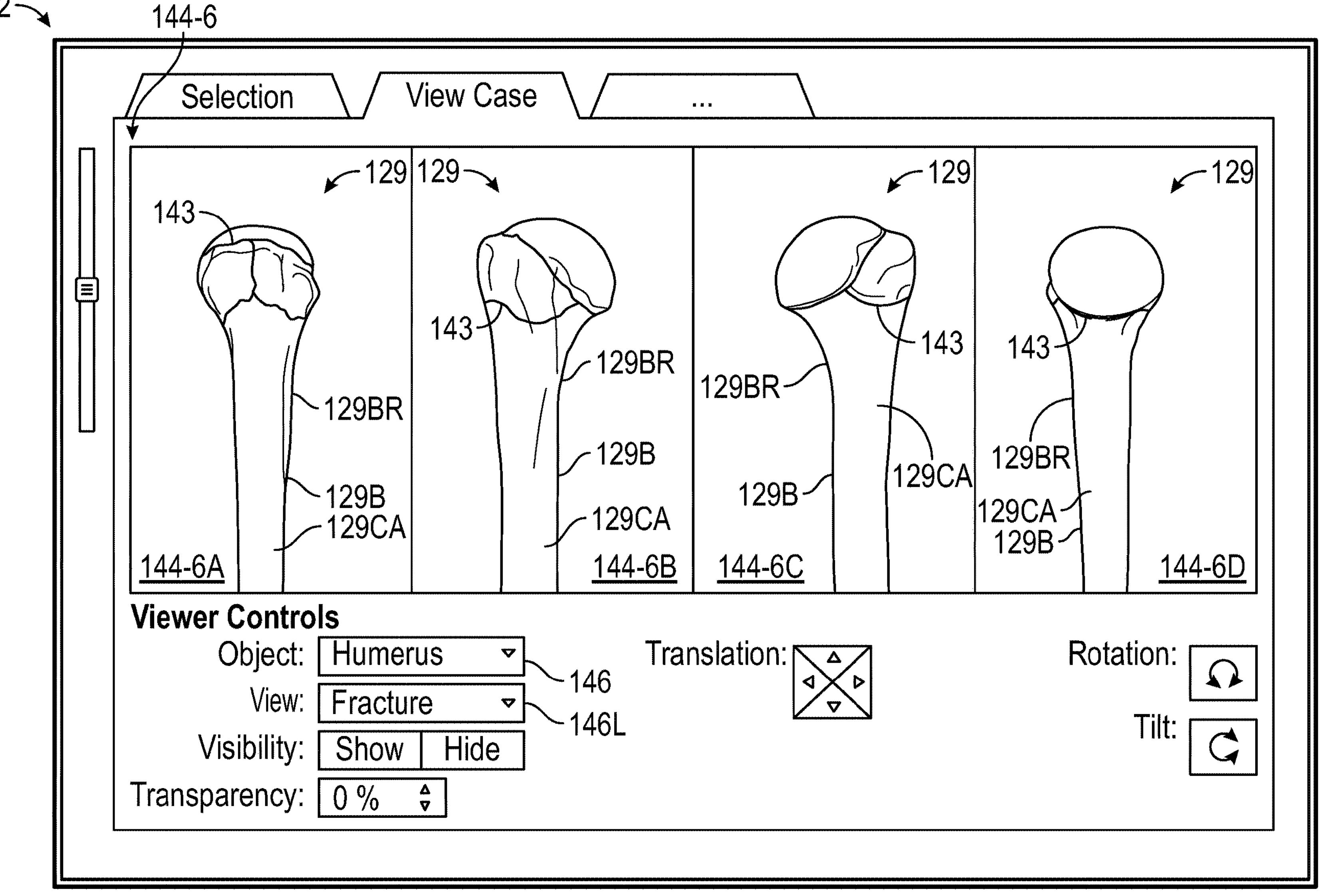
FIG. 9 discloses the user interface of FIG. 2 including display windows depicting a fracture pattern relative to the virtual anatomical model of FIG. 8.

Referring to FIG. 9, with continuing reference to FIGS. 2 and 8, one or more fracture patterns 143 may be selected or assigned to each virtual anatomical model 129. In implementations, the data module 135 may be configured to access one or more fracture patterns 143 from the database(s) 128 and/or another data location internal and/or external to the planning system 120. The spatial module 137 may be configured to generate the fracture pattern 143.

The fracture pattern 143 may extend along a boundary region 129BR between the first volume 129V1 and the second volume 129V2 (see, e.g., FIG. 8). The boundary region 129BR may be established along an interface between the cortical bone volume 129CO and the cancellous bone volume 129CA (see, e.g., FIG. 8). The boundary region 129BR may follow along an external surface of the cancellous bone volume 129CA and/or an internal surface of the cortical bone volume 129CO.

The surgeon or clinical user may interact with the user interface 142 to observe one or more aspects of the selected or assigned fracture pattern 143. The spatial module 137 may be adapted to arrange the assigned or selected fracture pattern 143 relative to the respective bone volume 129B. In the implementation of FIG. 9, the display module 136 may be adapted to display one or more views of the bone volume 129B and the associated fracture pattern 143 in one or more display windows 144, such as a sixth set of display windows 144-6A to 144-D. The surgeon or clinical user may interact with the one or more objects such as a list 146L to select a fracture view.

Figures 10A, 10B:
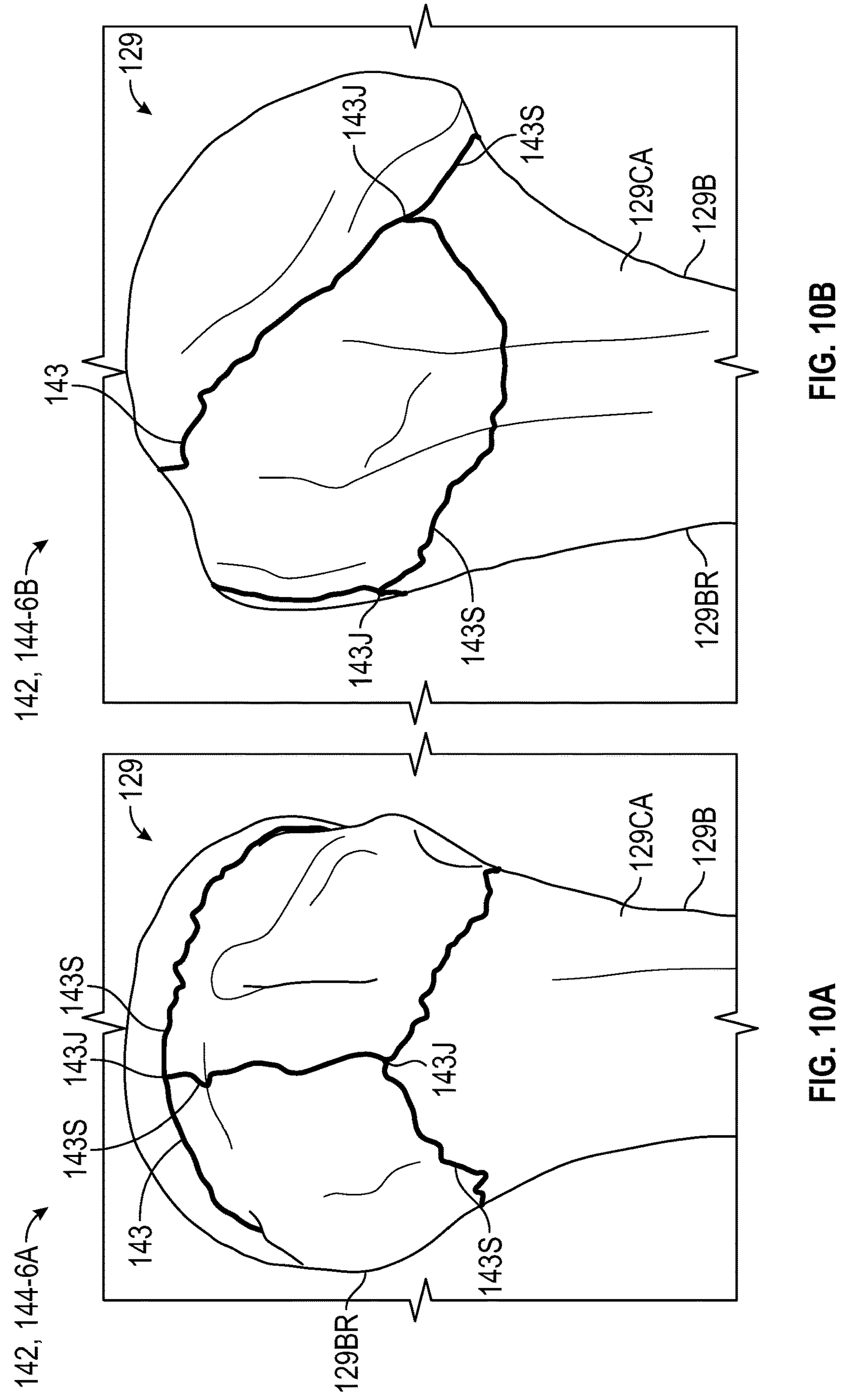
FIGS. 10A-10D disclose aspects of the fracture pattern of FIG. 9.

Referring to FIGS. 10A-10B, with continuing reference to FIGS. 2 and 9, aspects of the anatomical model 129 of FIG. 9 are shown. Each fracture pattern 143 may be generated automatically and/or in response to user interaction with the user interface 142. In implementations, the user may interact with the user interface 142 to manually specify a geometry of the fracture pattern 143.

Each fracture pattern 143 may include one or more segments 143S. The fracture pattern 143 may include two or more segments 143S that may be continuous or may be spaced apart from each other. Two or more of the segments 143S may meet at one or more junctions 143J. Each segment 143S may be a continuous loop and/or may be established between a pair of junctions 143J. In implementations, each of the segments 143S may extend along a surface of a portion of the bone volume 129B such as an external surface of the cancellous bone volume 129CA. In other implementations, one or more of the segments 143S may extend along a surface of the cortical bone volume 129CO (see, e.g., FIG. 8). Each of the segments 143S be a linear or non-linear path extending between two junctions 143J. In implementations, each of the segments 143S may include one or more undulations. The undulations may be representative of a fracture line observed in prior case(s) and/or hypothetical case(s) based on empirical data, parametric modeling, etc.

Figures 10C, 10D:
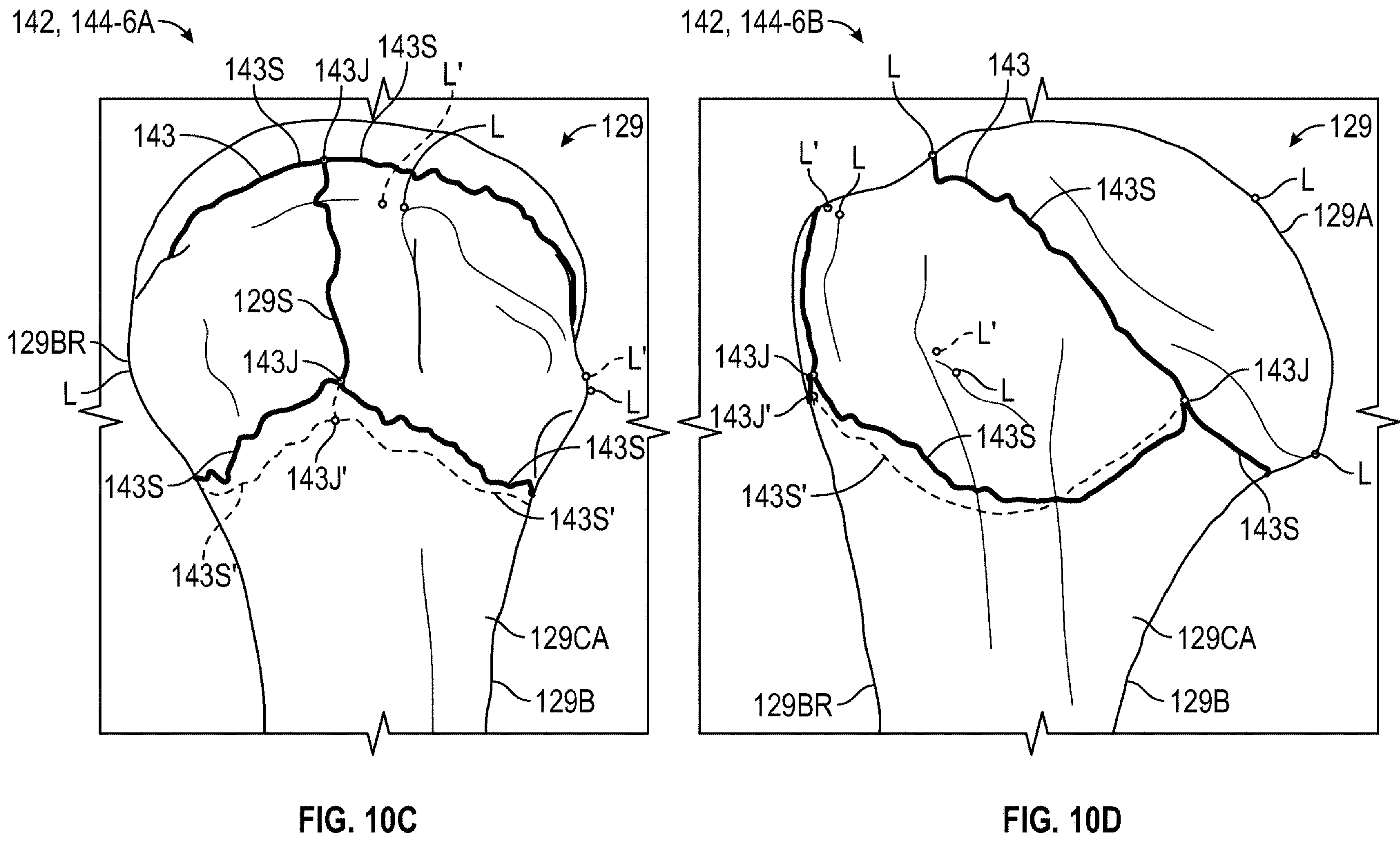

Referring to FIGS. 10C-10D, with continuing reference to FIGS. 2, 9 and 10A-10B, various techniques may be utilized to establish the fracture pattern 143. The spatial module 137 may be adapted to establish or identify one or more landmarks L relative to the bone volume 129B and/or another portion of the virtual anatomical model 129. In implementations, the comparison module 138 may be adapted to determine one or more landmarks L based on a comparison of the anatomical model 129 and one or more prior cases. In implementations, the surgeon or clinical user may interact with the display window 144, such as the display window 144-6A or 144-6B to adjust a position of one or more landmarks L (see, e.g., landmarks L'). The spatial module 137 may be adapted to adjust the position of one or more segments 143S in response to adjusting one or more associated landmarks L (see, e.g., segments 143S' and association junctions 143J').

Figure 11:
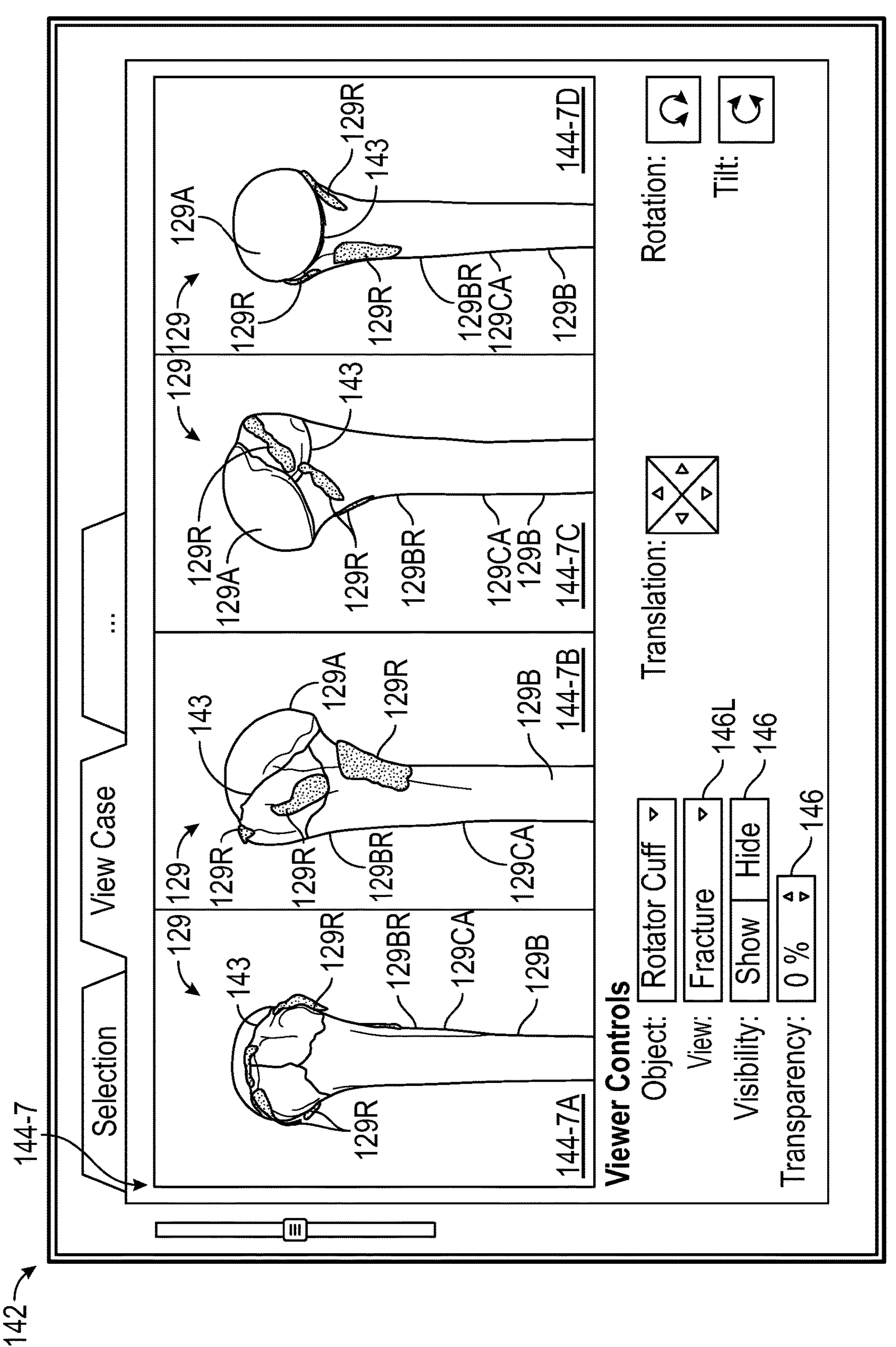
FIG. 11 discloses the user interface of FIG. 2 including display windows depicting the fracture pattern relative to the virtual anatomical model of FIG. 9.

The display model 136 may be adapted to display an isolated view of the fracture pattern 143 relative to the bone volume 129B and/or attachment regions 129R. In the implementation of FIG. 11, the surgeon or clinical user may interact with one or more display windows 144-7 such as a seventh set of display windows 144-7A to 144-7D, or another portion of the user interface 142 such as one of the lists 146L, to hide the representation of the cortical bone volume 129CO (see FIG. 8). Selectively hiding the cortical bone volume 129CO may assist the surgeon or clinical user in observing a relative position between the fracture pattern 143 and attachment region(s) 129R.

Figure 12:
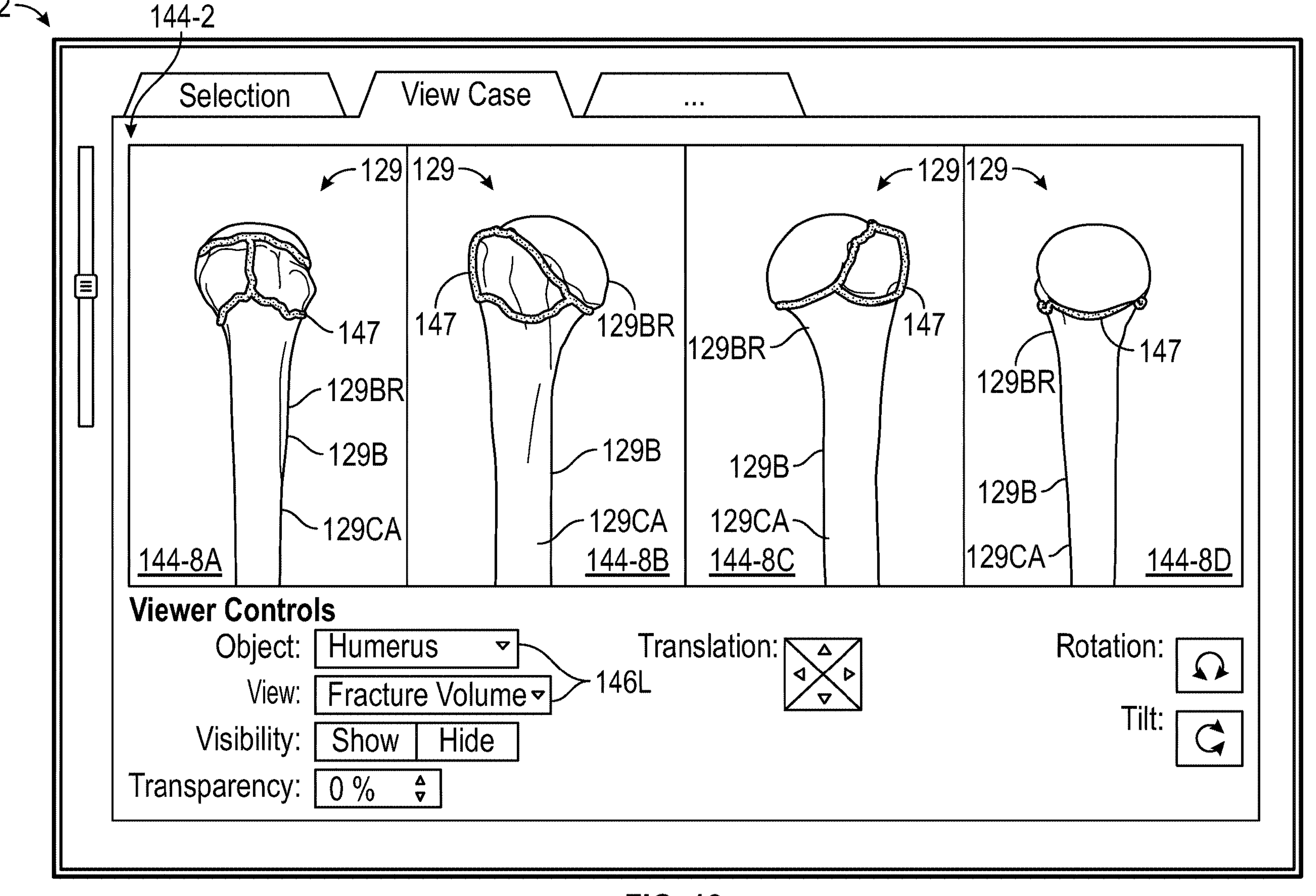
FIG. 12 discloses the user interface of FIG. 2 including display windows depicting a fracture volume relative to the virtual anatomical model of FIG. 9.

Referring to FIG. 12, with continuing reference to FIGS. 2 and 10, various techniques may be utilized to establish the fracture pattern 143 relative to the virtual anatomical model 129. The display module 136 may be configured to display the virtual anatomical model 129 in one or more display windows 144-8, such as an eighth set of display windows 144-8A to 144-8D.

The spatial module 137 may be configured to generate a virtual fracture volume 147, which may be associated with a fracture pattern 143. The virtual fracture volume 147 may substantially or generally follow a length of a respective fracture pattern 143 (see, e.g., FIGS. 10A-10D). For the purposes of this disclosure, the term "substantially" means ±10 percent of the stated relationship or value unless otherwise indicated. A configuration (e.g., definition) 145 (FIG. 2) may be established according to the virtual fracture volume 147.

Figure 13A:
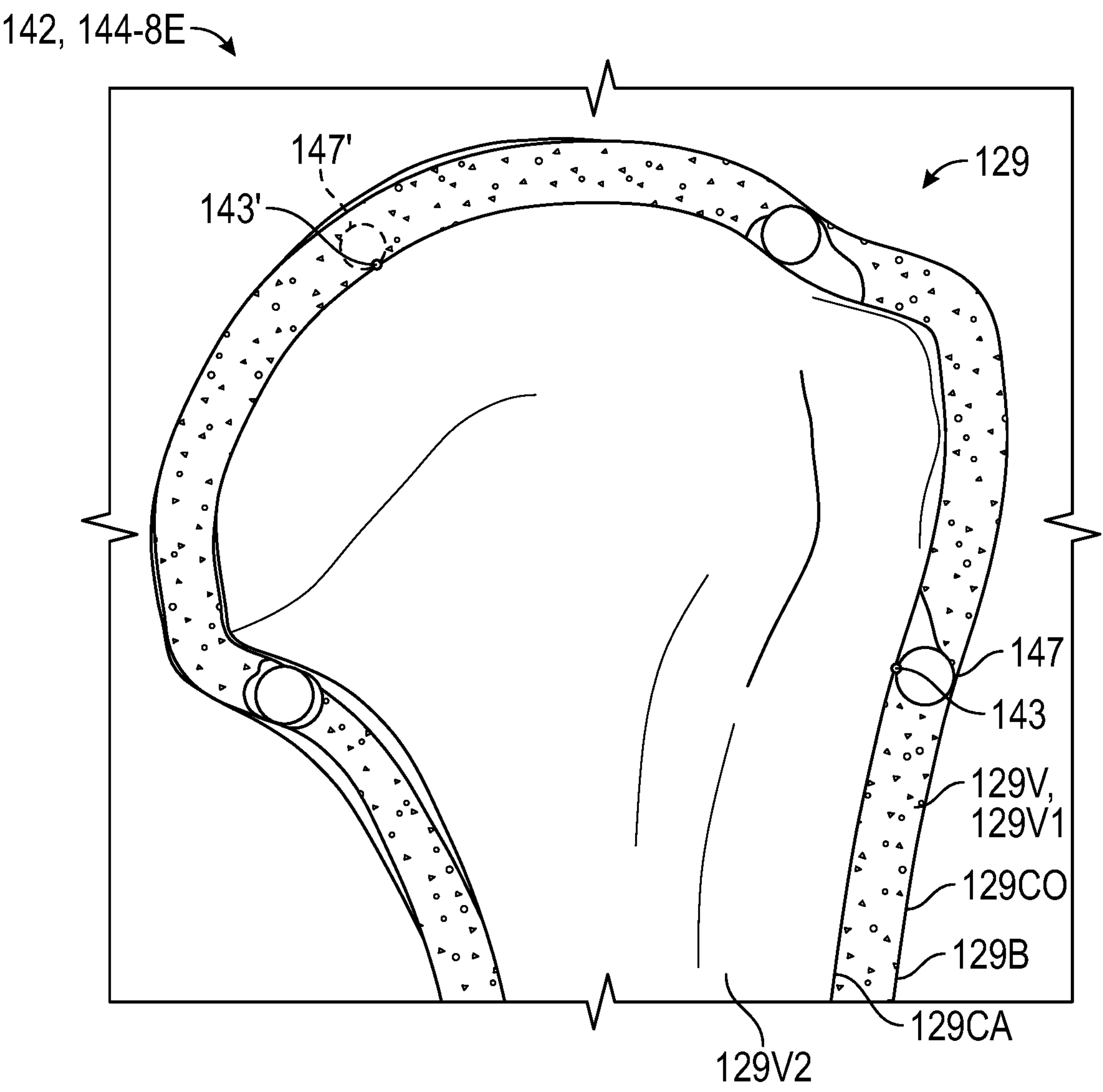
FIG. 13A discloses a sectional view of aspects of the fracture volume of FIG. 12.
Figure 13B:
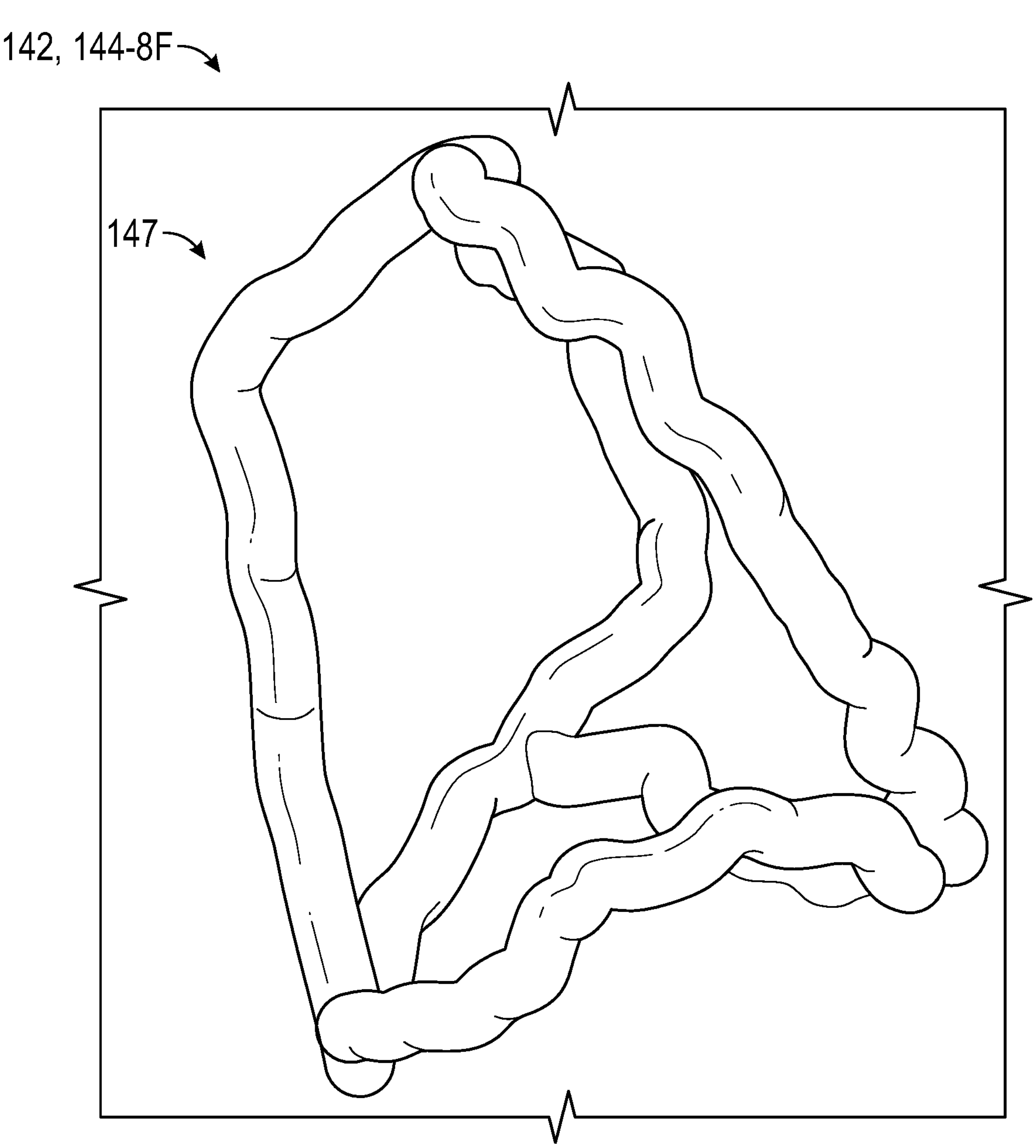
FIG. 13B discloses an isolated view of the fracture volume of FIG. 12.

Referring to FIG. 13A, with continuing reference to FIGS. 2 and 12, various techniques may be utilized to establish the virtual fracture volume 147. The display module 136 may be adapted to display the virtual fracture volume 147 in one or more display windows 144, such as display windows 144-8E, 144-8F (FIG. 13B). The virtual fracture volume 147 may be established by extruding a shape along a length of the fracture pattern 143. The display module 136 may be adapted to display the virtual fracture volume 147 in the display windows 144-8E, 144-8F. Various shapes may be utilized, such as a straight or curved line segment, an ellipse (e.g., circle), a polygon (e.g., rectangle) and/or complex shape. A geometry of the virtual fracture volume 147 may be selected to facilitate severing of a physical anatomical model. In implementations, the virtual fracture volume 147 may be dimensioned to span between an external surface of the cancellous bone volume 129CA and an external surface of the cortical bone volume 129CO. FIG. 13B discloses an isolated view of the virtual fracture volume 147 of FIG. 13A in the display window 144-8F. In other implementations, fracture volume 152' may be spaced apart from the external surface of the cortical bone volume 129CO (volume 152' shown in dashed lines in FIG. 13A).

The fracture volume 147 may have various constructions. The fracture volume 147 may be homogenous or may have two or more heterogenous regions. In implementations, the fracture volume 147 may be substantially hollow or may include one or more voids that may serve to weaken a localized region of an associated physical anatomical model.

Figure 14:
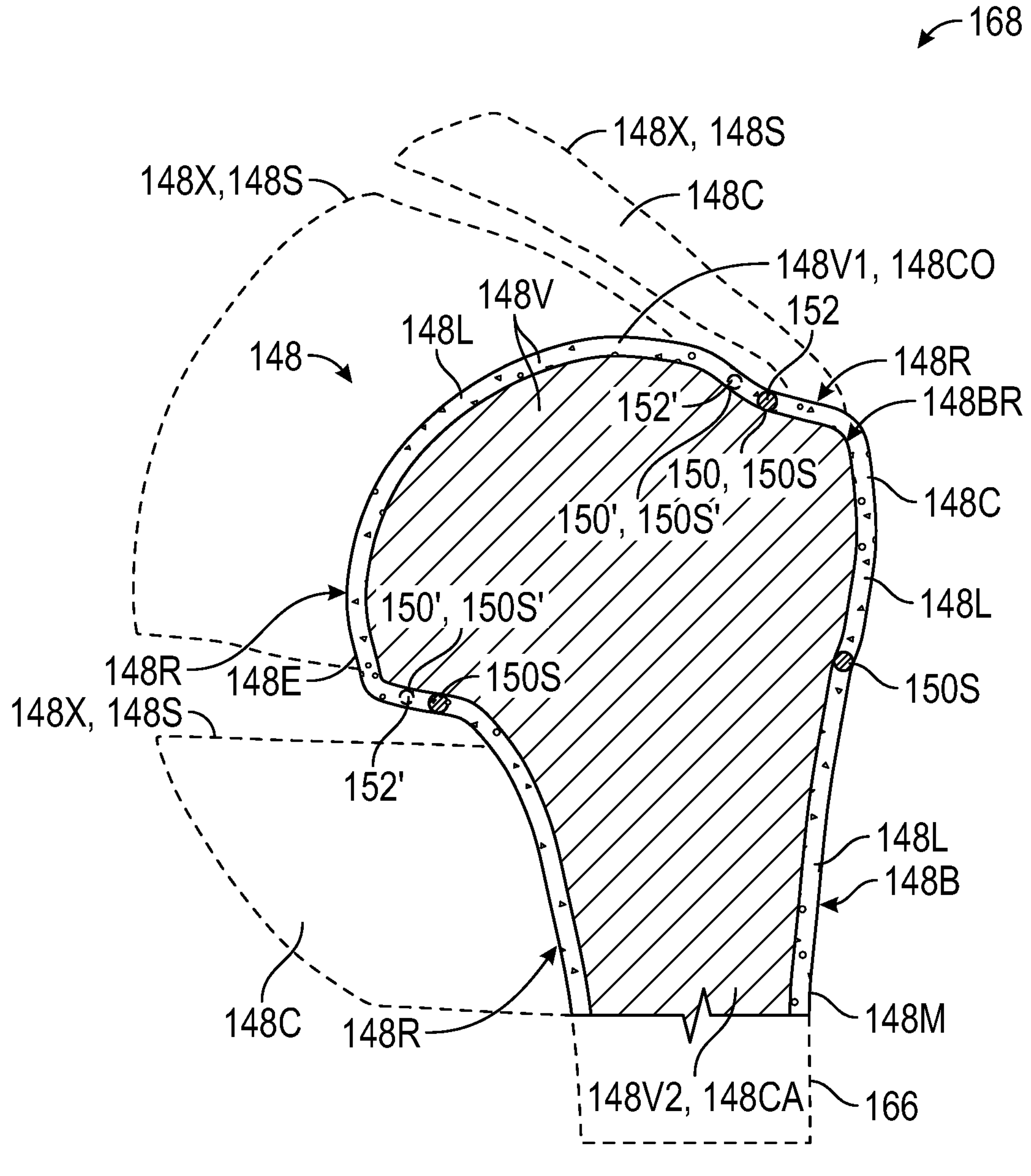
FIG. 14 discloses a sectional view of a physical anatomical model according to another implementation.
Figures 15A, 15B, 15C:
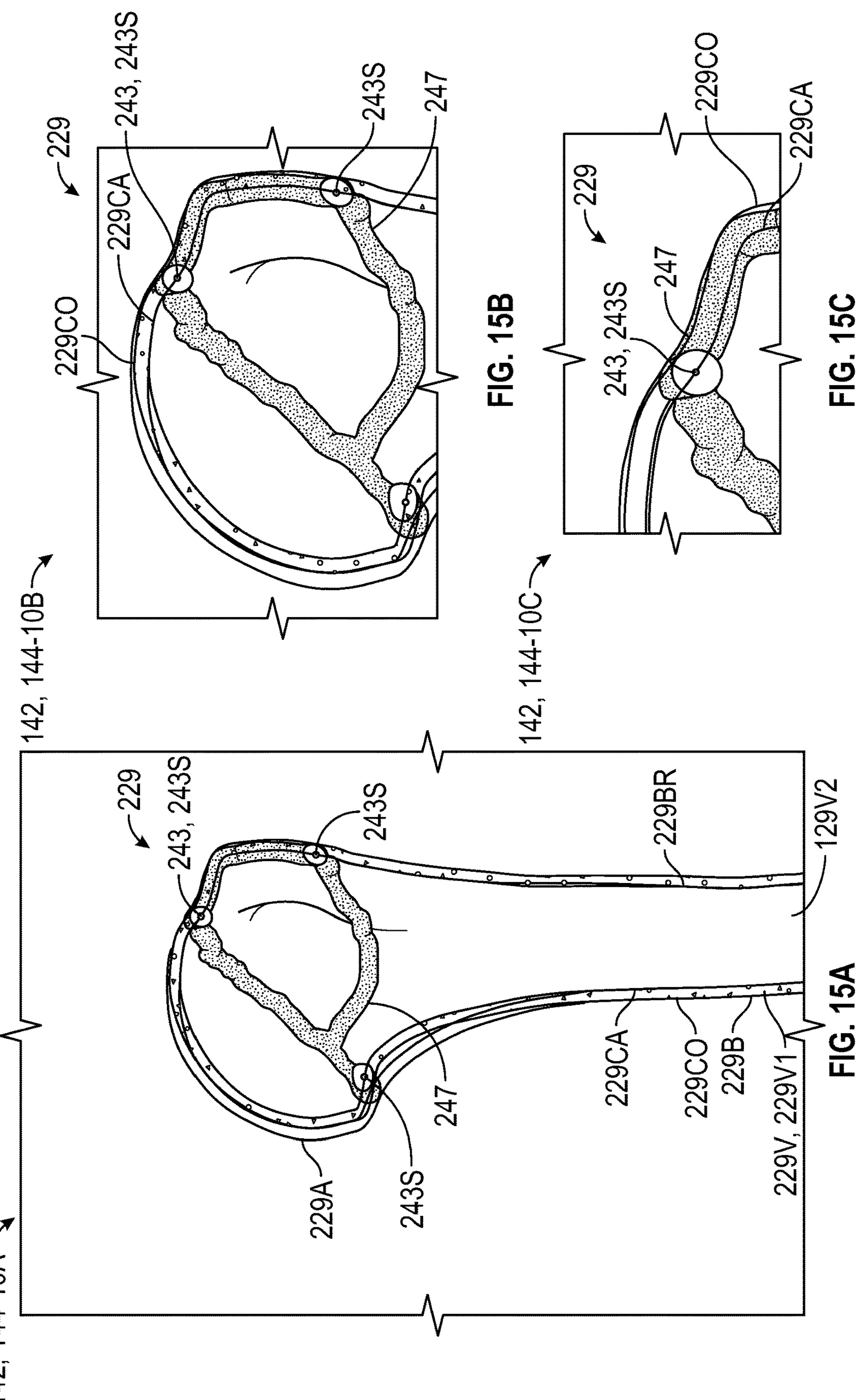
FIGS. 15A-15C disclose sectional views of a fracture volume relative to a virtual anatomical model.
Figures 16A, 16B, 16C:
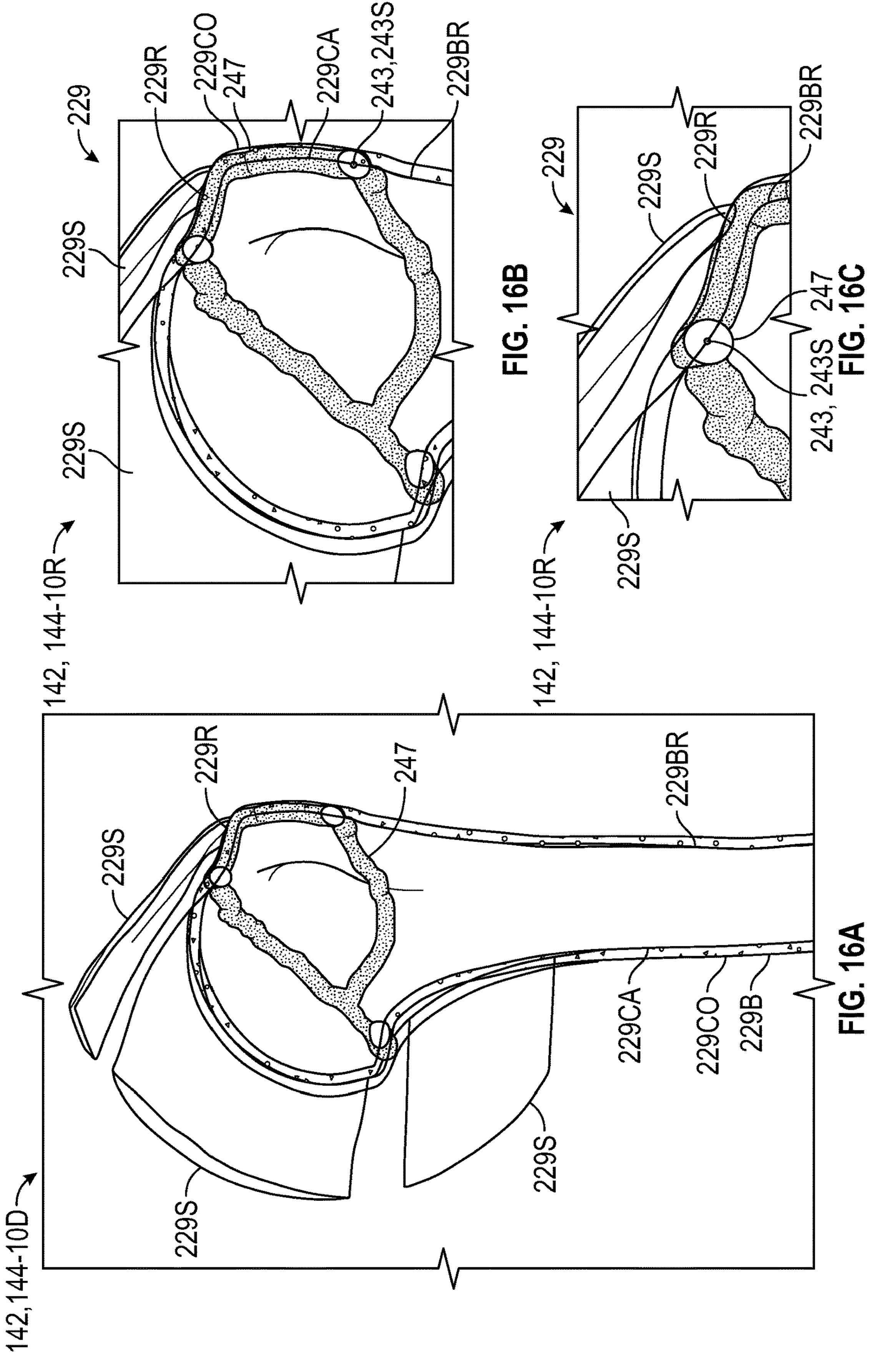
FIGS. 16A-16C disclose sectional views of the fracture volume relative to soft tissue volumes associated with the virtual anatomical model of FIGS. 15A-15C.

Referring to FIG. 14, with continuing reference to FIGS. 2 and 13A-13B, the virtual anatomical model 129 may be utilized to establish a physical anatomical model 148. The comparison module 138 may be configured to generate one or more configurations 145 (FIG. 2) associated with the virtual anatomical model(s) 129. The comparison module 138 may be adapted to generate the configuration 145 in response to specifying one or more parameters associated with a respective virtual anatomical model 129, including any of the parameters disclosed herein such as parameter(s) of the fracture classification scheme 141.

The configuration 145 may specify various information for forming an instance of an associated physical anatomical model 148, which may be based on a respective virtual anatomical model 129. The configuration 145 may include one or more files in a predetermined data structure or format. In implementations, the configuration 145 may include a coordinate set and/or other information such as material selection(s) associated with volume(s) of the physical anatomical model 148. Each physical anatomical model 148 may be formed utilizing various techniques, including any of the techniques disclosed herein such as rapid prototyping (e.g., printing) and other additive manufacturing techniques, casting, machining, etc.

The configuration 145 may specify a fracture path (e.g., fracture pattern) 150 that may be associated with a physical anatomical model 148. Each fracture path 150 may be established according to an assigned fracture pattern 143 such that the fracture patterns 143 may be reproducible. The configuration 145 may specify coordinate data and/or other information to establish the fracture path 150 according to the assigned fracture pattern 143. The configuration 145 may be generated such that the respective physical anatomical model 148 may be severable along the fracture path 150 to establish one or more fragments to establish a fragmentary state of the physical anatomical model 148 (see, e.g., fragments 348F of FIGS. 19-20).

The physical anatomical model 148 may include a main body 148M. For the purposes of this disclosure, the alphanumeric suffixes associated with each indicator of the virtual anatomical models are utilized in a like manner in describing similar aspects of the physical anatomical models unless otherwise indicated. The main body 148M may include an external surface 148E associated with an anatomical profile of a bone, including any of the bones disclosed herein. In implementations, the anatomical profile of the bone may be associated with a long bone, such as a humerus, femur or tibia. The physical anatomical model 148 may be secured to at least one fixture 166 to establish an assembly 168 (shown in dashed lines in FIG. 14).

The physical anatomical model 148 may include one or more physical components 148C. Each component 148C may be representative of an associated component 129C of the respective virtual anatomical model 129. The components 148C of the physical anatomical model 148 may include any of the components 129C of the respective virtual anatomical model 129, such as bone volume 148B. A representation of one or more of the components 129C may be omitted from the physical anatomical model 148 to provide tailored training to the surgeon or clinical user (e.g., different difficulty level, etc.).

The physical anatomical model 148 may include one or more extensions 148X (shown in dashed lines). Each extension 148X may extend from the external surface 148E of the main body 148M. One or more of the extensions 148X may be representative of respective soft tissue volume(s) 148S, including any of the soft tissue disclosed herein. The soft tissue volume 148S may be attached to the bone volume 129B at a respective attachment region 148R.

The main body 148M of the physical anatomical model 148 may include one or more volumes 148V. The main body 148M may include a first volume 148V1 and a second volume 148V2. The first volume 148V1 may establish the external surface 148E of the main body 148M. The first volume 148V1 may be representative of cortical bone. The second volume 148V2 may be representative of cancellous bone.

At least one fracture path 150 may be established along the physical anatomical model 148. The fracture path 150 may be established according to a predetermined fracture pattern 143 (see, e.g., FIG. 13A). The main body 148M may include the fracture path 150. The fracture path 150 may establish one or more localized regions 148L of the physical anatomical model 148. The fracture path 150 may divide the main body 148M into one or more localized regions 148L. The fracture path 150 may include one or more segments 150S. Each of the segments 150S may establish a loop about a respective localized region 148L (see also fracture volume 152 of FIG. 14). The external surface 148E along at least one of the localized regions 148L may be associated with an articular surface of a joint, including any of the joints and bones disclosed herein such as an articular surface of a humerus. Each extension 148X may extend from the external surface 148E of the main body 148M adjacent to one or more segments 150S of the fracture path 150.

The main body 148M of the physical anatomical model 148 may include at least one, or more than one, physical fracture volume 152. The physical fracture volume 152 may be established along the fracture path 150. The main body 148M may be severable along the fracture volume 152 to establish one or more fragments (see, e.g., fragments 348F of FIGS. 19-20). The physical fracture volume 152 may establish frangible connection(s) between the localized regions 148L and each other and/or the main body 148M of the physical anatomical model 148.

The fracture path 150 may extend along a boundary region 148BR between adjacent volumes 148V of the physical anatomical model 148, such as between the first volume 148V1 and second volume 148V2. The fracture volume 152 may be established along the fracture path 150 such that the fracture volume 152 may be at least partially embedded in one or more of the volumes 148V, such as the first volume 148V1 of the main body 148M. The main body 148M may be severable along the fracture volume 152 to establish the one or more fragments. In implementations, the physical fracture volume 152 may be spaced apart from the external surface of the main body 148M of the physical anatomical model 148 (see, e.g., fracture volume 152' of FIG. 13A).

The volumes 148V of the physical anatomical model 148 may have various properties. The first volume 148V1 may have a first property. The second volume 148V2 may have second property. The fracture volume 152 may have a third property. The first, second and/or third properties may be the same or may differ from each other. The first, second and third properties may include respective first, second and third material strengths. The second and/or third material strengths of the second volume 148V2 and fracture volume 152 may be less than the first material strength of the first volume 148V1. The first material strength may be representative of cortical bone. The second material strength may be representative of cancellous bone. The lesser material strength may establish relatively weaker region(s) in the physical anatomical model 148 to promote fragmentation of the physical anatomical model 148 in a reproducible manner. The fracture volume 152 may incorporate any of the materials disclosed herein, such as a silica-based material.

Referring to FIGS. 15A-15C and 16A-16C, with continuing reference to FIG. 2, in implementations the spatial module 137 may be adapted to extrude a virtual fracture volume 247 along one or more segments 243S of a respective fracture pattern 243. The display module 136 may be adapted to display the fracture volume 252 in one or more display windows 144 (e.g., display windows 144-10A to 144-10F). The virtual fracture volume 247 may span between an external surface of a cortical bone volume 229CO and an external surface of a cancellous bone volume 229CA. The fracture volume 247 may be extruded such that the fracture volume 252 may extend inwardly of the external surface of the cancellous bone volume 229CA. The fracture volume 247 may be at least partially surrounded by the cancellous bone volume 229CA. The display module 136 may be adapted to display the virtual fracture volume 247 and/or other aspects of the virtual anatomical model 229 in one or more display windows 144-10, such as a tenth set of display windows 144-10A to 144-10F. The display module 136 may be adapted to display the fracture volume 252 relative to soft tissue volumes 229S and/or attachment regions 229R (see, e.g., FIGS. 16A-16C).

Figure 17:
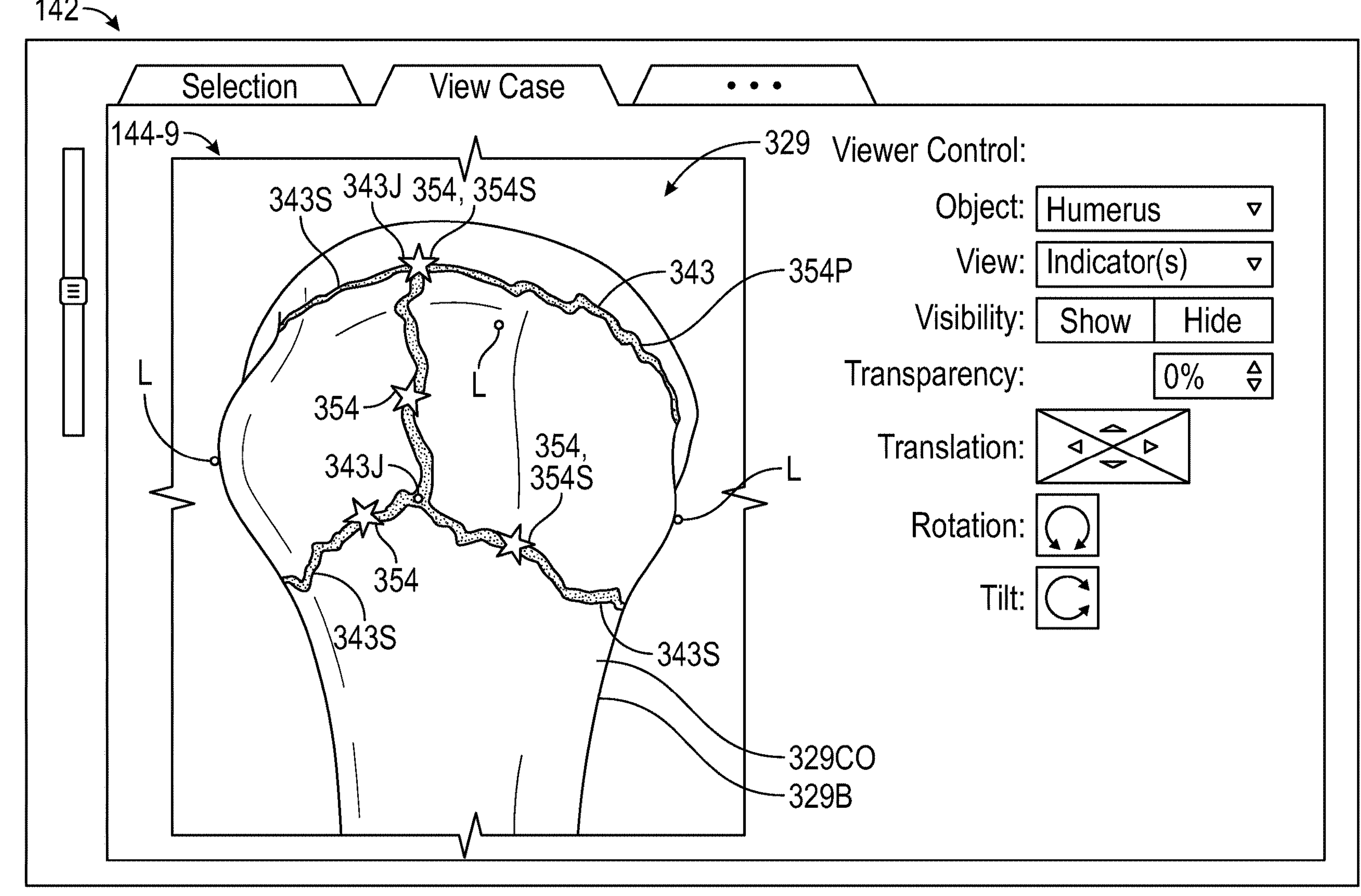
FIG. 17 discloses the user interface of FIG. 2 including a display window depicting virtual indicators relative to a virtual anatomical model.

Referring to FIG. 17, with continuing reference to FIG. 2, the planning system 120 may establish one or more virtual indicators 354 relative to a fracture pattern 343 and/or virtual anatomical model 329. Each of the virtual indicators 354 may be associated with the fracture pattern 343. The display module 136 may be adapted to display one or more of the virtual indicators 354 relative to the fracture pattern 343 in a ninth display window 144-9. Each of the virtual indicators 354 may serve as a visual aid and may provide information to the surgeon or clinical user relating to the fracture pattern 343.

Various virtual indicators 354 may be utilized to communicate clinically useful information to the surgeon or clinical user, including any of the indicators disclosed herein. Various techniques may be utilized to establish the virtual indicators 354. The comparison module 138 may be adapted to generate one or more virtual indicators 354 along or otherwise adjacent to one or more segments 343S and/or junctions 343J of the fracture pattern 343. The virtual indicators 354 may be generated automatically and/or in response to user interaction with the user interface 142 and/or another portion of the planning system 120. The indicators 354 may have various geometries, including various shapes and sizes. The indicators 354 may include one or more characteristics that may be distinct from anatomy, including different visual (e.g., shapes, patterns, colors, shades, etc.) and/or tactile (e.g., textures) characteristics. The indicators 354 may be established according to one or more visual or color schemes. In implementations, the indicators 354 may be assigned one or more artificial colors to establish a visual contrast from adjacent portion(s) of the virtual anatomical model 329, which may be assigned respective color(s) that may correspond to natural color(s) of respective portion(s) of the anatomy. The visual contrast may assist the surgeon in identifying the indicators 354. For the purposes of this disclosure, the term "natural" color means a color that substantially corresponds to an expected or actual color of the respective tissue, and the term "artificial" color means a color that does not naturally occur for the respective tissue. The artificial colors may include yellow, orange, red, green, blue, etc. The visual contrast may assist the surgeon in identifying physical instances of the indicators and any deviations from arranging any fragments relative to each other and/or a remainder of the main body of an associated physical anatomical model.

One or more of the virtual indicators 354 may include a shape (e.g., star) that may be dimensioned to span across a segment of the fracture pattern 343. One or more virtual indicators 354 may include an indication path 354P. The indication path 354P may substantially or generally follow a length of one or more segments 343S of the fracture pattern 343. One or more virtual indicators 354 may include a visual contrast (e.g., color, shade, etc.) between the fracture pattern 343 and an adjacent portion of the virtual anatomical model 329. The virtual indicators 354 may include one or more graduations (e.g., markings) that may be distributed along the length of the fracture pattern 143 (see, e.g., graduations 456G of FIGS. 21A-21C). In the implementation of FIG. 22, the virtual indicator 554 may include a silhouette 554S. The silhouette 554S may be associated with a perimeter of an orthopaedic implant securable to adjacent bone fragments (see, e.g., implant 1582 of FIGS. 42C-42D). The silhouette 554S may include one or more shapes representative of apertures dimensioned to receive respective fasteners to secure the implant to the bone (see, e.g., FIG. 42C).

In implementations, the physical anatomical model 448 may incorporate one or more electrical circuits to provide feedback to the surgeon or clinical user associated with registering the fragments 448F. The indication path 456P may include adjacent portions 456P1, 456P2. The adjacent portions 456P1, 456P2 may incorporate a conductive material such as copper or another metallic material. The adjacent portions 456P1, 456P2 may be coupled to an evaluation device 457 and may cooperate to establish a circuit 455. The evaluation device 457 may be configured to provide feedback to the surgeon or clinical user such as an audible signal, visual indicator (e.g., reading or graphic) or other indicator in response to establishing contact between the adjacent portions 456P1, 456P2.

Figure 18:
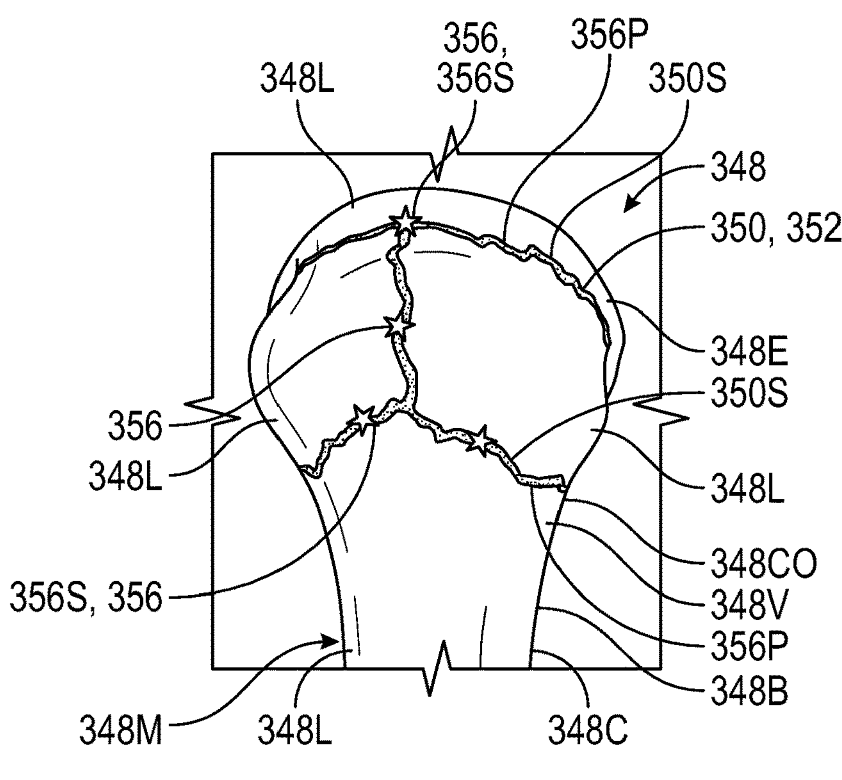
FIGS. 18-20 disclose various states of a physical anatomical model incorporating physical indicators relative to a fracture path and associated with the virtual anatomical model of FIG. 17.
Figure 19:
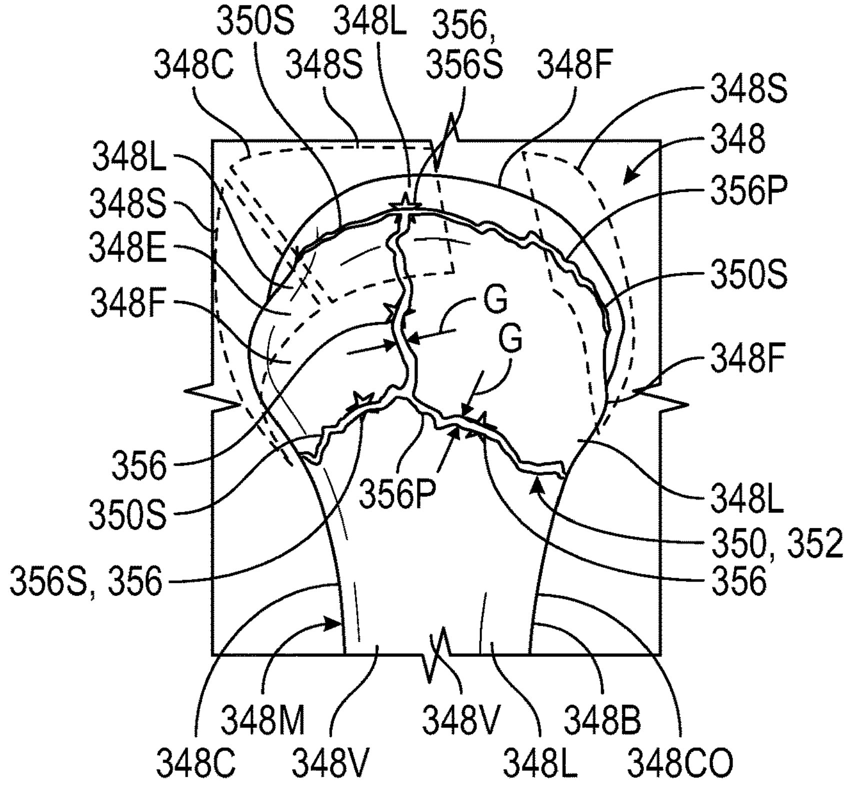
Figure 20:
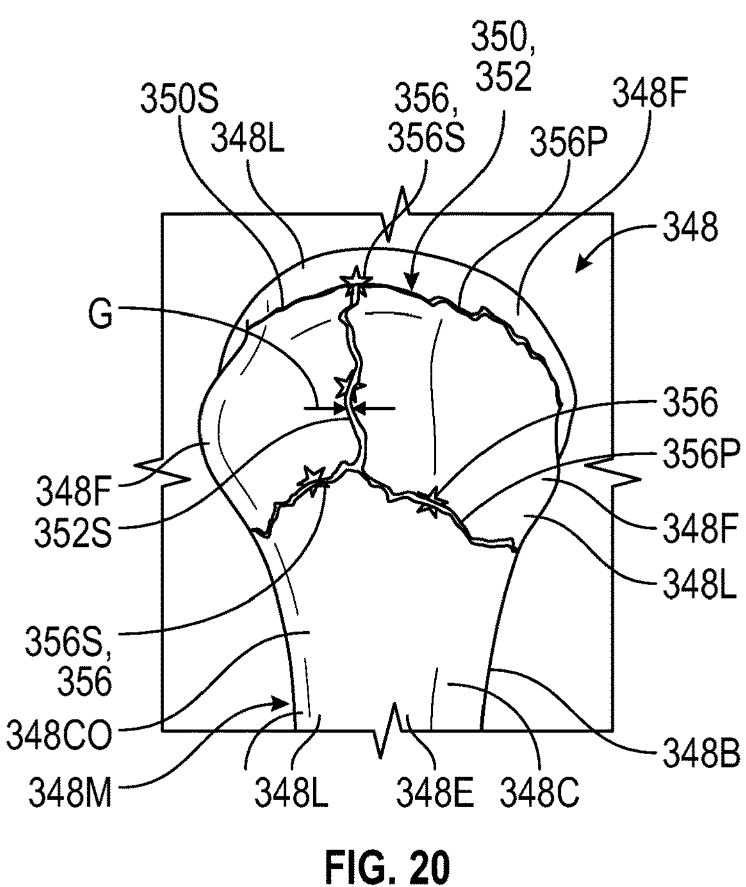

Referring to FIGS. 18-20, with continuing reference to FIGS. 2 and 17, various states of a physical anatomical model 348 are disclosed. FIG. 18 may be associated with a first (e.g., initial, intact or pre-fragmentary) state of the physical anatomical model 348. FIG. 19 may be associated with a second (e.g., fragmentary) state of the physical anatomical model 348 of FIG. 18. FIG. 20 may be associated with a third (e.g., fragmentary) state of the physical anatomical model 348 of FIG. 18.

The main body 348M and/or other portions of the physical anatomical model 348 may include one or more physical indicators 356. Each of the virtual indicators 354 may be associated with a physical indicator 356 incorporated into the physical anatomical model 348. Each physical indicator 356 may be associated with a respective virtual indicator 354. A configuration 145 (FIG. 2) associated with the respective physical anatomical model 348 may specify coordinate data and other characteristics associated with the virtual indicators 354 to establish one or more of the physical indicators 356. Each physical indictor 356 may be established along an external surface and/or in a thickness of the physical anatomical model 348. Each of the physical indicators 356 may be associated with the fracture path 350 and/or fracture volume 352.

In the implementations of FIGS. 18-20, one or more physical indicators 356 may include a shape 356S that may span across a segment of the fracture path 350. The shape 356S may be established along the external surface 348E of the main body 348M. The shape 356S may span between at least two of the localized regions 348L. The physical indicators 356 may include one or more indication paths 356P. Each indication path 356P may substantially or generally follow a length of one or more segments 350S of the fracture path 350. The indication path 356P may be established along the external surface 348E of the main body 348M.

Figure 21A:
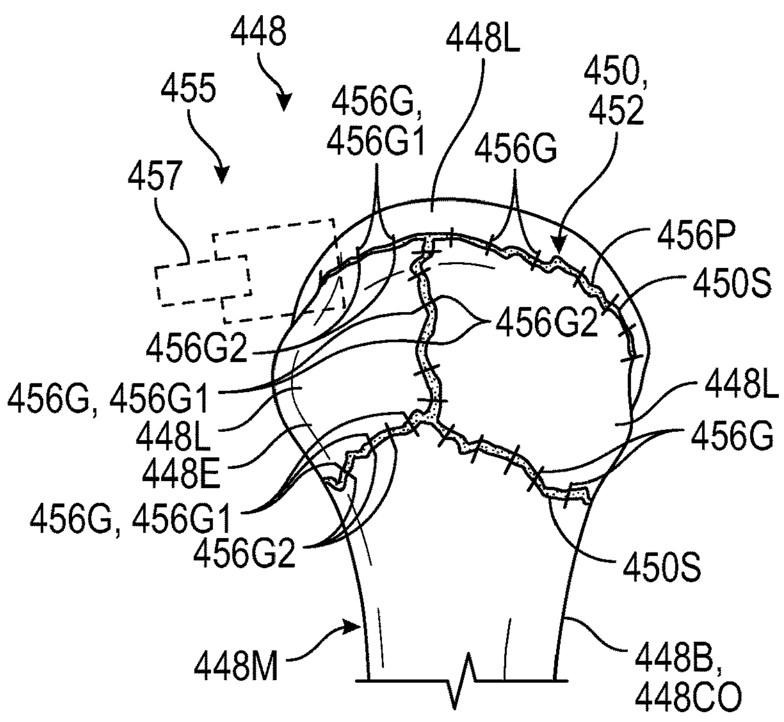
FIGS. 21A-21C disclose various states of a physical anatomical model incorporating physical indicators relative to a fracture path.
Figure 21B:
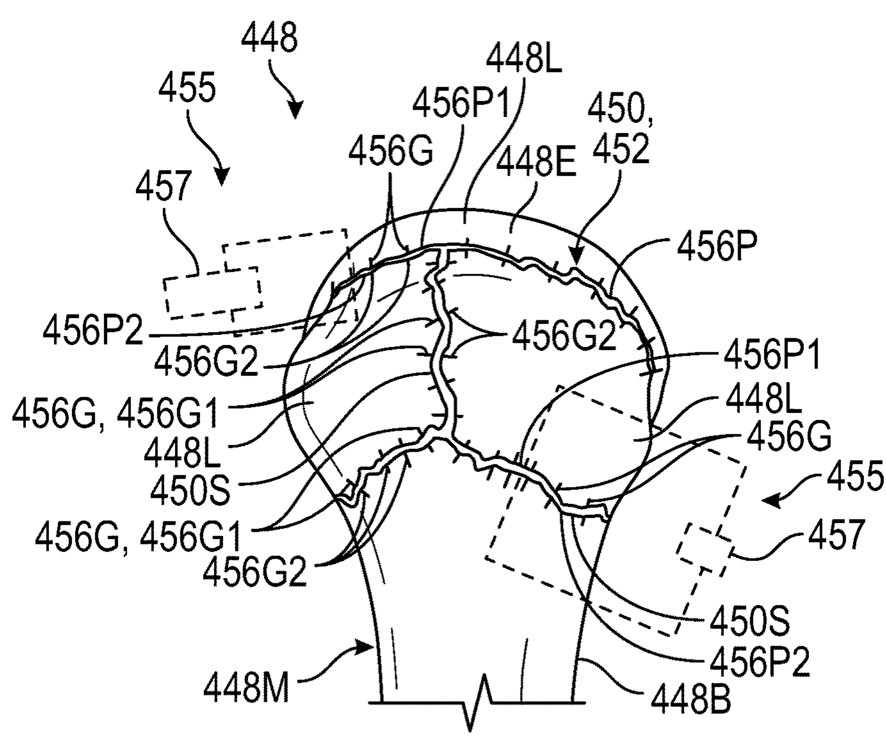
Figure 21C:
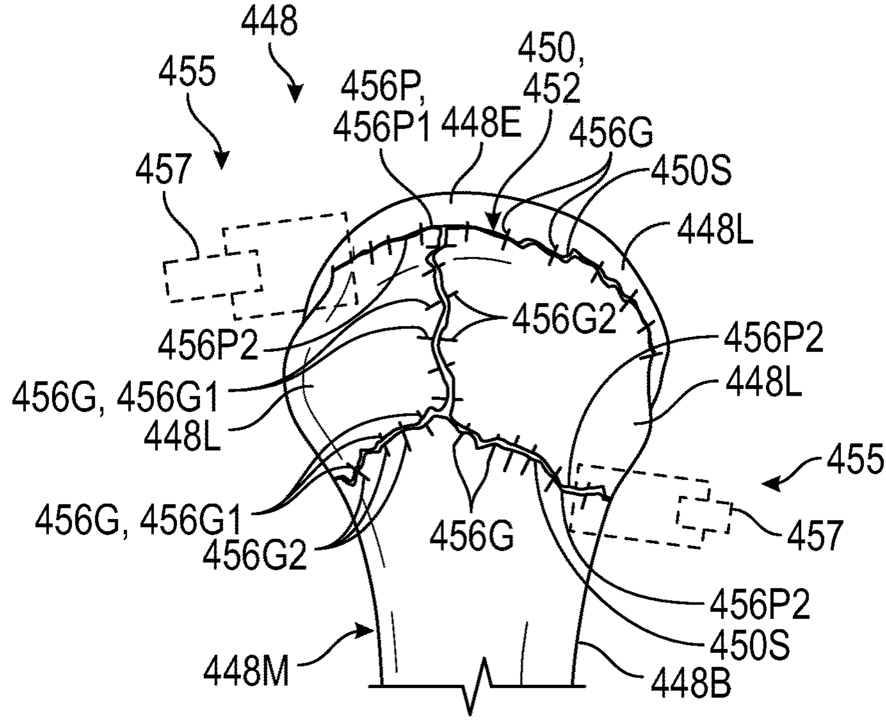

One or more physical indicators 356 may include a visual contrast between the fracture path 350 and an adjacent portion of the physical anatomical model 348. The indicators 356 may include a visual contrast between the main body 348M and the fracture volume 352. In implementations, the visual contrast may be established by marking(s) having color(s) and/or shade(s) that may differ from an adjacent portion of the physical anatomical model 348. In implementations, the shape(s) 356S and/or indication path(s) 356P may establish a visual contrast with adjacent portions of the physical anatomical model 348. The physical anatomical model 348 may additionally and/or alternatively incorporate other physical indicators 356. In the implementation of FIGS. 21A-21C, one or more physical indicators 456 may include one or more graduations (e.g., markings) 456G. The graduations 456G may be distributed along a length of one or more segments 450S of the fracture path 450. The graduations 456G may facilitate evaluation of surgeon repair, including relative alignment between adjacent fragments 448F. Each graduation 456G may extend across the fracture path 450.

The main body 348M of the physical anatomical model 348 may be severable along the fracture path 350 to establish one or more fragments 348F associated with a fragmentary state of the physical anatomical model 348 (see, e.g., FIGS. 19-20). Each fragment 348F may be associated with a respective one of the localized regions 348L or a remainder of the main body 348M of the physical anatomical model 348. The fragments 348F may include respective portions of a bone volume 348B. In implementations, soft tissue volume(s) 348S may be attached to the fragment(s) 348F (shown in dashed lines in FIG. 19). The fracture path 350 and/or physical fracture volume 352 may be dimensioned such that each of the fragments 348F may include portion(s) of the volume(s) 348V, such as a portion of the first volume 348V1 and/or a portion of the second volume 348V1 (see, e.g., volumes 1429V1', 1429V2' of the virtual anatomical model 1429' of FIG. 41).

The surgeon or clinical user may interact with the physical anatomical model 348 to register the fragments 348F relative to each other and/or another portion (e.g., remainder) of the physical anatomical model 348. The surgeon or clinical user may utilize one or more of the physical indicators 356 to obtain feedback regarding a fit of the arrangement of the fragments 348F relative to initial state of the physical anatomical model 348, such as relative to the volume of the physical anatomical model 348 prior to creation of the fragments 348F (see, e.g., FIG. 18).

The physical indicators 356 may provide an indication of alignment and/or distance of each fragment 348F relative to adjacent fragment(s) 348F and/or another portion of the physical anatomical model 348. In the implementation of FIG. 19, one or more indicators 356 may indicate a physical gap G established between adjacent portions of the respective indicator 356. The physical gap G may indicate deviation from a complete registration of the fragments 348F relative to the pre-fragmentary state of the physical anatomical model 348 (see, e.g., FIG. 18). In the implementation of FIG. 20, the fragments 348F may be registered in close proximity to one another such that any physical gap(s) G between portions of the indicators 456 may be reduced relative to the arrangement of FIG. 19.

In the implementation of FIGS. 21A-21C, graduations 456G may be utilized to facilitate evaluation of repair of a fragmentary state of the physical anatomical model 448. Each of the graduations 456G may include segments 456G1, 456G2 established on opposite sides of the fracture path 450. The segments 456G1, 456G2 may be associated with localized volumes 448L on opposite sides of the fracture path 450. Severing the physical anatomical model 448 may occur to establish fragments 448F associated with respective localized volumes 448L. Severing the physical anatomical model 448 may occur such that the segments 456G1, 456G2 may be associated with adjacent fragments 448F. The surgeon may register or otherwise position the fragments 448F such that the segments 456G1, 456G2 of the graduation 456G may be misaligned, substantially aligned or otherwise adjacent to each other to provide visual feedback to the surgeon in relation to the respective localized volumes 448L prior to fragmentation of the physical anatomical model 448. A predetermined threshold may be associated with the graduations 456G. Registration of the fragments 456G may be evaluated based on alignment of the segments 456G1, 456G2 of the graduation 456G being below, meeting or exceeding the predetermined threshold.

In the implementation of FIG. 22, the physical indicator 556 may include a silhouette 556S. The silhouette 556S may be associated with a perimeter of an orthopaedic implant securable to adjacent bone fragments (see, e.g., implant 1582 of FIG. 42C). The silhouette 556S may include one or more shapes representative of apertures dimensioned to receive respective fasteners to secure the implant to the bone.

Referring to FIGS. 23 and 24, with continuing reference to FIG. 2, other techniques may be utilized to establish the fracture patterns of the virtual anatomical models and associated fracture paths of the physical anatomical models. The planning system 120 may be adapted to establish a fracture path 643 including one or more voids 643V. The voids 643V may establish perforations in an adjacent volume 629V of the virtual anatomical model 629. The voids 643V may terminate at a boundary region 629BR between adjacent volumes 629V1, 629V2. The volume 629V1 may be established by a cortical bone volume 629CO. The volume 629V2 may be established by a cancellous bone volume 629CA.

One or more physical voids 650V may be established in a physical anatomical model 648 along or otherwise adjacent to the fracture path 650. The voids 650V may be associated with the respective voids 643V. The voids 650V may be printed together or otherwise formed with adjacent portions of the physical anatomical model 648. The voids 650V may facilitate breakage along the fracture path 650 of the physical anatomical model 648 to establish one or more fragments.

Figures 25, 26:
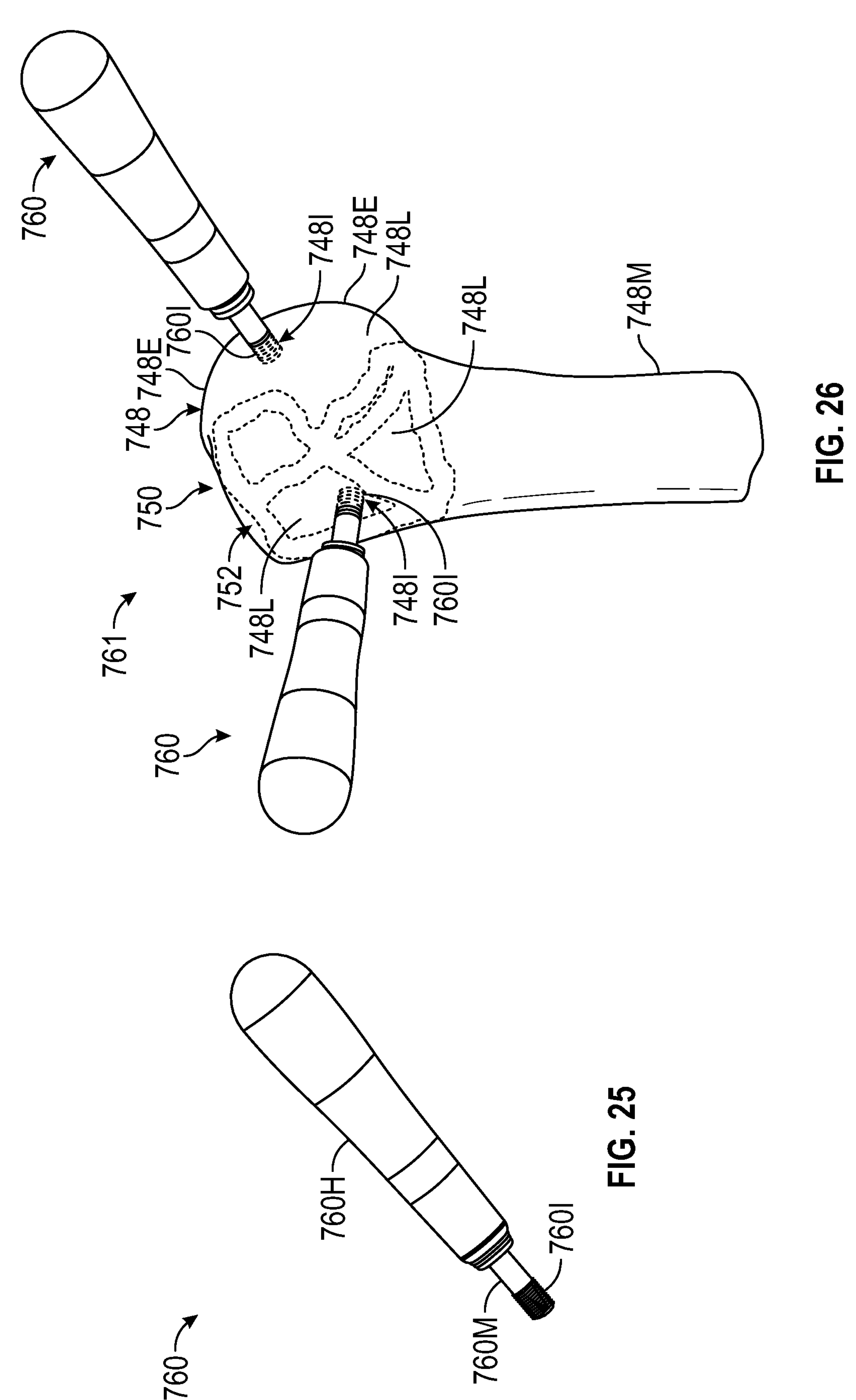
FIG. 25 discloses a perspective view of a fracture tool according to an implementation.
FIG. 26 discloses the fracture tool of FIG. 25 positioned relative to a physical anatomical model.

Various techniques may be utilized to establish a fragmentary state of the physical anatomical model. Referring to FIG. 25, a fracture tool 760 for engaging a physical anatomical model is disclosed. The fracture tool 760 may include a main body 760M and an interface portion 7601. A handle 760H may extend from the main body 760M. In implementations, the main body 760M may include an elongated shaft. The handle 760H may be manipulated by the surgeon or clinical user to position the fracture tool 760 relative to a physical anatomical model.

Referring to FIG. 26, with continuing reference to FIG. 25, the interface portion 7601 may be adapted to engage a physical anatomical model 748. The physical anatomical model 748 and fracture tool 760 may establish an orthopaedic system 761. The surgeon or clinical user may be provided with the fracture tool 760 and one or more physical anatomical models 748 in a kit. The physical anatomical models 748 may be the same or may differ. Each physical anatomical model 748 may be established according to any of the techniques disclosed herein.

The physical anatomical model 748 may include a main body 748M having at least one fracture path 750. The physical anatomical model 748 may include a fracture volume 752 established along the respective fracture path 750. The fracture tool 760 may be adapted to cause the main body 748M of the physical anatomical model 748 to sever along the fracture path 750 and/or fracture volume 752 to establish one or more fragments 748F (FIG. 27E).

Various techniques may be utilized to establish an engagement between the physical anatomical model 748 and fracture tool 760. The physical anatomical model 748 may include one or more interfaces 7481. The interfaces 7481 may extend inwardly from an external surface 748E of the physical anatomical model 748. Each interface 7481 may be associated with a localized region 748L of the physical anatomical model 748. Each interface 7481 may be established along, adjacent to, or spaced apart from the fracture path 750 and associated fracture volume 752. The interface portion 7601 may be insertable in each of the interfaces 7481 of the physical anatomical model 748, although an opposite arrangement may be utilized. The interface portion 7601 may be dimensioned to interfit with a selectable one of the interfaces 7481. In implementations, the interface portion 7601 and interface 7481 may include a plurality of threads that cooperate with each other to establish a connection between the fracture tool 760 and physical anatomical model 748.

Figures 27A, 27B, 27C:
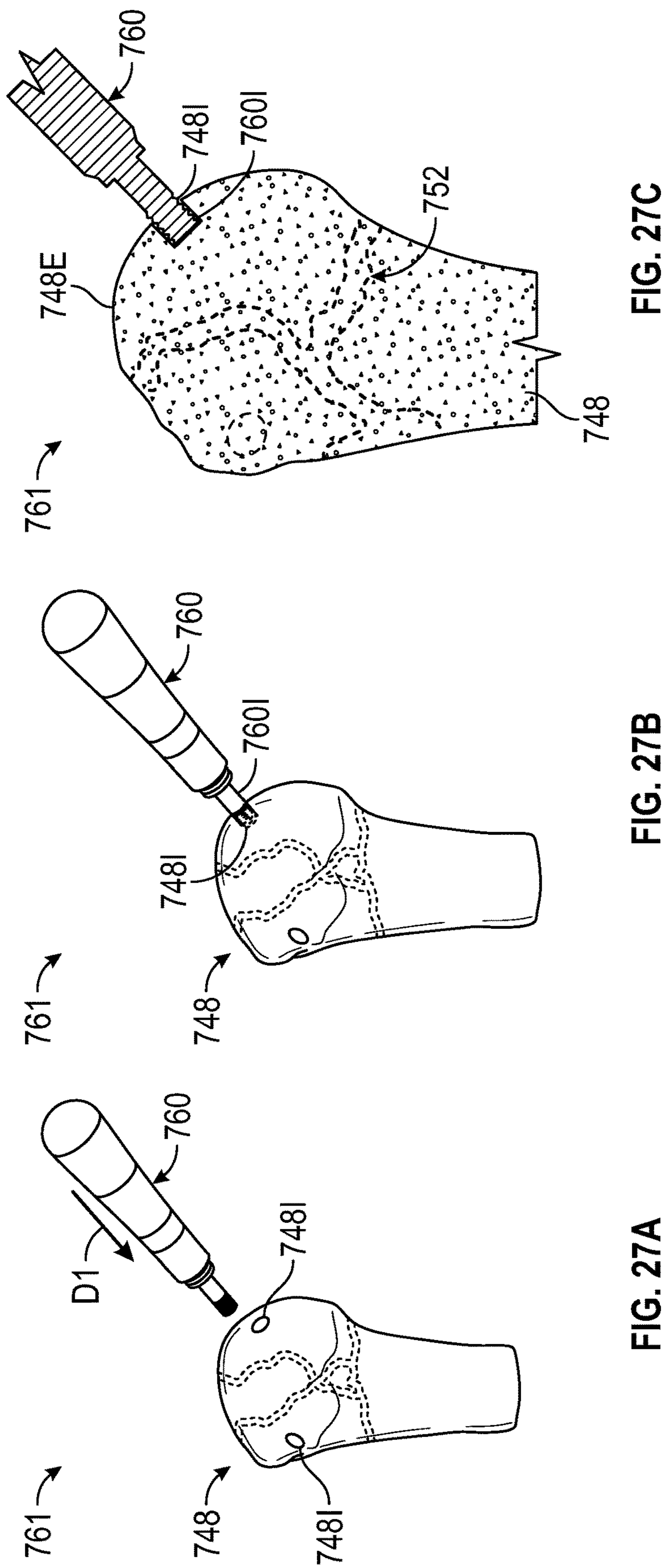
FIGS. 27A-27E disclose various states of the physical anatomical model relative to the fracture tool of FIG. 26.
Figure 27D:
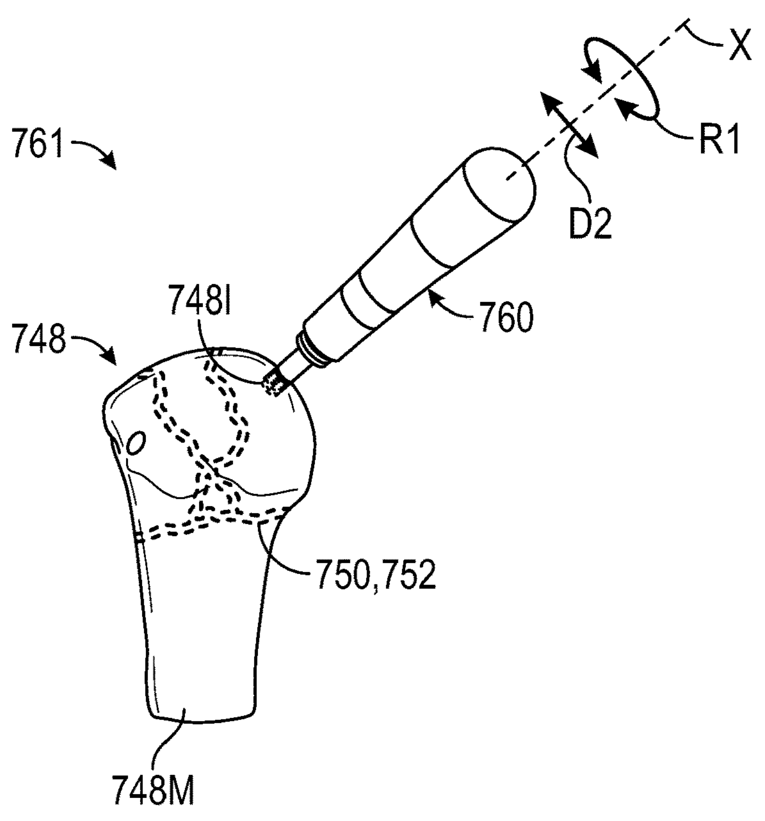
Figure 27E:
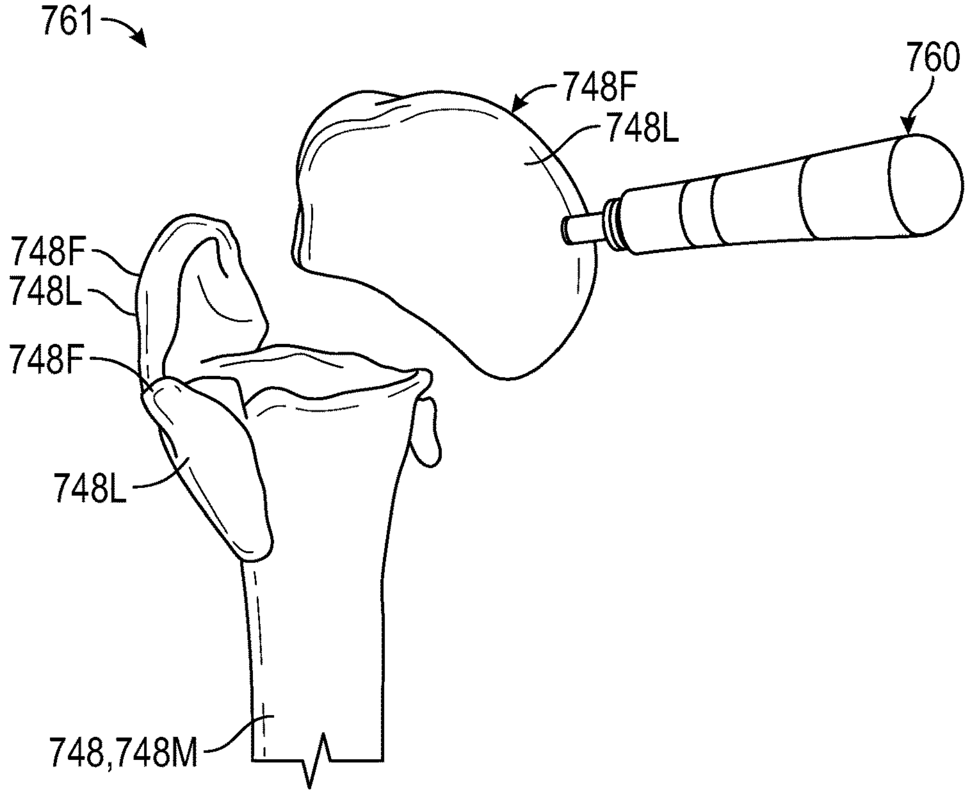

Referring to FIGS. 27A-27E, with continuing reference to FIGS. 25-26, the fracture tool 760 may be utilized to establish a fragmentary state of the physical anatomical model 748. Referring to FIG. 27A, the fracture tool 760 may be moved in a direction D1 towards a selected one of the interfaces 7481. Referring to FIGS. 27B-27C, the interface portion 7601 may engage the interface 7481 to establish a connection between the fracture tool 760 and physical anatomical model 748. Referring to FIGS. 27D-27E, the fracture tool 760 may be moveable relative to the physical anatomical model 748 to establish one or more fragments 748F. Each fragment 748F may be associated with a respective localized region 748L of the physical anatomical model 748. The fracture tool 760 may be moveable in a direction D2 (e.g., translate, etc.) and/or a rotational direction R1 (e.g., twist, pivot, etc.) relative to a longitudinal axis X of the fracture tool 760 to cause the physical anatomical model 748 to sever along an associated fracture path 750 and/or fracture volume 752. The direction D2 may be perpendicular or otherwise transverse to the axis X. In implementations, the direction D2 may be substantially parallel to the axis X.

Figure 28:
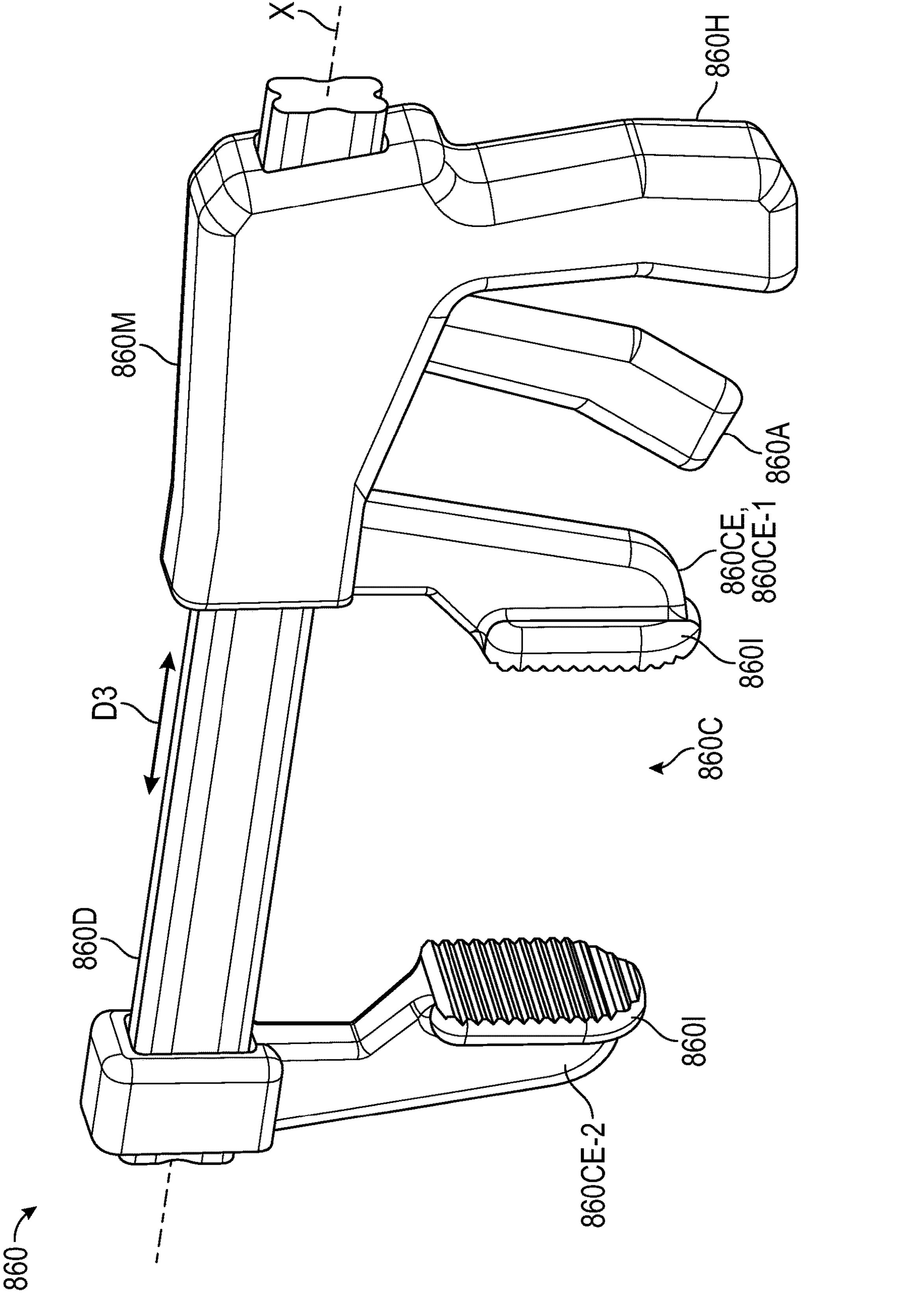
FIG. 28 discloses a perspective view of a fracture tool according to another implementation.
Figure 30:
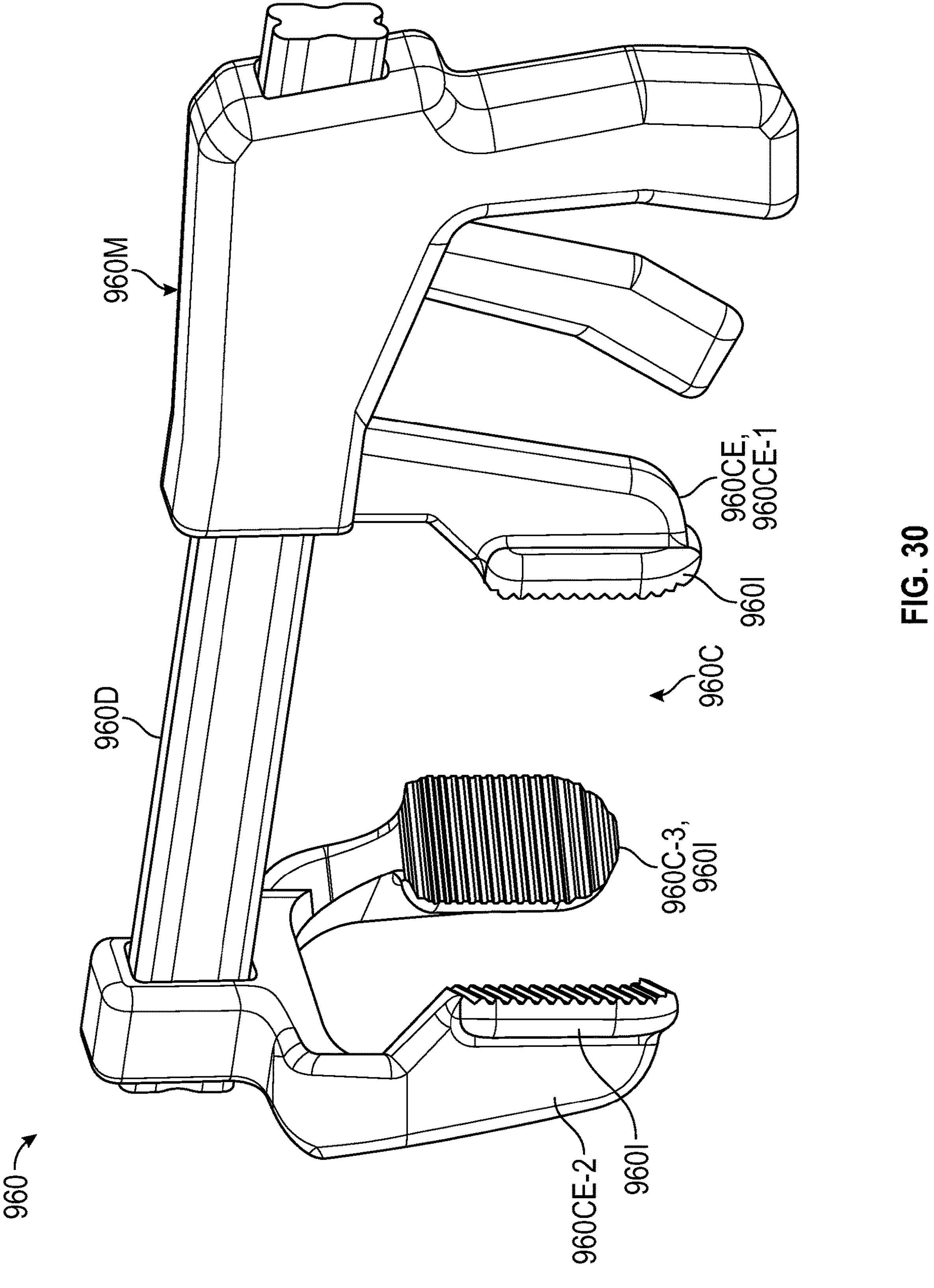
FIG. 30 discloses a fracture tool according to another implementation.

FIG. 28 discloses a fracture tool 860 according to another implementation. The fracture tool 860 may include a main body 860M and a clamp 860C. The clamp 860C may be adapted to establish a clamping action with a physical anatomical model receivable in the clamp 860C. The clamp 860C may include one or more clamp elements 860CE. Each of the clamp elements 860CE may include an interface portion 8601. The interface portion 8601 may be adapted to engage a physical anatomical model to establish a fragmentary state of the physical anatomical model. A geometry of the clamp elements 860CE and/or interface portions 8601 may be the same or may differ from each other. The clamp elements 860CE may include a first clamp element 860CE-1 and a second clamp element 860CE-2. In implementations, the clamp elements 860CE may be a set of jaws. The clamp elements 860CE-1, 860CE-2 may be dimensioned such that the respective interface portions 8601 may be opposed to each other. Each interface portions 8601 may have a generally planar face dimensioned to engage a physical anatomical model. The fracture tool 860 may have more than two clamp elements 860CE. In the implementation of FIG. 30, the fracture tool 960 may include first, second and third clamp elements 960CE-1, 960CE-2, 960CE-3 that may cooperate to establish a clamp 960C. The clamp elements 960CE-1, 960CE-2, 960CE-3 may be generally opposed to each other.

Referring to FIG. 28, the fracture tool 860 may include a drive element 860D that may actuate the clamp 860C. The drive element 860D may be adapted to set a position of the clamp elements 860CE relative to each other. The drive element 860D may be at least partially received in the main body 860M. The drive element 860D may extend along an axis X of the fracture tool 860. The drive element 860D may carry one or more of the clamp elements 860CE, such as the second clamp element 860CE-2. The drive element 860D be moveable relative to the main body 860M to set a distance between the interface portions 8601 of the clamp elements 860CE-1, 860CE-2.

The fracture tool 860 may include a handle 860H that may extend from the main body 860M. The surgeon or clinical user may manipulate the handle 860H to position the fracture tool 860 relative to a physical anatomical model. The fracture tool 860 may include an actuator 860A. Various actuators may be utilized. In implementations, the actuator 860A may include an actuation mechanism (see, e.g., 1060AM of FIG. 33) such as ratchet to set a position of the drive element 860D relative to the main body 860M of the fracture tool 860. The actuator 860A may be adapted to cause the drive element 860D to move in a third direction D3 relative to the axis X of the fracture tool 860 to set a distance between the clamp elements 860CE-1, 860CE-2. The surgeon or clinical user may manipulate the actuator 860A to cause the clamp elements 860CE-1, 860CE-2 to apply an amount of force on a physical anatomical model positioned between and engaged with the interface portions 8601 of the fracture tool 860.

Figure 29A:
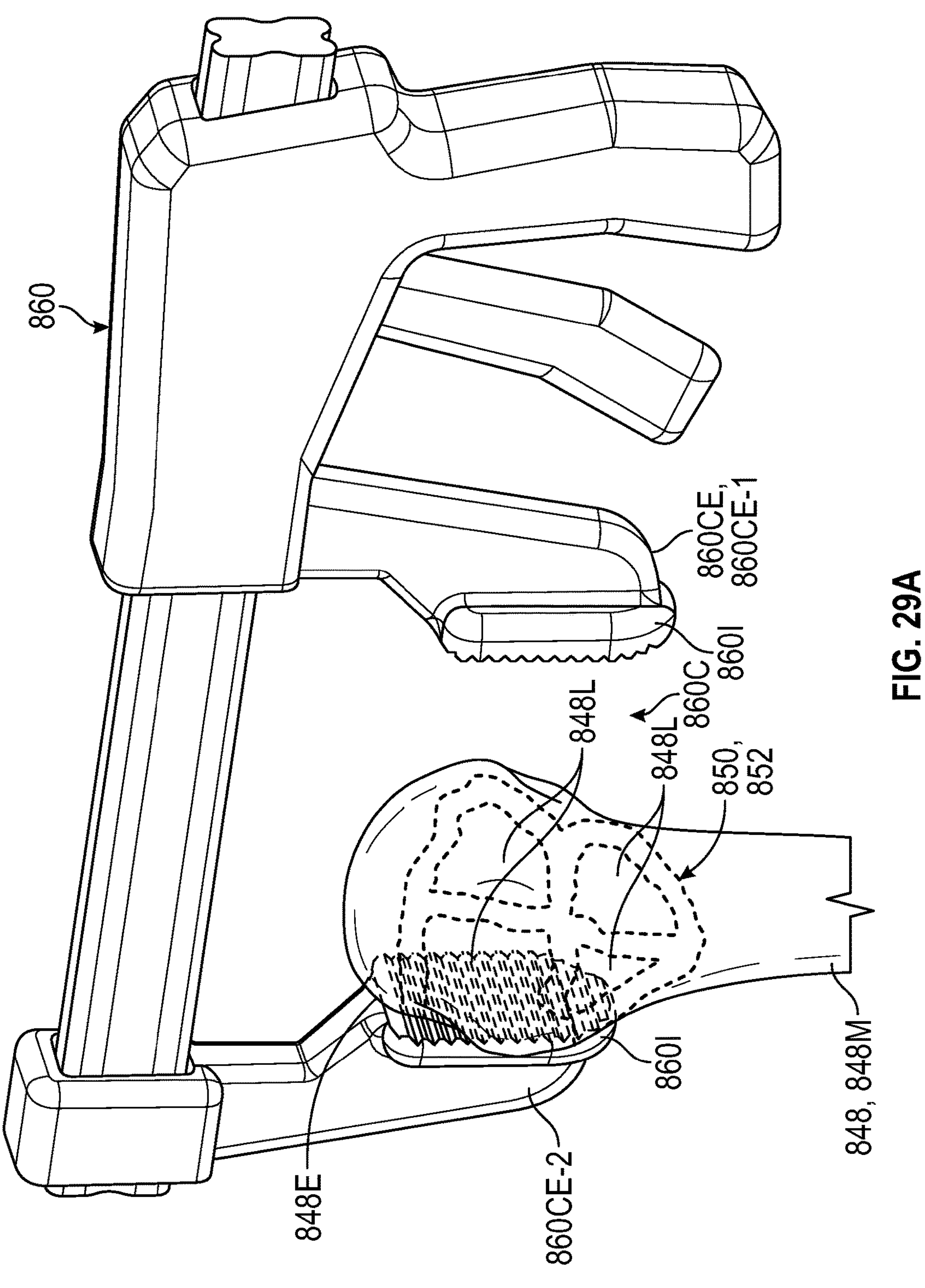
FIGS. 29A-29C discloses a perspective view of various states of the fracture tool of FIG. 28 positioned relative to a physical anatomical model.
Figure 29B:
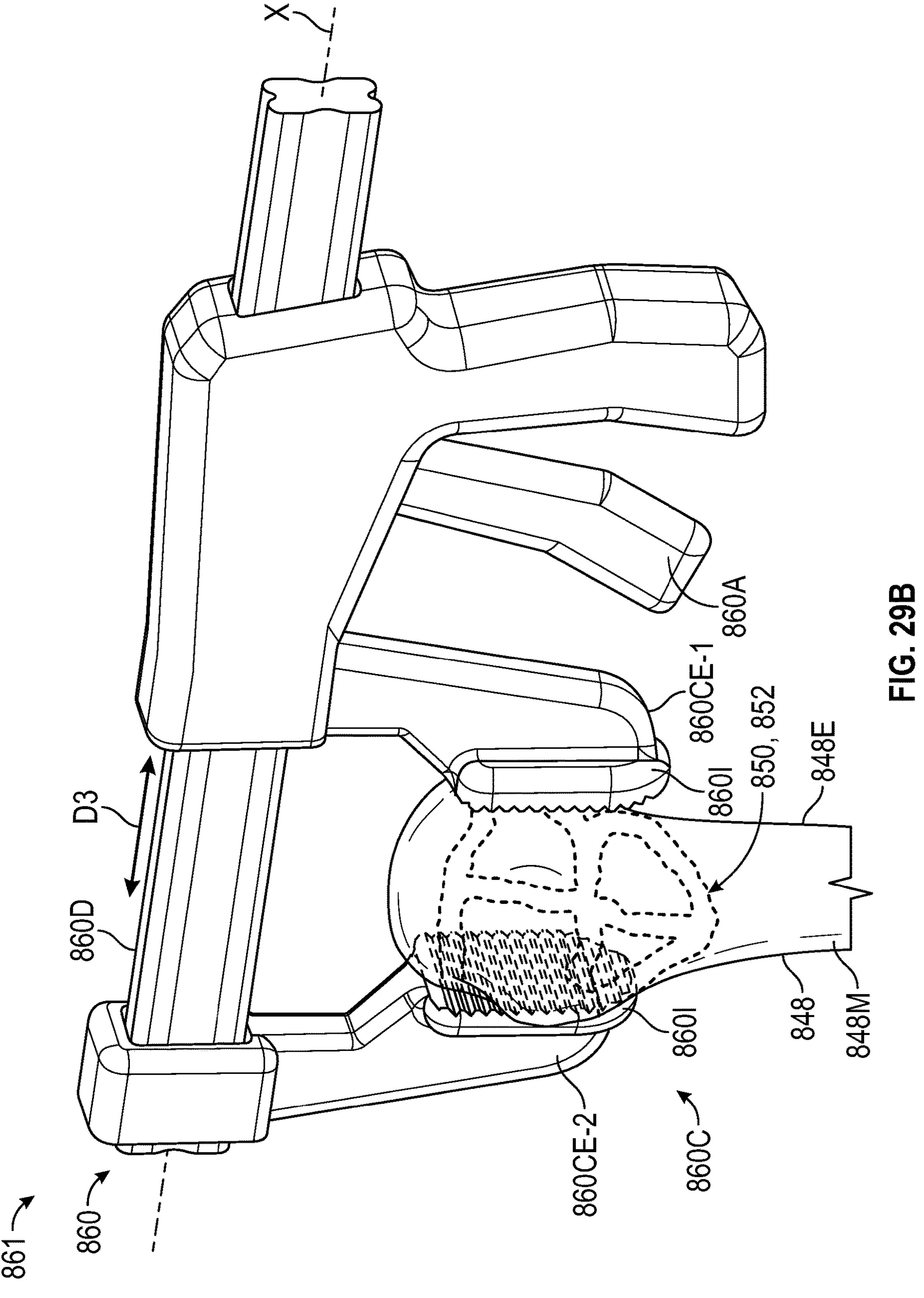
Figure 29C:
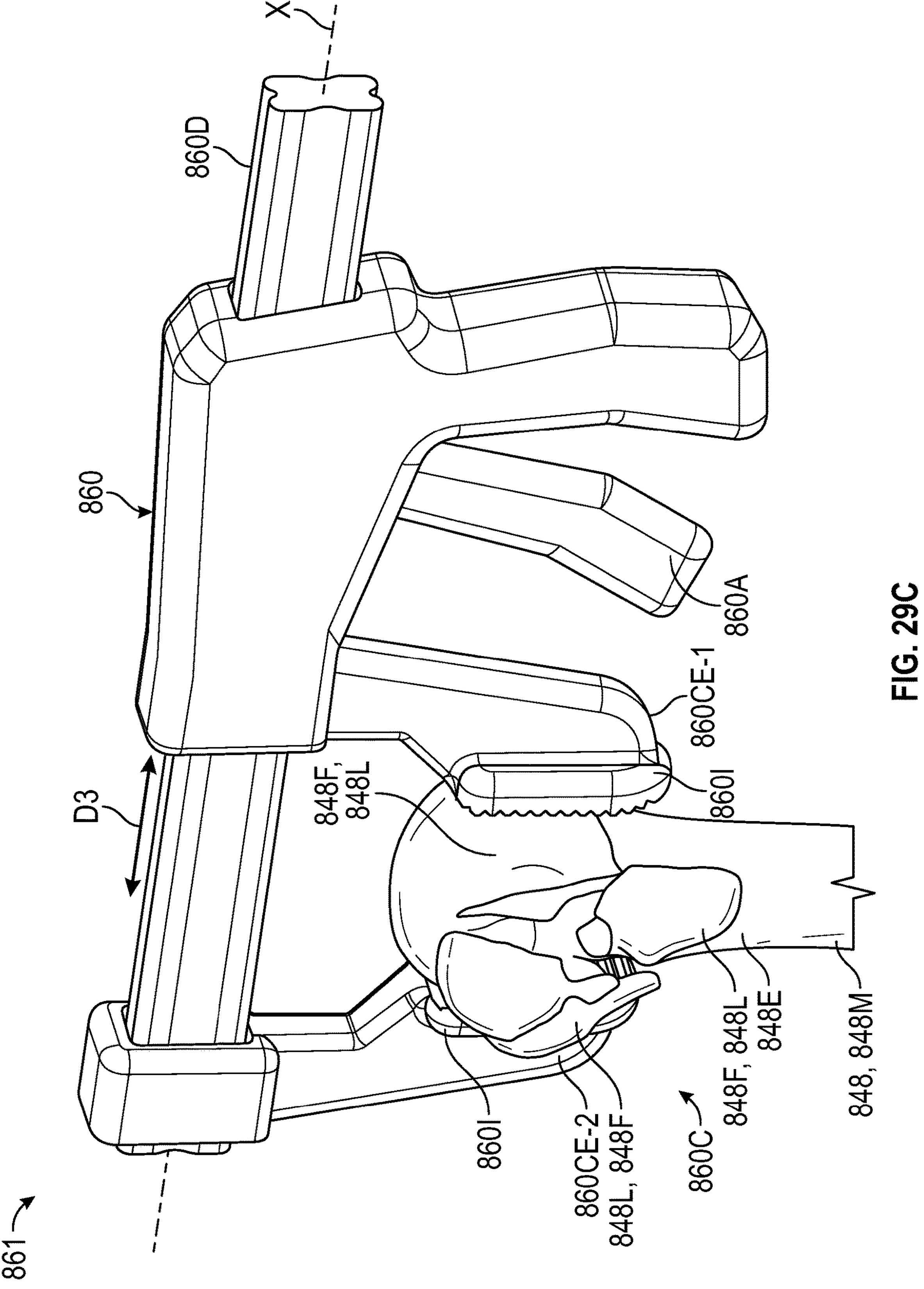

Referring to FIGS. 29A-29C, with continuing reference to FIG. 28, the fracture tool 860 may be utilized to establish a fragmentary state of a physical anatomical model 848. Referring to FIG. 29A, the physical anatomical model 848 may be positioned at least partially in the clamp 860C. The physical anatomical model 848 may be positioned between the interface portions 8481 of the clamp elements 860CE-1, 860CE-2. Referring to FIG. 29B, the surgeon or clinical user may manipulate the actuator 860A to cause the drive element 860D to move in the direction D3 such that the interface portions 8481 of the clamp elements 860CE-1, 860CE-2 may engage the external surface 848E of the physical anatomical model 848.

Referring to FIG. 29C, the drive element 860D may be moveable in the direction D3 relative to the axis X of the fracture tool 860 to cause the physical anatomical model 848 to sever along an associated fracture path 850 and/or fracture volume 852. The surgeon or clinical user may manipulate the actuator 860A to cause the interface portions 8601 of the clamp elements 860CE-1, 860CE-2 to apply an amount of compressive force on the main body 848M of the physical anatomical model 848 to cause the main body 848M to sever along the along the fracture path 850 and/or associated fracture volume 852 to establish one or more fragments 848F. Each fragment 848F may be associated with a respective localized region 848L of the physical anatomical model 848.

Figure 31:
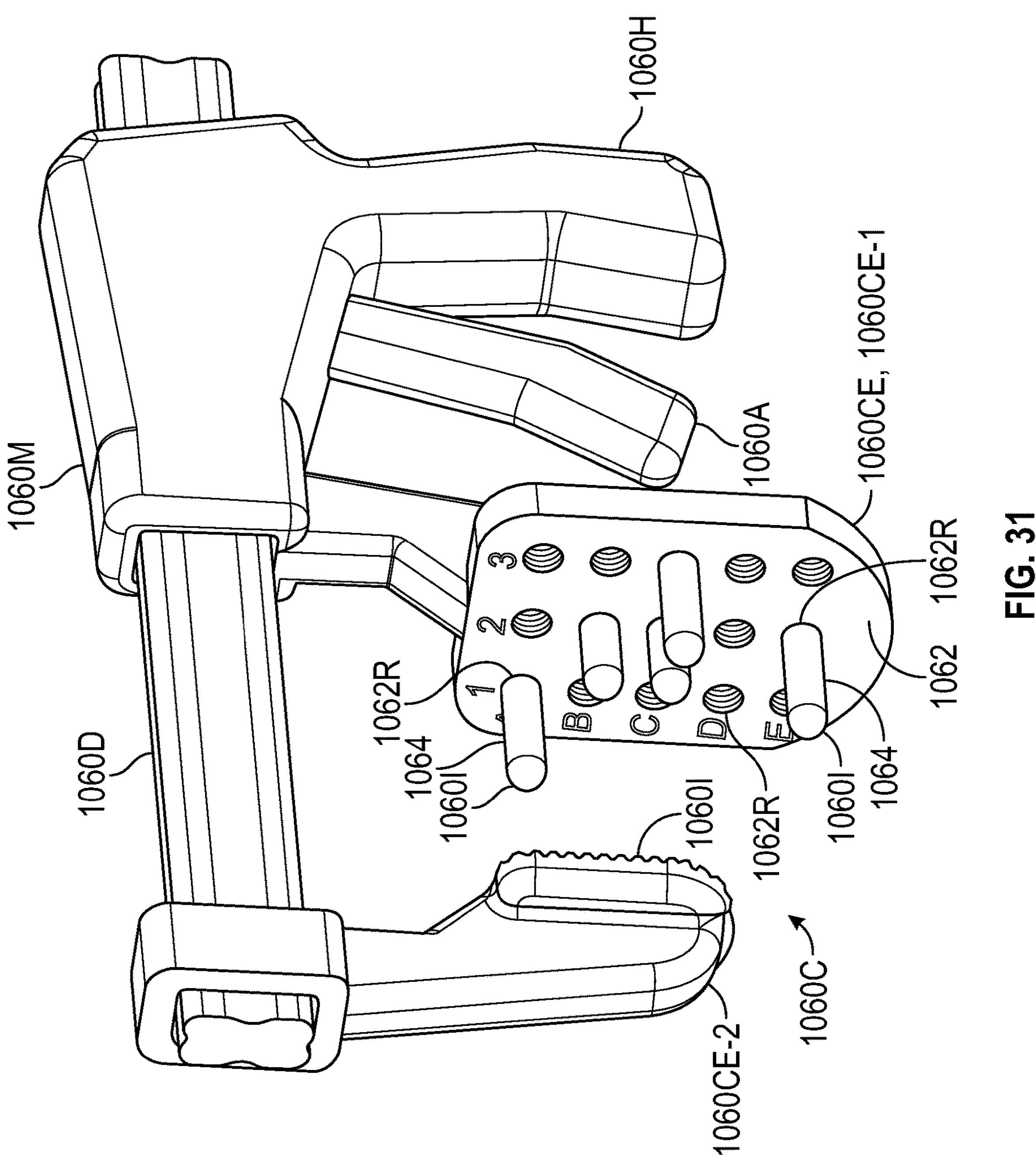
FIG. 31 discloses a perspective view of a fracture tool according to yet another implementation.
Figure 32:
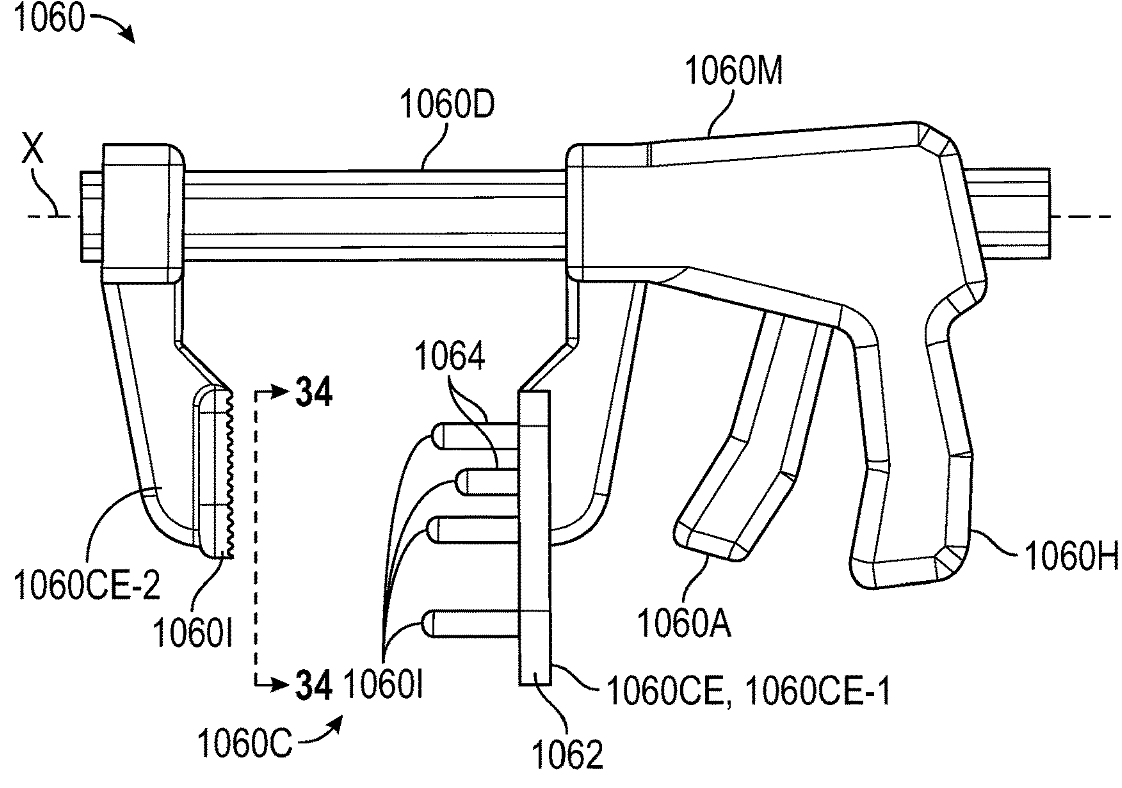
FIG. 32 discloses a side view of the fracture tool of FIG. 31.
Figure 33:
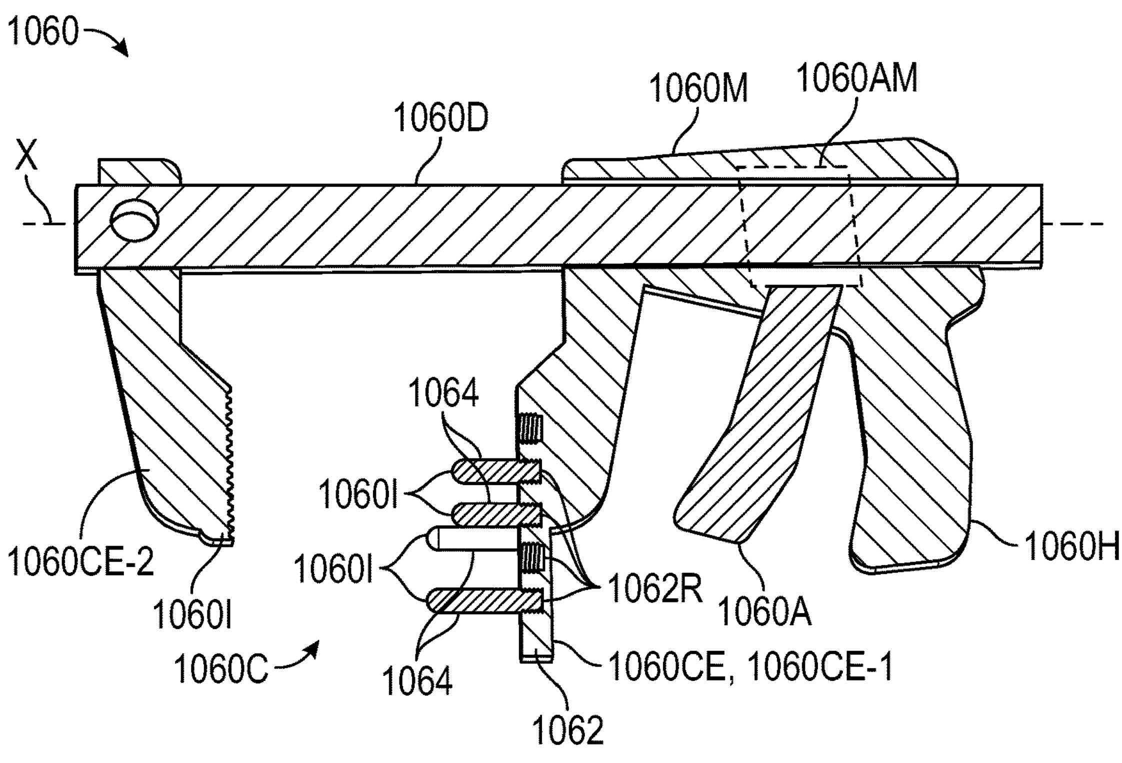
FIG. 33 discloses a sectional view of the fracture tool of FIG. 31.

FIGS. 31-33 disclose a fracture tool 1060 according to another implementation. The fracture tool 1060 may include a clamp 1060C. The clamp 1060C may include one or more clamp elements 1060CE. In the implementation of FIGS. 31-33, the clamp elements 1060CE may include a first clamp element 1060CE-1 and a second clamp element 1060CE-2. The first and second clamp elements 1060CE-1, 1060CE-2 may be opposed to each other. A geometry of the first clamp element 1060CE-1 may be the same or may differ from the second clamp element 1060CE-2. The interface portion 10601 of the second clamp element 1060CE-2 may have a generally planar face dimensioned to engage a physical anatomical model.

The first clamp element 1060CE-1 may include a base 1062 and one or more engagement elements 1064. The engagement elements 1064 may be dimensioned to engage a physical anatomical model. The engagement elements 1064 may be integrally formed with, or may be releasably securable to, the base 1062. The engagement elements 1064 may have various geometries. In the implementation of FIGS. 31-33, the engagement elements 1064 may be elongated pins. Each engagement element 1064 may establish a respective interface portion 10601 of the fracture tool 1060.

Figure 34:
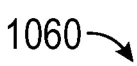
FIG. 34 discloses a view of the fracture tool taken relative to line 34-34 of FIG. 32.
Figure 34:
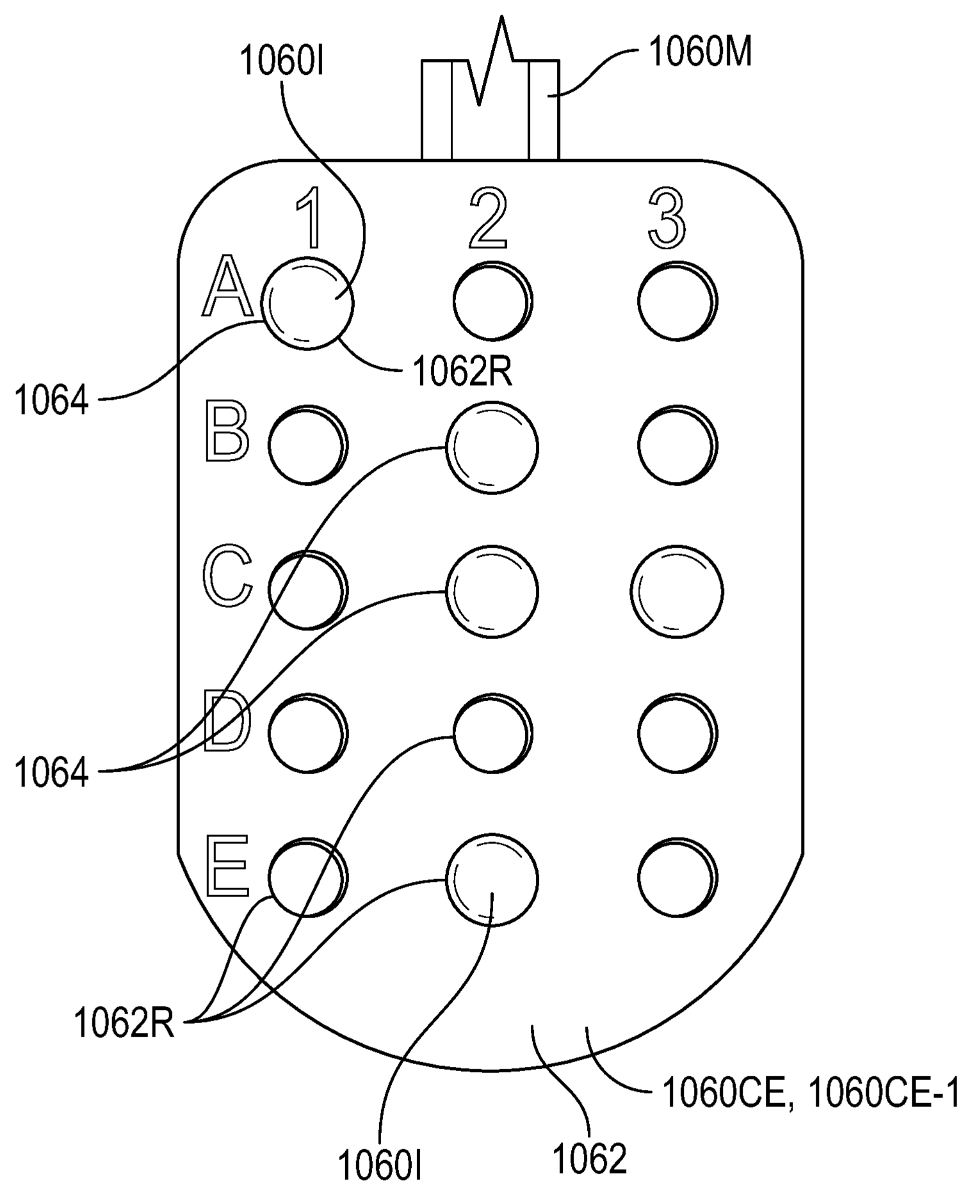

The engagement element(s) 1064 may be configurable to engage selectable contact points along a physical anatomical model and/or avoid one or more portions of the physical anatomical model. The base 1062 may include one or more receptacles 1062R. The receptacles 1062R may be established at spaced intervals along the base 1062. In the implementation of FIG. 34, the receptacles 1062R may be arranged and may be referenced in a grid (e.g., by an alphanumeric convention). Each receptacle 1062R may be assigned a unique position relative to the base 1062. Each receptacle 1062R may be dimensioned to receive an engagement element 1064.

The surgeon or clinical user may configure the fracture tool 1060 to engage one or more contact points of the physical anatomical model. The surgeon or clinical user may position one or more engagement elements 1064 in selected receptacle(s) 1062R of the base 1062. The position of each engagement element 1064 may be specified in a surgical plan 131 (FIG. 2) or may be otherwise predetermined. The surgeon or clinical user may arrange the engagement element(s) 1064 in two or more configurations to establish different fragmentary patterns of the physical anatomical model, which may be associated with a fracture classification scheme 141 and/or respective fracture pattern (FIG. 2).

Figure 35:
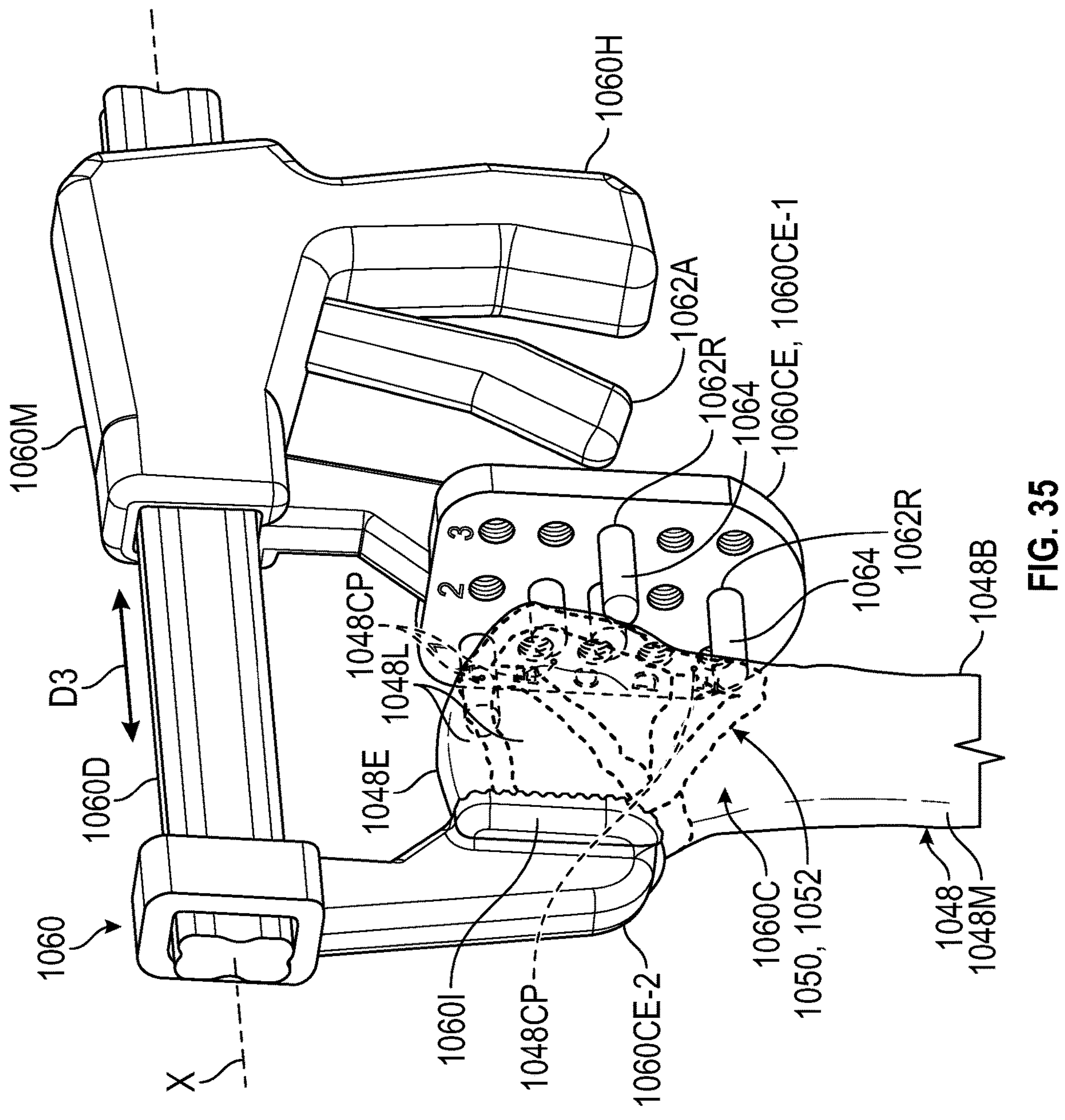
FIG. 35 discloses a perspective view of the fracture tool of FIG. 31 positioned relative to a physical anatomical model.
Figure 36:
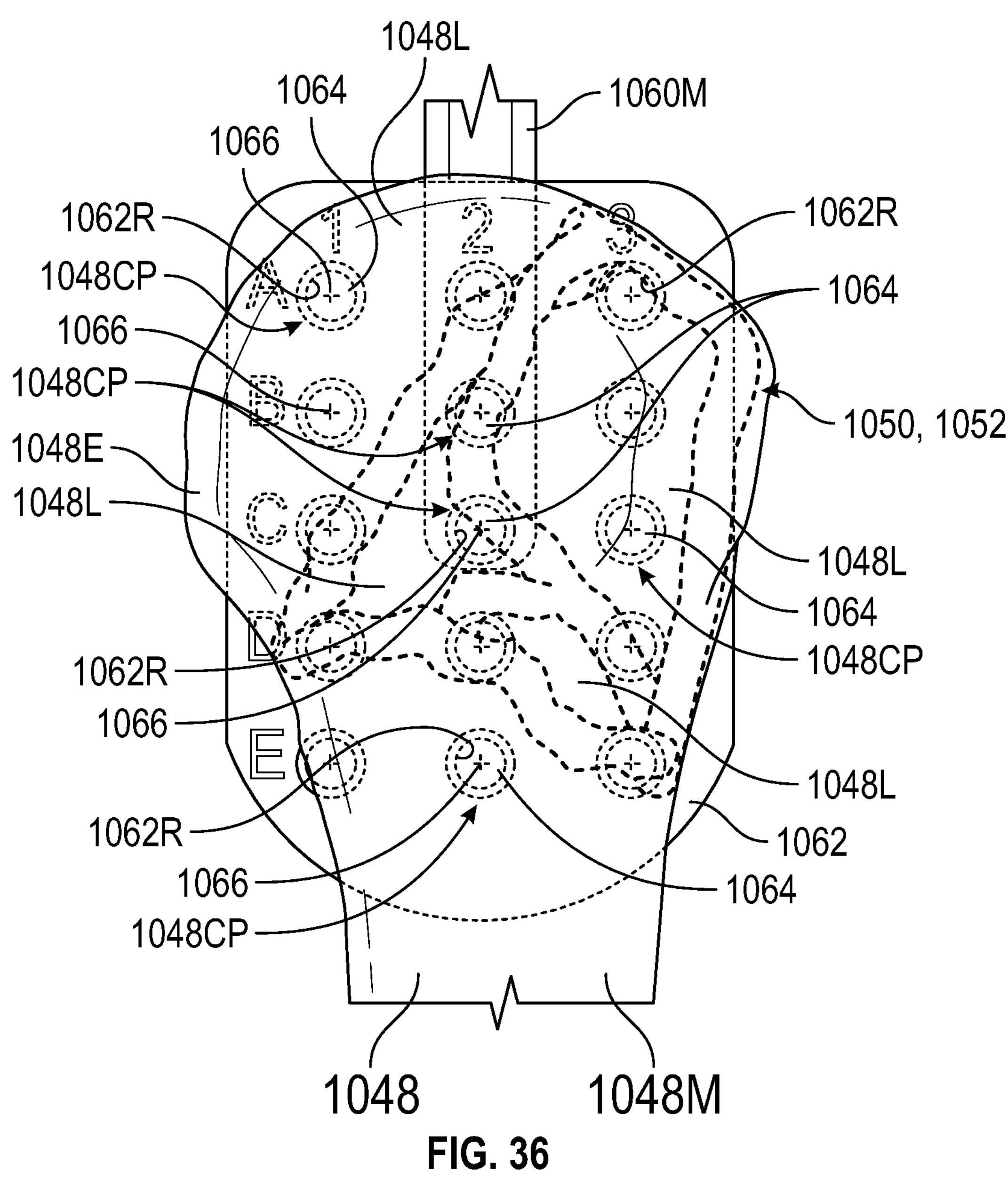
FIG. 36 discloses another view of the fracture tool positioned relative to the physical anatomical model of FIG. 35.

Referring to FIGS. 35-36, with continuing reference to FIG. 34, the engagement elements 1064 may engage selectable contact points 1048CP along a main body 1048M of a physical anatomical model 1048. The physical anatomical model 1048 may include one or more contact indicators 1066 (FIG. 36). The contact indicators 1066 may be established along an external surface 1048E of the main body 1048M adjacent to the respective contact points 1048CP. Each of the contact indicators 1066 may be associated with a respective one of the engagement elements 1064. The contact indicators 1066 may be arranged and may be referenced in a three-dimensional grid (e.g., by an alphanumeric convention) along the external surface 1048E of the physical anatomical model 1048. In implementations, a position of each contact indicator 1066 may be identified according to a respective one of the receptacles 1062R. A drive element 1060D may be moveable in a third direction D3 (FIG. 35) relative to an axis X of the fracture tool 1060 to set a distance between the second clamp element 1060CE-2 and the engagement element(s) 1064 of the first clamp element 1060CE-1.

Figure 37:
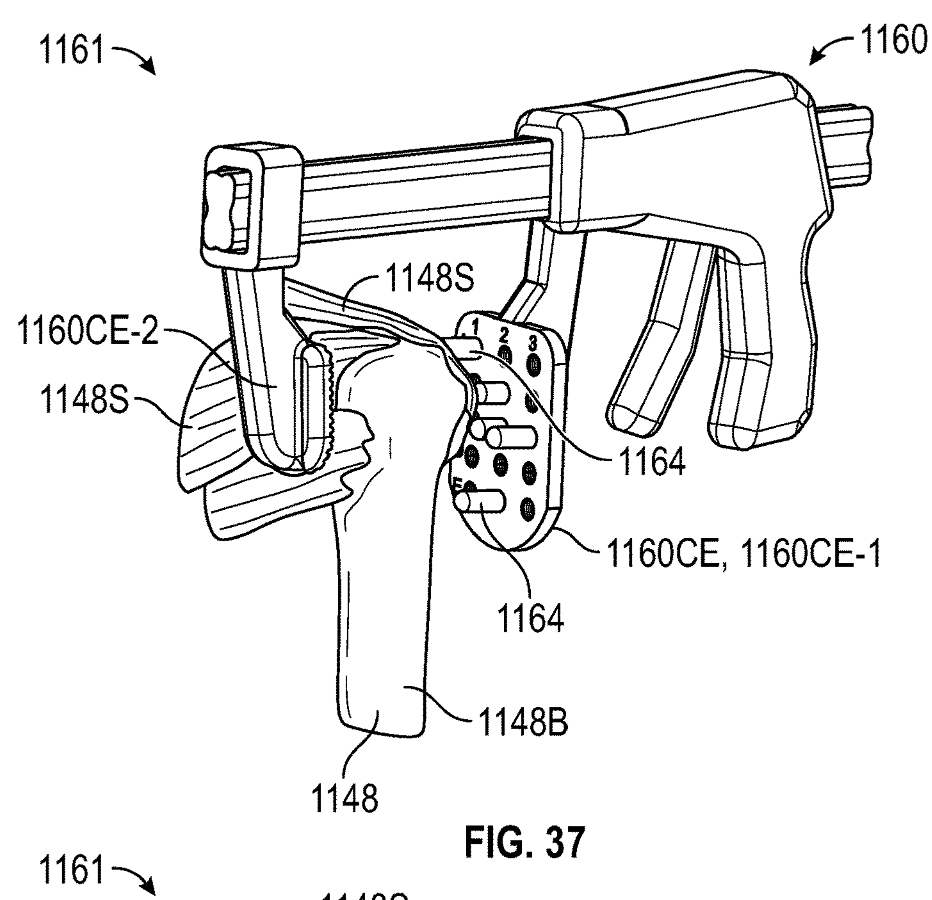
FIG. 37 discloses a perspective view of the fracture tool of FIG. 31 positioned relative to another physical anatomical model.
Figure 38:
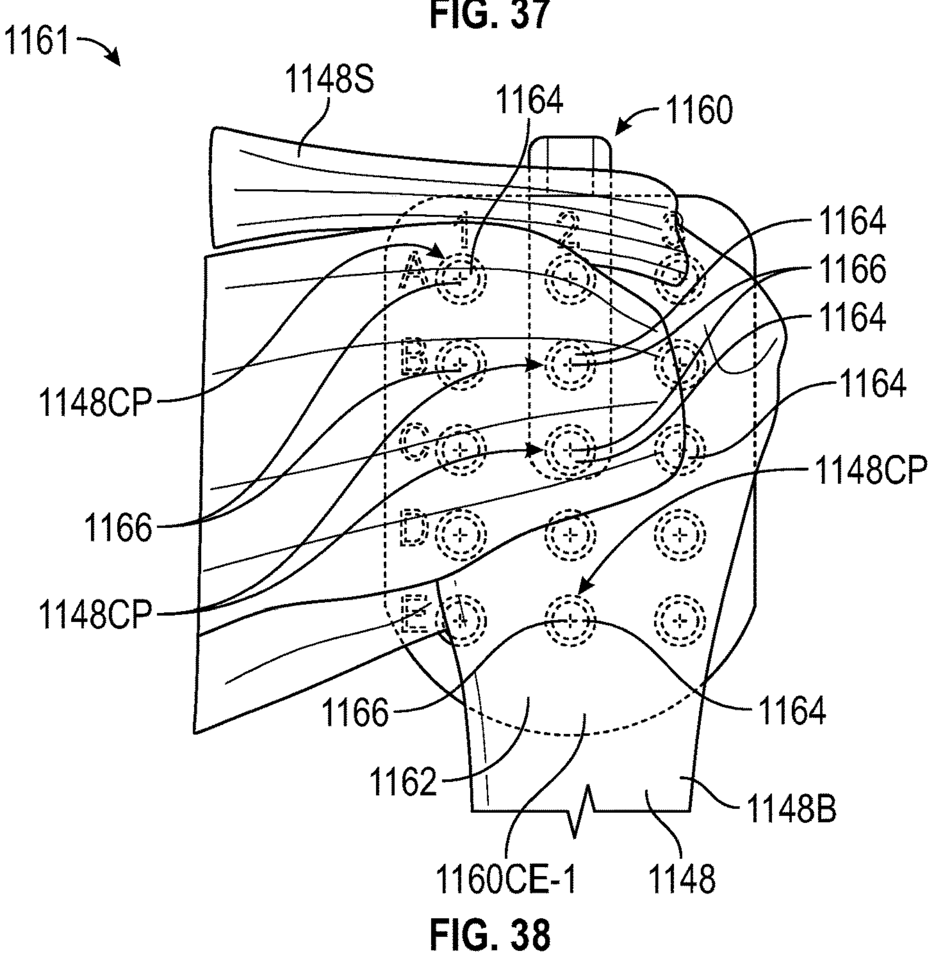
FIG. 38 discloses another view of the fracture tool positioned relative to the physical anatomical model of FIG. 37.
Figures 41A, 41B, 41C:
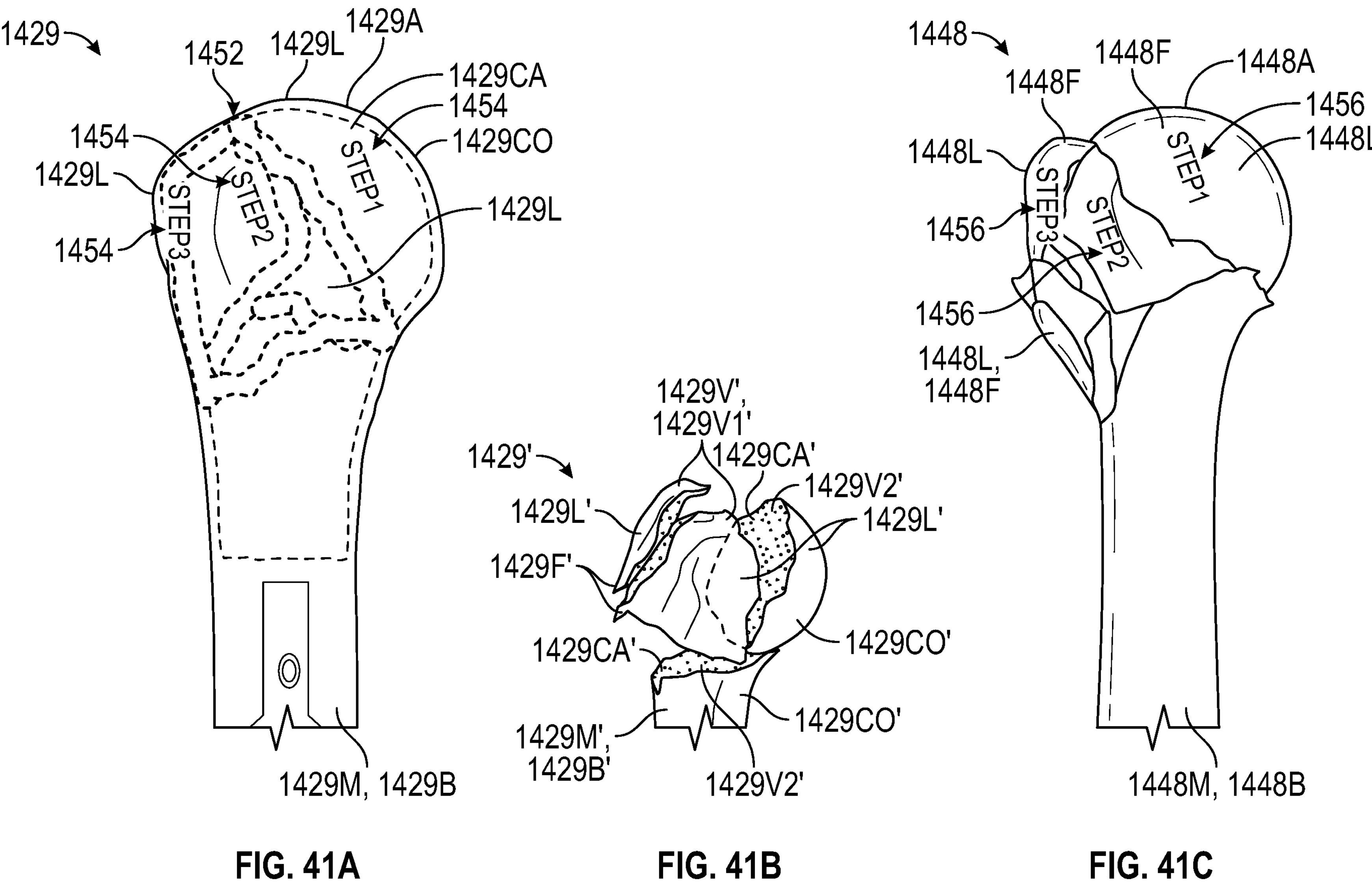
FIGS. 41A-41C disclose a virtual anatomical model, a fragmentary state of the virtual anatomical model, and a fragmentary state of a physical anatomical model associated with the virtual anatomical model.

Referring to FIGS. 37-38, each of the engagement elements 1064 of the first clamp element 1060CE-1 may be adapted to cooperate with the second clamp element 1060CE-2 to apply a compressive force at the respective contact points 1048CP to cause the main body 1048M to sever along a fracture path 1050 and/or associated fracture volume 1052 to establish the one or more fragments (see, e.g., fragments 1448F of FIG. 41C and fragments 1548F of FIGS. 42A-42B). Each engagement element 1164 may be dimensioned to engage a bone volume 1148B and/or soft tissue volume 1148S of a physical anatomical model 1148. One or more contact indicators 1166 may be established along the respective soft tissue volume 1148S.

Figure 39:
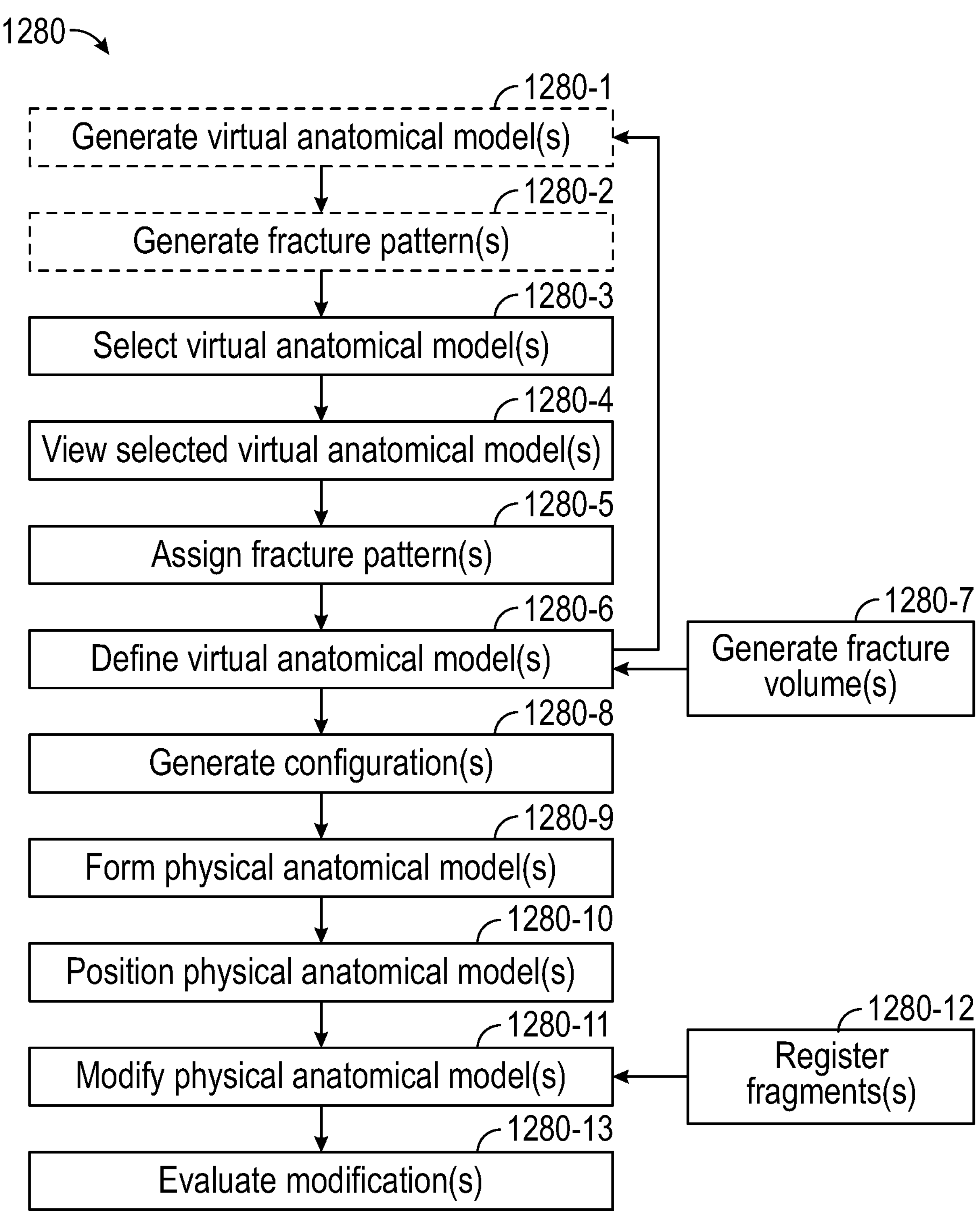
FIG. 39 discloses an exemplary method of planning and implementing a surgical procedure utilizing physical anatomical model(s).

FIG. 39 illustrates an exemplary method in a flowchart 1280. The method 1280 may be utilized to pre-operatively plan, rehearse and/or train for various surgical procedures, such as an arthroplasty for restoring functionality to shoulders, ankles, knees, hips and other joints. The method 1280 may be utilized with any of the planning systems, virtual anatomical models and/or physical anatomical models disclosed herein. The method 1280 may be utilized to establish physical anatomical model(s) for training and rehearsing for a surgical procedure. The method 1280 may be utilized to evaluate the accuracy in which a surgeon may implement a surgical procedure on a physical anatomical model associated with an anatomy of a patient or hypothetical case. Fewer or additional steps than are recited below could be performed within the scope of this disclosure, and the recited order of steps is not intended to limit this disclosure. Reference is made to the system 120 and user interface 142 for illustrative purposes.

Referring to FIG. 2, with continuing reference to FIG. 39, at step 1280-1 one or more virtual anatomical models 129 may be generated. Each virtual anatomical model 129 may be associated with an anatomy of a patient and/or hypothetical case. The virtual anatomical models 129 may be generated utilizing any of the techniques disclosed herein. The virtual anatomical models 129 may include any of the anatomies and tissue types disclosed herein, including bone, ligament, tendon, cartilage, etc. At step 1280-2, one or more fracture patterns 143 may be generated. The fracture patterns 143 may be generated utilizing any of the techniques disclosed herein.

At step 1280-3, one or more virtual anatomical models 129 may be selected from a set of virtual anatomical models 129. Each virtual anatomical model 129 may be associated with an anatomy. Various techniques may be utilized to select the virtual anatomical model 129. The virtual anatomical models 129 may be stored in memory of a computing device, such as in the database 128 or the memory 134 of the computing device 132.

Referring to FIG. 3, with continuing reference to FIGS. 2 and 39, selecting the virtual anatomical model 129 may include selecting or otherwise specifying various parameters associated with the set of virtual anatomical models 129. The parameters may include any of the parameters disclosed herein, including anatomy, patient classification, fracture classification and/or case. The parameters may be selected in response to user interaction with the graphical user interface 142.

Referring to FIGS. 5-8, with continuing reference to FIGS. 2 and 39, at step 1280-4 the selected virtual anatomical model(s) 129 may be viewed in the graphical user interface 142. Step 1280-4 may include setting the parameter(s) in response to user interaction with the graphical user interface 142. The parameters may be specified in response to the surgeon or clinical user interacting with the user interface 142. One or more of the parameters may be associated with predefined fracture classification scheme(s) 141. The fracture classification schemes 141 may include any of the fracture classification schemes disclosed herein.

Referring to FIG. 9, with continuing reference to FIGS. 2-3, 9 and 39, one or more fracture patterns 143 may be assigned to the virtual anatomical model 129 at step 1280-5. The fracture pattern 143 may be assigned to the virtual anatomical model 129 utilizing any of the techniques disclosed herein. The fracture pattern 143 may be assigned to the virtual anatomical model 129 based on one or more parameters, including any of the parameters disclosed herein such as anatomy, patient classification, fracture classification and/or case. Assigning the fracture pattern 143 may occur in response to setting one or more parameters associated with the fracture classification scheme 141. Step 1280-5 may include causing the virtual anatomical model 129 and/or the assigned fracture pattern 143 to be displayed in one or more display windows 144 of the graphical user interface 142, such as the display windows 144-6A to 144-6D.

At step 1280-6, aspects of one or more of the virtual anatomical models 129 may be defined. Each virtual anatomical model 129 may be defined prior, during and/or subsequent to generating the virtual anatomical model(s) 129 at step 1280-1, generating the fracture pattern(s) 143 at step 1280-2, selecting the virtual anatomical model(s) 129 at step 1280-3, viewing the selected virtual anatomical model(s) 129 at step 1280-4 and/or assigning fracture pattern(s) 143 to the virtual anatomical model(s) 129 at step 1280-5. Defining the virtual anatomical model 129 may include setting one or more parameters of the virtual anatomical model 129, including any of the parameters disclosed herein. The parameters may be selected in response to user interaction with the graphical user interface 142 (e.g., FIG. 3). The parameters may be associated with one or more fracture classifications 141 (FIG. 2) and/or fracture patterns 143 (e.g., FIGS. 2 and 9).

Referring to FIGS. 12 and 13A-13B, with continuing reference to FIGS. 2 and 39, defining the virtual anatomical model 129 may include generating one or more virtual fracture volumes 147 at step 1280-7. Each virtual fracture volume 147 may be established utilizing any of the techniques disclosed herein.

At step 1280-8, one or more configurations (e.g., definitions) 145 may be generated. Each configuration 145 may be associated with at least one virtual anatomical model 129, fracture pattern 143, physical anatomical model 148, fracture path 150 and/or physical fracture volume 152. Each configuration 145 may be generated utilizing any of the techniques disclosed herein. The configuration 145 may be associated with a physical anatomical model 148 that may be representative of a selected virtual anatomical model 129. Each configuration 145 may be generated in response to selecting the respective virtual anatomical model 129 at step 1280-3, assigning the respective fracture pattern 143 at step 1280-5 and/or defining the selected virtual anatomical model 129 at step 1280-6. The configuration may be established according to the selection or setting of any parameters associated with the selected virtual anatomical model 129, including any fracture pattern 143 and/or fracture volume 152. The configuration 145 may include data and other information sufficient to establish a physical anatomical model 148 based on the parameters of the selected virtual anatomical model 129, including coordinate information, color, texture and/or moduli of elasticity of the associated tissues, geometry associated with one or more fracture paths 150 and associated indicators, etc. The configuration 145 may specify one or more fracture paths 150 established in the physical anatomical model 148 according to the assigned fracture pattern 143.

Referring to FIG. 18, with continuing reference to FIGS. 2 and 39, in implementations the configuration 145 may specify one or more physical indicators 356. The physical indicators 356 may be associated with a fracture path 350 and/or fracture volume 352. The physical indicators 356 may be established according to any of the techniques disclosed herein. Each physical indicator 356 may be associated with a respective virtual indicator 354 (see, e.g., FIG. 17).

Referring to FIG. 36, with continuing reference to FIGS. 2 and 39, the configuration 145 may specify one or more indicators such as a plurality of contact indicators 1066 distributed along a physical anatomical model 1048. Each of the contact indicators 1066 may be associated with a respective contact element 1064 of a fracture tool 1060.

Referring to FIG. 14, with continuing reference to FIGS. 2, 13A-13B and 39, one or more physical anatomical models 148 may be fabricated or otherwise formed at step 1280-9. The physical anatomical model 148 may be formed to closely resemble or approximate a geometry of the associated anatomy, including soft tissue and bone. In implementations, the surgeon may interact with the physical anatomical model 148 such that portion(s) of the physical anatomical model 148 may feel similar to soft (e.g., cancellous) bone tissue, muscle and other soft tissue, etc. The physical anatomical model 148 may be printed or otherwise formed according to the various parameters selected in the user interface 142. Various parameters may be utilized to form the physical anatomical model 148, including any of the parameters disclosed herein, such as density of bone and soft tissue, thickness of cortical bone, indicators, patient age, etc.

Each physical anatomical model 148 may be fabricated or otherwise formed based on a configuration 145 generated at step 1280-8. Various materials may be utilized to form the physical anatomical models. The physical anatomical model 148 including the main body 148M may incorporate metallic and/or non-metallic materials, including any of the materials disclosed herein such as a polymeric material. In implementations, the main body 148M may be formed from a substantially rigid material, such as a polymeric material, including photopolymers, silicones and thermoplastics. Portions of the physical anatomical model 148 may be formed from a relatively flexible material, including an elastomeric material such as rubber or silicone, to establish soft tissue volume(s) representative of any of the soft tissue disclosed herein.

Various techniques may be utilized to form the physical anatomical models. Each physical anatomical model may be formed utilizing any of the techniques disclosed herein, such as rapid prototyping (e.g., printing) and other additive manufacturing techniques, casting, machining, etc. The physical anatomical model may have a unitary construction or may have two or more components fixedly attached or otherwise secured to each other to establish a unit.

Figure 40:
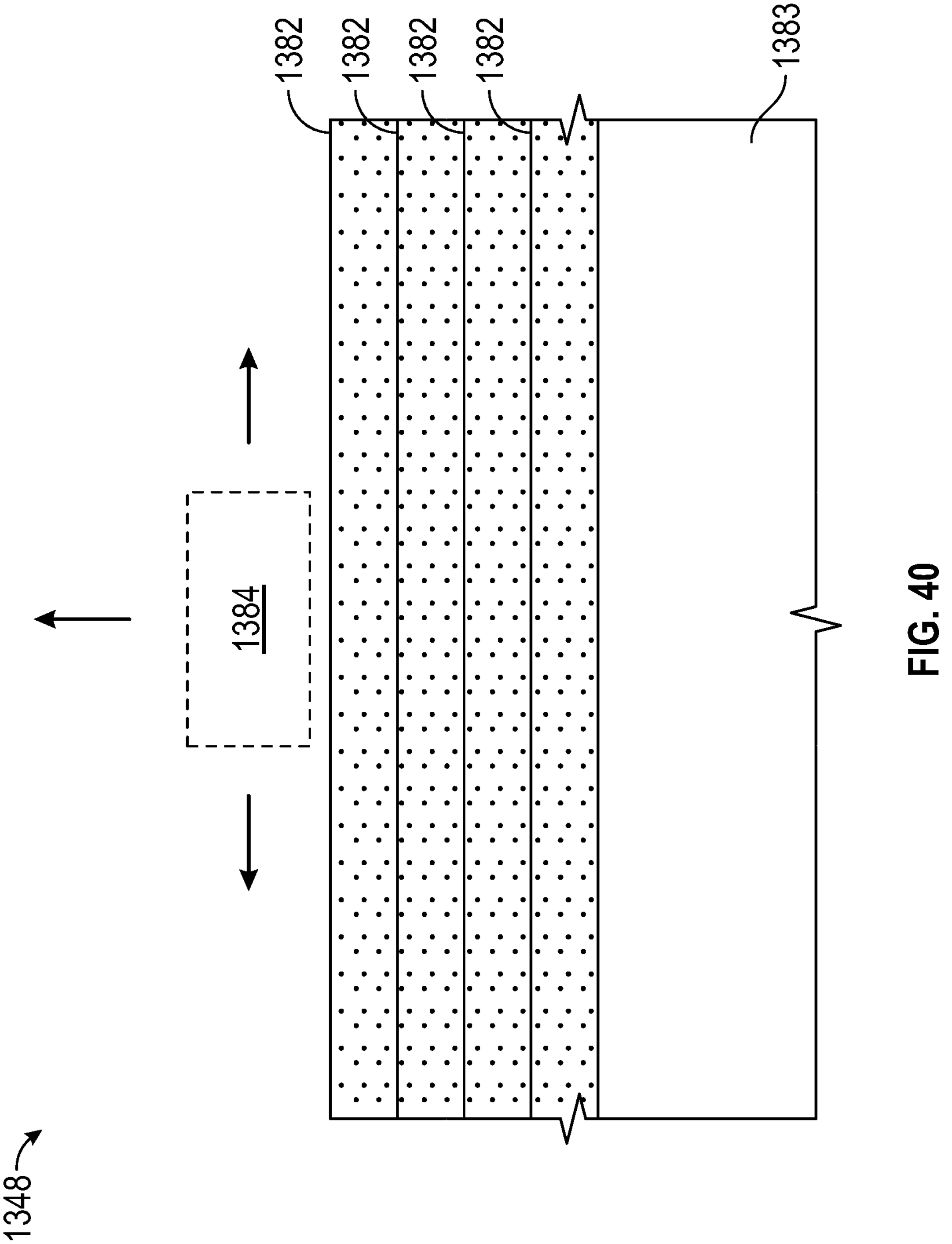
FIG. 40 disclose a technique for forming a physical anatomical model.

In the implementation of FIG. 40, one or more layers 1382 of material may be printed or otherwise formed on a substrate 1383 to establish a physical anatomical model 1348. The physical anatomical model 1348 may be representative of a virtual anatomical model, including any of the virtual anatomical models disclosed herein. A device 1384 such as a three-dimensional printer may be configured to form the layers 1383 according to data and other information associated with the respective configuration 145. The layers 1383 of material may include any of the constructions, materials, color schemes, textures, porosities, etc. disclosed herein. The layers 1383 may have respective moduli of elasticity that may substantially correspond to moduli of elasticity of respective biomaterial of the anatomy. The porosities of the material forming the physical anatomical model 1348 may substantially approximate the porosity or density of the respective tissue.

In the implementation of FIG. 14, the physical anatomical model 148 may include a first volume 148V1 and a second volume 148V2. The first volume 148V1 may be representative of cortical bone. The second volume 148V2 may be representative of cancellous bone. The fracture path 150 may establish one or more localized regions 148L of the physical anatomical model 148. The configuration 145 established at step 1280-9 may specify a fracture volume 152 that may follow a length of the fracture path 150. The physical anatomical model 148 may be severable along the fracture path 150 and/or fracture volume 152 to establish one or more fragments associated with the respective localized regions 148L. The physical fracture volume 152 may establish a frangible connection between the localized region 148L and adjacent localized region(s) 148L and/or main body 148M of the physical anatomical model 148.

At step 1280-10, the surgeon or clinical user may position or otherwise prepare the physical anatomical model 148. The physical anatomical model 148 may be secured to at least one fixture 166 to establish an assembly 168 (shown in dashed lines in FIG. 14). The fixture(s) 166 may be arranged relative to a static structure and/or one or more reusable components. The fixture(s) 166 may be representative of surrounding tissue or a portion of a joint. The surgeon may utilize the fixture(s) 166 to simulate rotating or moving a limb in an operating room. Fixture(s) 166 may be representative of skin tissue and may be formed from a relatively flexible material, such as an elastomeric material. The surgeon may form one or more openings in the fixture 166 to simulate performing an incision to expose a joint, bone and/or another portion of the anatomy.

Referring to FIGS. 19-20, with continuing reference to FIGS. 2 and 39, one or more modifications to the physical anatomical model(s) 348 may be performed at step 1280-11. The physical anatomical model 148 may be provided to the surgeon or clinical user in a pre-fragmentary state or a fragmentary state. Step 1280-11 may include causing the main body 348M of the physical anatomical model 348 to sever along the fracture path 350 and/or physical fracture volume 352 to establish a fragmentary state of the physical anatomical model 348 including one or more fragments 348F (see also fragments 1448F of FIG. 41C and fragments 1548F of FIGS. 42A-42B). Various techniques may be utilized to establish a fragmentary state of the physical anatomical model 348, including any of the techniques and fracture tools disclosed herein (see, e.g., fracture tools 760, 860 of FIGS. 27E and 29C). The main body 348M of the physical anatomical model 348 may be severable along the fracture path 350 and/or fracture volume 352 to establish the fragment(s) 348F in response to causing a fracture tool to apply an amount of force at one or more selected contact points along the physical anatomical model 348, such as adjacent to the respective contact indicator(s) (see, e.g., contact points 1048CP and contact indicators 1066 of FIG. 36). In the implementation of FIG. 36, the fragments may be established in response to causing the fracture tool 1060 to apply an amount of force at a contact point 1048CP along the physical anatomical model 1048 adjacent to the respective contact indicator 1066. An amount of force at the contact point sufficient to cause the physical anatomical model 348 to fracture may be determined utilizing various techniques, such as analysis of empirical data, parametric modeling, etc. Severing the physical anatomical model 348 may occur such that one or more physical indicators may be exposed such as a fracture volume 352 established below an external surface 348E of the physical anatomical model 348 and establishing a visual contrast with adjacent portions of the physical anatomical model 348 (see, e.g., fracture volume 152' of FIG. 14). External indicator(s) may present less of a challenge to the surgeon. The surgeon may select to have indicator(s) formed below the external surface of the physical anatomical model, which may more closely approximately a surgical procedure on the anatomy and may be relatively more challenging.

The surgeon or clinical user may perform various modifications to a fragmented instance of the physical anatomical model 348 to simulate surgical operations performed on an anatomy to restore functionality to a patient. The simulated surgical operations may include one or more repairs to the anatomy, such as one or more cutting, drilling, reaming, resection and implantation operations. Each modification may result in permanently altering a geometry of the physical anatomical model 348. Step 1280-11 may include registering one or more fragments 348F relative to each other and/or a remainder of the main body 348M of the physical anatomical model 348 (see also FIG. 42B). Step 1280-11 may include securing an orthopaedic implant to the registered fragments 1548F and/or main body 1548M of the physical anatomical model 1548 (see, e.g., FIGS. 42C-42D).

Referring to FIGS. 19-20, with continuing reference to FIGS. 2 and 39, at step 1280-13 one or more modifications to the physical anatomical model(s) may be evaluated utilizing any of the techniques disclosed herein. Step 1280-13 may include determining a state of one or more physical indicators 356 subsequent to modifying the physical anatomical model 348 at step 1280-11, including registering or otherwise positioning one or more fragments 348F relative to each other and/or a remainder of the main body 348M of the physical anatomical model 348 at step 1280-12. Step 1280-13 may include comparing the revised physical anatomical model(s) 348 (e.g., FIGS. 19 and 20) to a previous (e.g., initial or pre-fragmentary) state of the physical anatomical model(s) 348 (e.g., FIG. 18).

FIGS. 41A-41C disclose a virtual anatomical model 1429, a virtual anatomical model 1429' and a physical anatomical model 1448 according to an implementation. The virtual anatomical model 1429' may be a fragmentary instance of the virtual anatomical model 1429 and may include one or more fragments 1429F'. In implementations, the virtual anatomical model 1429' may be representative of a four-part fracture of an articular portion of a long bone such as a proximal humerus. The physical anatomical model 1448 may be a physical instance of the virtual anatomical model 1429' and may include one or more fragments 1448F registered or otherwise positioned relative to each other and/or a remainder of the main body 1448M of the physical anatomical model 1448. The virtual anatomical models 1429, 1429' and physical anatomical model 1448 may be established and arranged utilizing any of the techniques disclosed herein, including any of the steps of the method 1280.

In implementations, the virtual anatomical model 1429 may include one or more virtual indicators 1454. The virtual indicators 1454 may be associated with a predetermined order of registered or otherwise arranging the localized regions 1429L relative to each other and/or the main body 1429 of the virtual anatomical model 1429. The physical anatomical model 1448 may include one or more physical indicators 1456. Each physical indicator 1456 may be associated with a respective one of the virtual indicators 1454. The surgeon may utilize the physical indicators 1456 to determine an order of arranging the fragments(s) 1448F relative to each other and/or a remainder of the main body 1448M of the physical anatomical model 1448, which may facilitate training the surgeon for an associated fracture and treatment option.

FIGS. 42A-42D disclose various states of a physical anatomical model 1548 according to an implementation. FIG. 42A discloses a fragmentary state of the physical anatomical model 1548, which may include one or more fragments 1548F registered or otherwise positioned relative to each other and/or a main body 1548M of the physical anatomical model 1548. In implementations, the physical anatomical model 1548 of FIGS. 42A-42D may be representative of a four-part fracture of an articular portion of a long bone such as a proximal humerus. In the implementation of FIG. 42B, one or more of the fragments 1548F may be registered or otherwise positioned relatively closer to each other and/or the main body 1548M than in the arrangement of FIG. 42A.

Referring to FIGS. 42C-42D, with continuing reference to FIG. 42B, an orthopaedic system 1571 may include at least one, or more than one, implant 1582. The implant 1582 may be associated with a respective implant model 130 (FIG. 2). The surgeon or clinical user may position the implant 1582 relative to the main body 1548M and/or fragments 1548F of the physical anatomical model 1548. The surgeon or clinical user may position one or more fasteners (e.g., compression screws) 1584 through the implant 1582 and into the main body 1548M and/or fragments 1548F to secure the fragments 1548F to each other and/or the main body 1548M. The physical anatomical model 1548 of FIGS. 42A-42D and implant 1582 may be established and arranged utilizing any of the techniques disclosed herein, including any of the steps of the method 1280.

The techniques disclosed herein may be utilized to establish other virtual and physical anatomical models representative of anatomy. The techniques disclosed herein may be utilized to establish virtual and physical anatomical models representative of any of the anatomy disclosed herein, including shoulders, ankles, knees, hips and other joints. The physical anatomical models may be utilized with various fixtures, including reusable fixtures that may be representative of anatomy.

Figures 43, 44A, 44B:
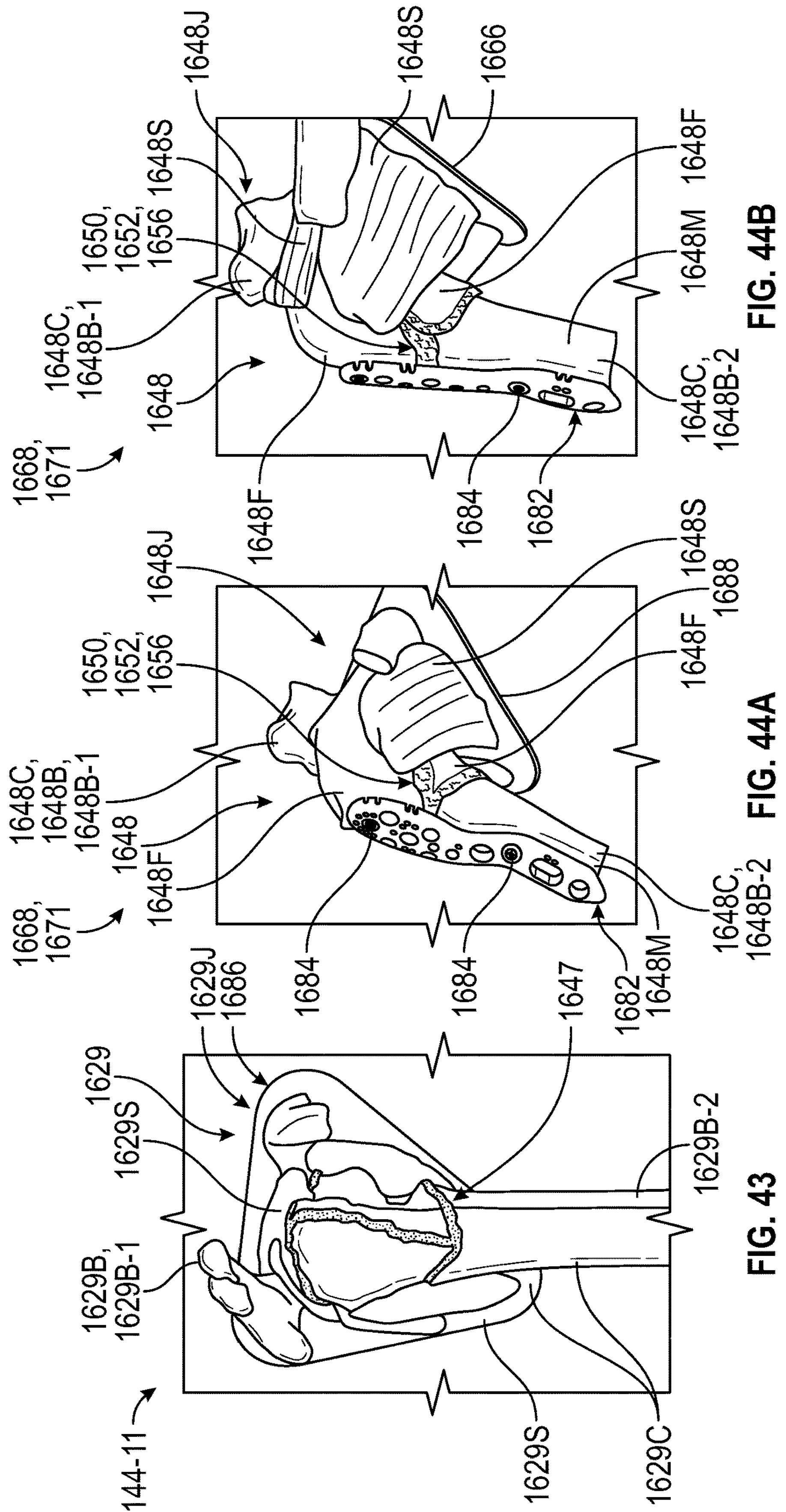
FIG. 43 discloses another implementation of a virtual anatomical model in a display window.
FIGS. 44A-44B disclose a physical anatomical model associated with the virtual anatomical model of FIG. 43.

FIG. 43 discloses another implementation of a virtual anatomical model 1629 in a display window 144-11 of the planning system 120 (FIG. 2). The virtual anatomical model 1629 may be representative of a shoulder joint. The virtual anatomical model 1629 may include one or more components 1629C, such as one or more bone volumes 1629B and/or one or more soft tissue volumes 1629S. The virtual anatomical model 1629 may include a first bone volume 1629B-1 and a second bone volume 1629B-2. The first bone volume 1629B-1 may be associated with a scapula. The second bone volume 1629B-2 may be associated with a humerus. The soft tissue volumes 1629S may be associated with respective portions of a rotator cuff. The bone volumes 1629B-1, 1629B-2 and soft tissue volumes 1629S may establish a portion of a joint 1629J. The joint 1629J may be associated with a shoulder joint. One or more of the bone volumes 1629B may be associated with a respective fracture volume 1647. The fracture volume 1647 may be established utilizing any of the techniques disclosed herein. The virtual anatomical model 1629 may be situated relative to a virtual fixture 1686. The virtual fixture 1686 may have various geometries, such as a generally planar geometry.

FIGS. 44A-44B disclose a physical anatomical model 1648. The physical anatomical model 1648 may be associated with the virtual anatomical model 1629 of FIG. 43. The physical anatomical model 1648 may be representative of a shoulder joint. The physical anatomical model 1648 may include one or more physical components 1648C. Each component 1648C may be representative of an associated component 1629C of the respective virtual anatomical model 1629. The components 1648C may include one or more bone volumes 1648B, such as bone volumes 1648B-1, 1648B-2. The bone volumes 1648B-1, 1648B-2 may be representative of the bone volumes 1629B-1, 1629B-2 of the virtual anatomical model 1629. The physical anatomical model 1648 may include one or more soft tissue volumes 1648S, which may be associated with the soft tissue volumes 1629S of the virtual anatomical model 1629. The physical anatomical model 1648 may be severable along an associated fracture path 1650 and/or fracture volume 1652. The fracture path 1650 and/or fracture volume 1652 may be associated with a respective fracture pattern 1647 (FIG. 43). The physical anatomical model 1648 may include one or more physical indicators 1656, including any of the indicators disclosed herein.

The physical anatomical model 1648 may be fixedly attached or otherwise secured to at least one physical fixture 1666 to establish an assembly 1668. The physical fixture 1666 may be associated with the virtual fixture 1686. In implementations, the virtual fixture 1686 may serve as a substrate for forming the physical anatomical model 1648 (see, e.g., substrate 1383 of FIG. 40).

The physical anatomical model 1648 may be severable along the fracture path 1650 and/or fracture volume 1652 to establish one or more fragments 1648F. The surgeon or clinical user may utilize an implant 1682 to secure the fragments 1648F. The surgeon or clinical user may utilize one or more fasteners (e.g., compression screws) 1686 to secure the fragments 1648F to each other and/or a main body 1648M of the physical anatomical model 1648.

Figure 45:
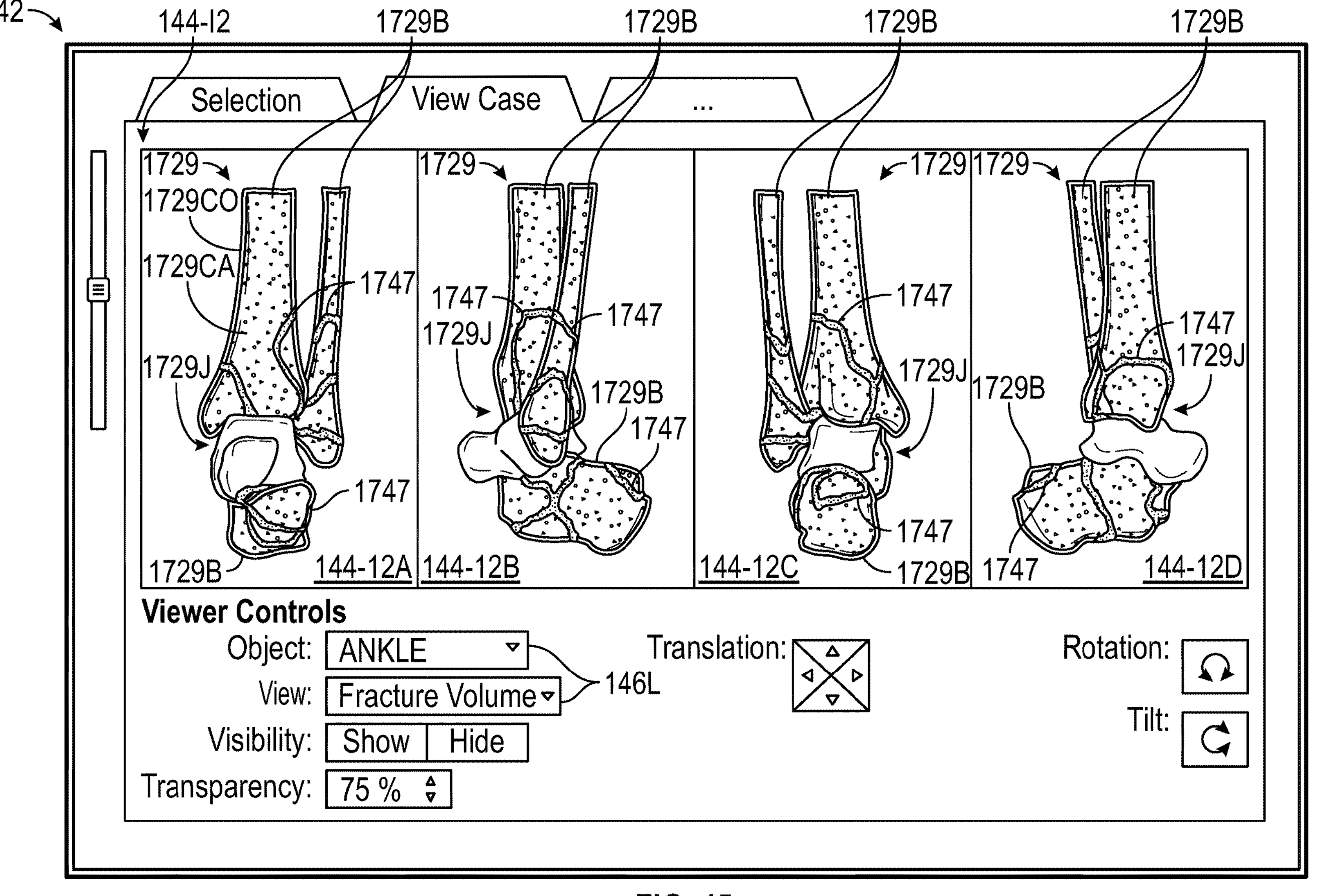
FIG. 45 discloses an implementation of a virtual anatomical model in the user interface of FIG. 2.

FIG. 45 discloses another implementation of a virtual anatomical model 1729. The virtual anatomical model 1729 may be representative of an ankle joint. The virtual anatomical model 1729 may be displayed in a display window 144-12 of the user interface 142 (FIG. 2). The virtual anatomical model 1729 may include one or more bone volumes 1729B that may cooperate to establish a joint 1629J. The joint 1629J may be associated with an ankle joint. The bone volumes 1729B may be associated with respective bones of an ankle joint (e.g., tibia, fibula, talus, calcaneus, etc.). One or more of the bone volumes 1729B may be associated with a respective fracture volume 1747.

Figures 46, 47A, 47B:
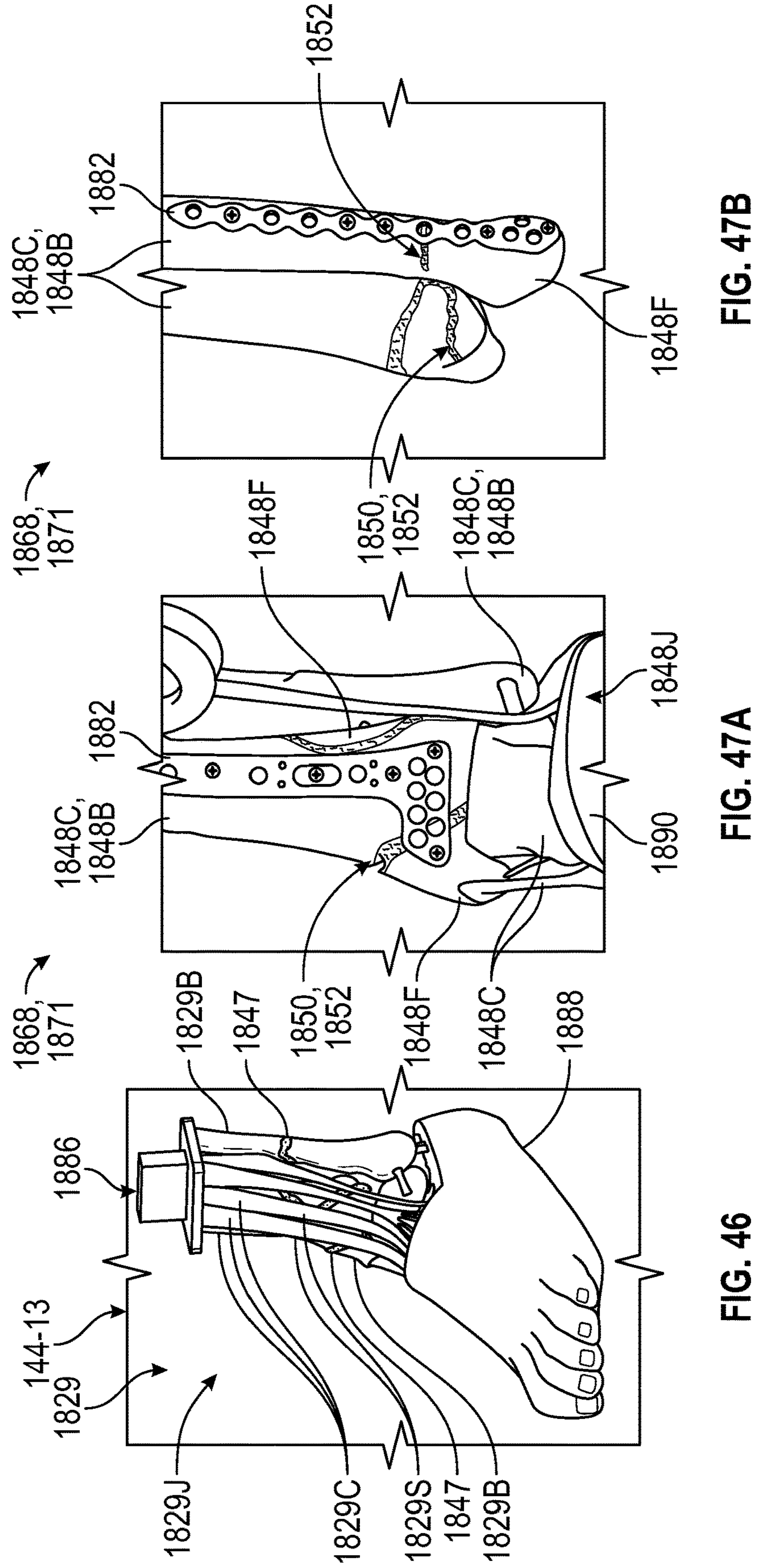
FIG. 46 discloses another implementation of a virtual anatomical model in a display window.
FIGS. 47A-47B disclose a physical anatomical model associated with the virtual anatomical model of FIG. 46.

FIG. 46 discloses another implementation of a virtual anatomical model 1829 in a display window 144-14 of the planning system 120. The virtual anatomical model 1829 may be representative of an extremity of a patient, such as a lower extremity including an ankle joint. The virtual anatomical model 1829 may be positioned relative to a virtual component 1888. The virtual component 1888 may be representative of anatomy and may be associated with a physical component 1890 (FIG. 47A). The virtual component 1888 may be generic or may be associated with a different patient than the virtual anatomical model 1829.

FIG. 47A discloses a physical anatomical model 1848. FIG. 47B discloses aspects of the physical anatomical model 1848 of FIG. 47B. The physical anatomical model 1848 may be associated with the virtual anatomical model 1829 of FIG. 46. The physical anatomical model 1848 may be representative of an extremity of a patient, such as a lower extremity including an ankle joint. The physical component 1890 (FIG. 47A) may be associated with the virtual component 1888. The physical component 1890 may be a reusable component and may have various constructions. In implementations, the physical component 1890 may be representative of anatomy such as a foot. One or more components of the physical anatomical model 1848 may be at least partially received in the physical component 1890. The surgeon or clinical user may utilize an implant 1882 to secure one or more fragments 1848F of the physical anatomical model 1848.

Figures 48, 49:
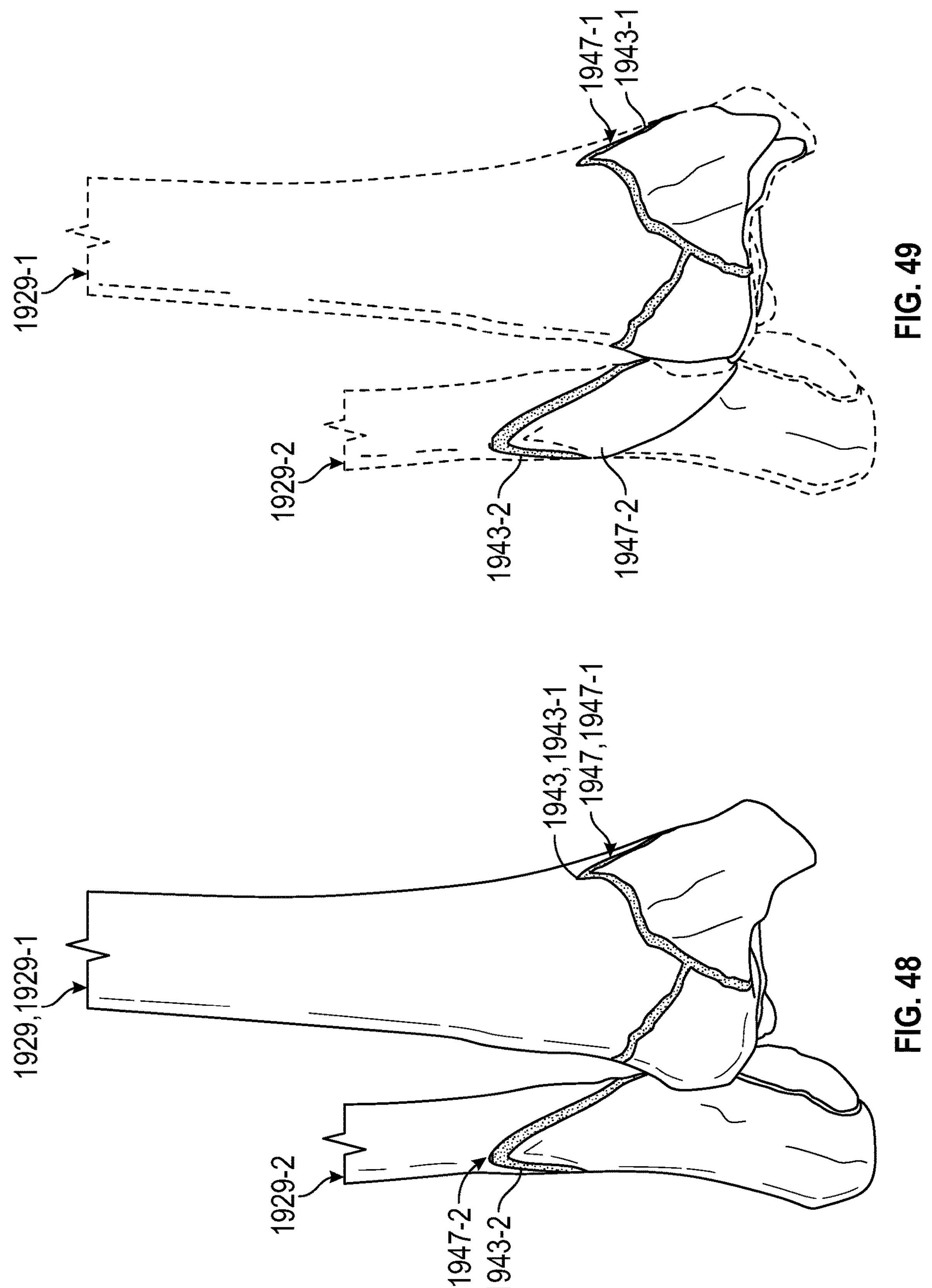
FIG. 48 discloses virtual anatomical models including respective fracture volumes according to an implementation.
FIG. 49 discloses the fracture volumes of FIG. 48 with the virtual anatomical models in phantom.

FIGS. 48-49 disclose virtual anatomical models 1929 according to an implementation. The anatomical models 1929 may include a first anatomical model 1929-1 and a second anatomical model 1929-2, which may be adjacent to the first anatomical model 1929-1. FIG. 49 depicts the anatomical models 1929 in phantom. The anatomical models 1929 may incorporate any of the features disclosed herein, including anatomical features representative of anatomy, such as one or more bones including cartilage, cortical and/or cancellous bone tissue, soft tissue including muscle, ligaments and/or tendons, etc., and/or other tissue. Each anatomical model 1929 may be associated with a surgical plan (e.g., surgical plan 131 of FIG. 2). In implementations, the anatomical models 1929 may be associated with respective bones of a limb of a patient. The bones may be adjacent to each other. The anatomical model 1929-1 may include portions associated with a joint of a patient, including any of the joints disclosed herein such as an ankle joint. The anatomical model 1929-1 may be associated with a tibia of a patient. The anatomical model 1929-2 may be associated with a fibula of the patient.

The anatomical models 1929-1, 1929-2 may be associated with respective virtual fracture volumes 1947 (indicated by 1947-1, 1947-2). Each fracture volume 1947-1, 1947-2 may be established by a respective fracture pattern 1943 (indicated by 1943-1, 1943-2). The fracture pattern 1943 may be established utilizing any of the techniques disclosed herein. The fracture pattern 1943 and associated fracture volume 1947 may be established based on an associated fracture classification scheme 141 (FIG. 2). In implementations, the fracture pattern 1943 may be dimensioned to substantially follow an outer periphery of the respective anatomical model 1929. The outer periphery may be associated with an inner cortical wall or an outer cortical wall of a bone. The fracture volume 1947 may be dimensioned to span between opposite sides of a perimeter of the fracture pattern 1943 such that the fracture volume 1947 may extend substantially through a main body of the virtual anatomical model 1929.

A portion of the virtual fracture volume 1947 may be established by extruding a shape along a length of the perimeter of the fracture pattern 1943. The fracture volume 1947 may include a portion (e.g., area) within a periphery of the fracture pattern 1943 such that the fracture volume 1947 may have a contiguous (e.g., enclosed) three-dimensional profile. The fracture volume 1947 may have various geometries, such as a substantially planar or complex geometry. In the implementation of FIG. 49, each of the fracture volumes 1947 has a contoured geometry associated with a profile of the fracture pattern 1943. FIG. 50 discloses the fracture volumes 1947-1, 1947-2 at the orientation of FIGS. 48-49. FIG. 51 discloses the fracture volumes 1947-1, 1947-2 at a different orientation.

Various techniques may be utilized to establish a geometry of the portion of the fracture volume 1947 inside of the perimeter of the fracture pattern 1943, such as manual sculpting or automated techniques. Automated techniques may include a "close holes" operation in which an interior of an object is filled by a two-dimensional or three-dimensional mesh. The spatial module 137 (FIG. 2) may be configured to generate the fracture pattern 1943 and associated fracture volume 1947 utilizing any of the techniques disclosed herein.

FIG. 52 discloses a sectional view of the virtual anatomical model 1929-1 and the respective fracture volume 1947-1. In the implementation of FIG. 52, the fracture volume 1947-1 may extend completely, or at least substantially, through a volume of the anatomical model 1929-1. The fracture volume 1947-1 may be established in the anatomical model 1929-1 to facilitate at least partial or complete separation of adjacent portions of an associated physical anatomical model. The virtual anatomical model 1929 may be utilized to establish a physical anatomical model utilizing any of the techniques disclosed herein. The anatomical model 1929 and fracture volume 1947 may be associated with the same and/or different structures, materials, porosities, etc., including any of those disclosed herein, for establishing the physical anatomical model. A configuration 145 (FIG. 2) for fabrication the physical anatomical model may specify a geometry associated with the fracture volumes 1947-1, 1947-2 for establishing a physical fracture path (e.g., pattern) and associated fracture volume in the physical anatomical model.

Figures 53, 54, 55:
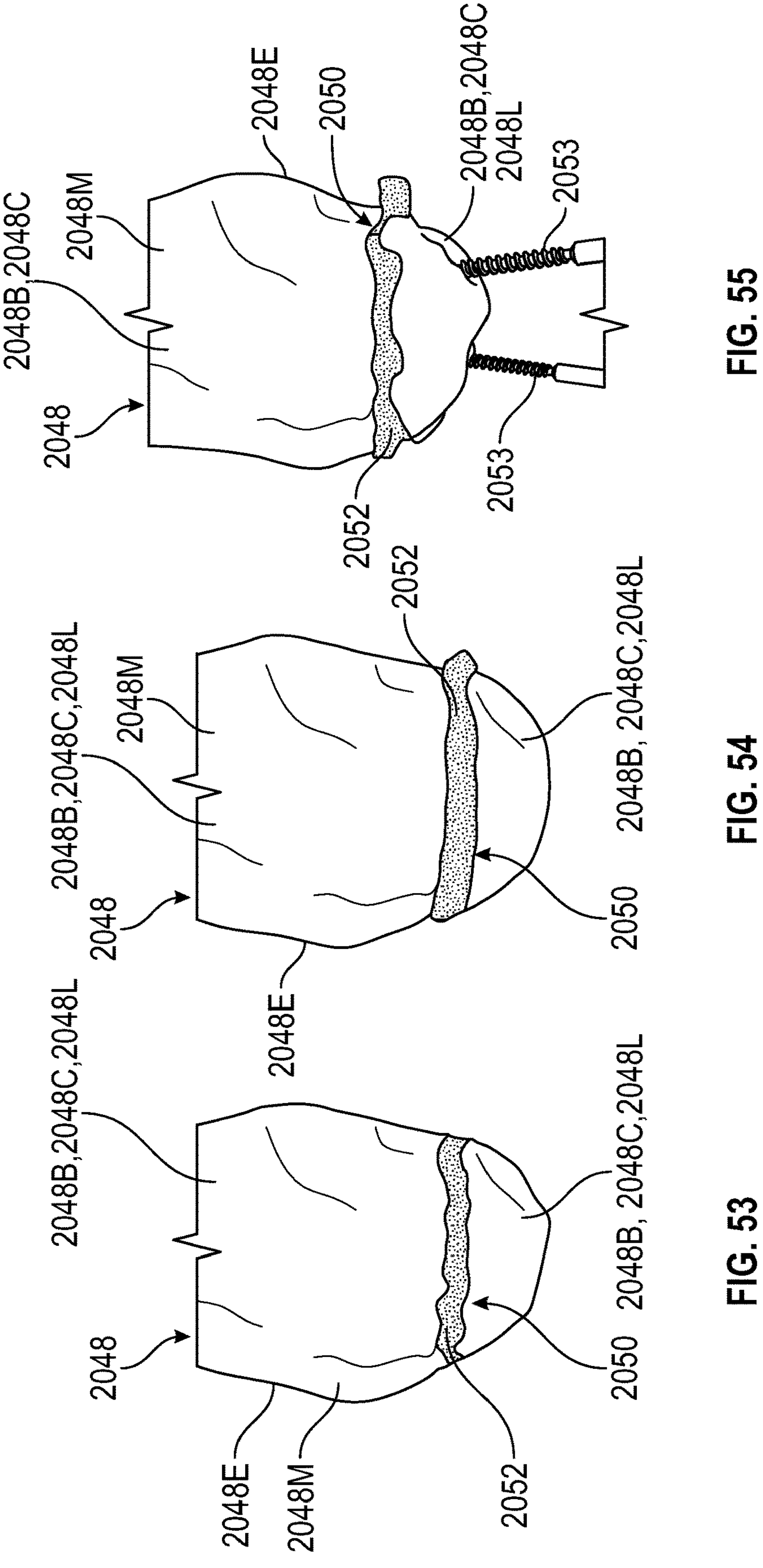
FIGS. 53-55 disclose various states of a physical anatomical model including a fracture path.

FIGS. 53-55 disclose various states of a physical anatomical model 2048 including a fracture path (e.g., pattern) 2050. The physical anatomical model 2048 may be formed utilizing any of the techniques disclosed herein.

The physical anatomical model 2048 may include a main body 2048M. The main body 2048M may include an external surface 2048E associated with an anatomical profile of a bone, including any of the bones disclosed herein. The physical anatomical model 2048 may include one or more physical components 2048C. Each component 2048C may be representative of an associated component of the respective virtual anatomical model 129 (FIG. 2). The components 2048C of the physical anatomical model 2048 may include any of the components disclosed herein, such as respective bone volumes 2048B.

The fracture path 2050 may be established according to an assigned virtual fracture pattern and/or virtual fracture volume, such as the virtual fracture pattern 1943 and/or virtual fracture volume 1947 of FIGS. 48-49. The main body 2048M of the physical anatomical model 2048 may include at least one, or more than one, physical fracture volume 2052. The physical fracture volume 2052 may be established along the fracture path 2050. The physical fracture volume 2052 may extend completely, or at least substantially, through a volume of the main body 2048M to facilitate partial and/or complete separation. The fracture volume 2052 may span between opposite sides of a perimeter of the fracture path 2050 to extend completely, or at least substantially, through the main body 2048M of the physical anatomical model 2048.

The physical fracture volume 2052 may establish one or more localized regions 2048L of the physical anatomical model 2048. The fracture volume 2052 may be adapted to divide the main body 2048M into two or more localized regions 2048L associated with the respective components 2048C. The physical fracture volume 2052 may establish frangible connection(s) between the localized regions 2048L and each other and/or the main body 2048M of the physical anatomical model 2048. The main body 2048M may be severable along the fracture volume 2052 to establish one or more fragments.

The physical anatomical model 2048 including the main body 2048M and physical fracture volume 2052 may have various properties, which may include any of the properties disclosed herein. The properties of the main body 2048M and physical fracture volume 2052 may be the same or may differ from each other. The properties may include respective material strengths. The physical fracture volume 2052 may have a lesser material strength to promote fragmentation of the physical anatomical model 2048 in a reproducible manner. The fracture volume 2052 may incorporate any of the materials disclosed herein.

The physical fracture volume 2052 may include one or more indicators adapted to selectively communicate a state of the physical anatomical model 2048 in response to external force(s), such as a compressive, tensile, shear, bending and/or torsional forces. Various indicators may be utilized. The physical fracture volume 2052 may compressible or otherwise moveable to provide an indication, such as tactile feedback in response to compression by the surgeon. The fracture volume 2052 may incorporate a compressible material, such as an elastomer. The fracture volume 2052 may yield in response to relative movement between the adjacent components 2048C. The material characteristics may be selected such that the fracture volume 2052 may hold the adjacent components 2048C together subsequent to applying a force on the fracture volume 2052. The material characteristics may be selected to facilitate simulation of a semi-mobile, partial and/or complete break. The semi-mobile break may facilitate articulation between the resultant fragments.

FIG. 53 may be associated with a first state of the physical anatomical model 2048 prior to applying an external (e.g., compressive) force on the fracture volume 2052. FIG. 54 may be associated with a second state of the physical anatomical model 2048 in which an amount of compressive force is applied to the fracture volume 2052, causing the fracture volume 2052 to partially deform. The amount of compressive force may exceed a first (e.g., lower) preselected limit, which may cause the fracture volume 2052 to partially deform. The deformation may be non-permanent. Exceeding the first preselected limit may cause a portion of the fracture volume 2052 to bulge (e.g., FIG. 54). FIG. 55 may be associated with a third state of the physical anatomical model 2048 in which a different (e.g., greater) amount of compressive force may be applied to the fracture volume 2052. The amount of compressive force may exceed a second (e.g., upper) preselected limit, which may cause the fracture volume 2052 to permanently deform (e.g., separate). The preselected limit(s) may be established by various physical material characteristics of the fracture volume 2052. The external force(s) may be generated by a surgical device 2053. In implementations, the surgical device 2053 may be a fastener such as a compression screw, which may be utilized to attach the components 2048C to each other. The permanent deformation may provide an indication that the amount of compression exceeds the preselected limit.

Figure 56:
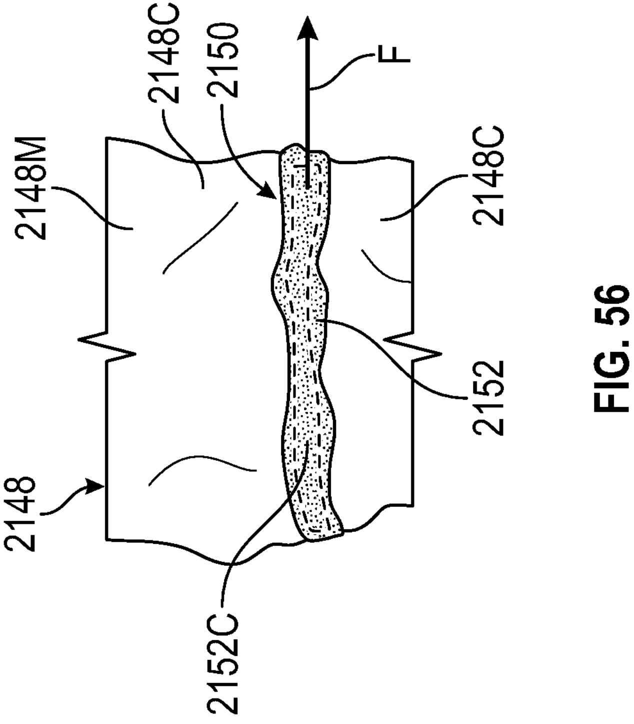
FIG. 56 discloses a physical anatomical model according to another implementation.

Other techniques may be utilized to provide an indication of an amount of external force applied to the physical fracture volume. In the implementation of FIG. 56, a physical anatomical model 2148 may include a fracture volume 2152 having at least one, or more than one, cavity (e.g., fluid reservoir) 2152C. The cavity 2152C may encapsulate or otherwise hold a fluid F. Applying a (e.g., compressive) force on the fracture volume 2152 that exceeds a (e.g., upper) preselected limit may cause the fracture volume 2052 to rupture to release a portion of the fluid F from the cavity 2151C. The rupture may provide an indication that the preselected limit has been exceeded.

Figure 57:
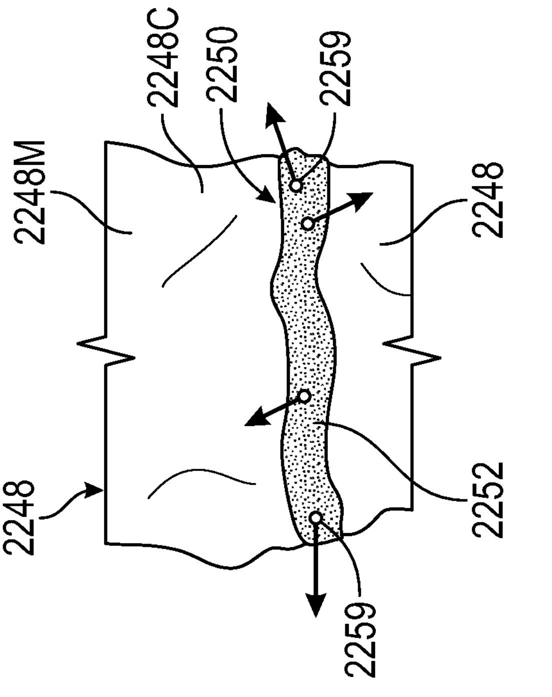
FIG. 57 discloses a physical anatomical model according to yet another implementation.

In the implementation of FIG. 57, a physical anatomical model 2248 may include a physical fracture volume 2252. One or more objects 2259 may be at least partially and/or completely embedded in the fracture volume 2252. The objects 2259 may have one or more physical characteristics that may differ from the material of the physical fracture volume 2252. In implementations, the objects 2259 may be granules having a generally spherical geometry. The granules may be relatively harder than the material of the fracture volume 2252. Applying a (e.g., compressive) force on the fracture volume 2252 that exceeds a (e.g., upper) preselected limit may cause the objects 2259 to release (e.g., eject) from the fracture volume 2252 to provide an indication that the preselected limit has been exceeded.

Figures 58, 59, 60:
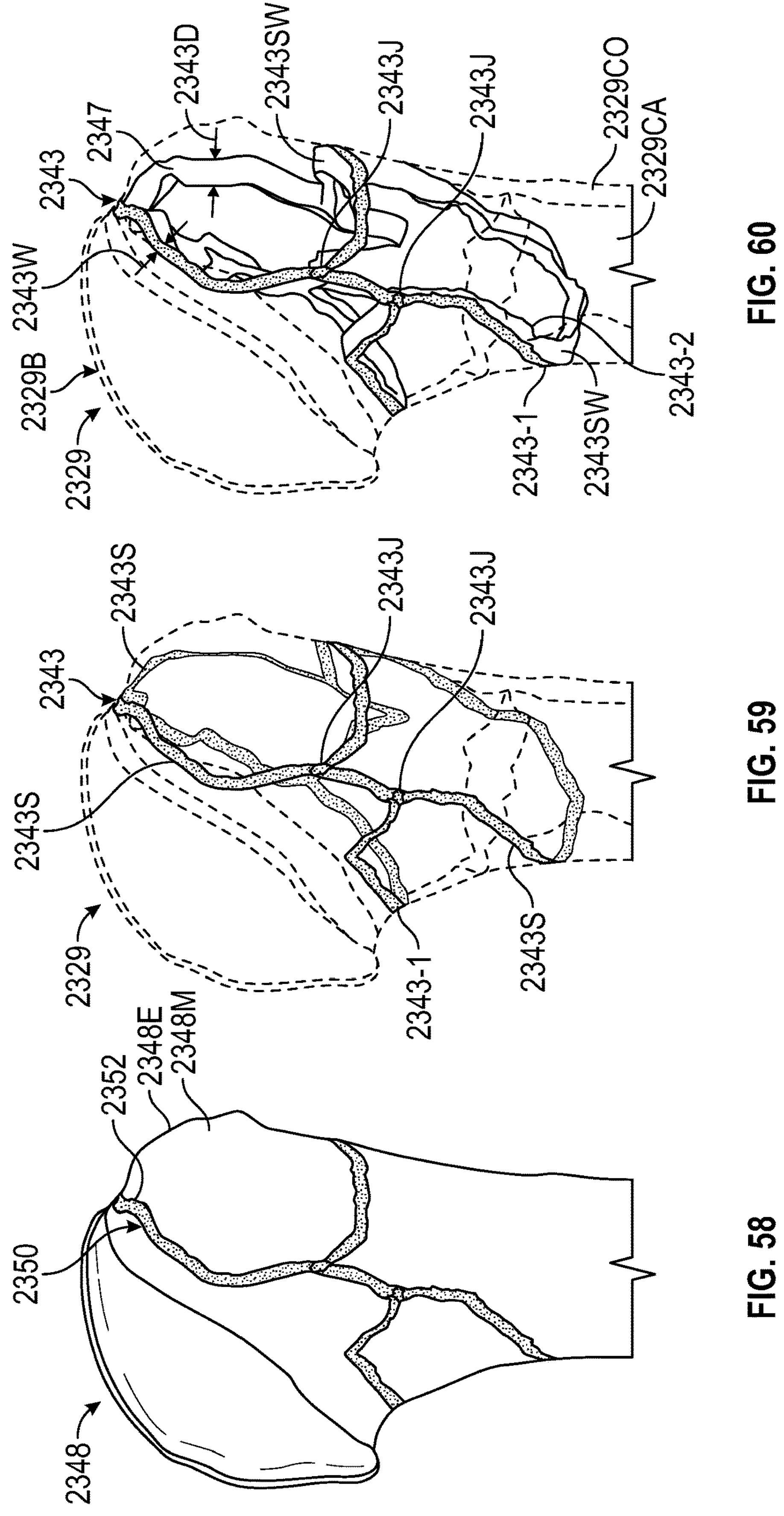
FIG. 58 discloses a physical anatomical model including a fracture volume according to another implementation.
FIG. 59 discloses a virtual anatomical model including a virtual fracture pattern.
FIG. 60 discloses the virtual anatomical model of FIG. 59 including a virtual fracture volume.

FIG. 58 discloses a physical anatomical model 2348 including a fracture path (e.g., pattern) 2350. The physical anatomical model 2348 may be formed utilizing any of the techniques disclosed herein. The physical anatomical model 2348 may include a main body 2348M. An external surface 2348E of the main body 2348M may be associated with an anatomical profile of a bone, including any of the bones disclosed herein such as a humerus. The fracture path 2350 may be established according to an assigned virtual fracture pattern and/or virtual fracture volume utilizing any of the techniques disclosed herein.

Referring to FIGS. 59-60, with continuing reference to FIG. 58, a virtual anatomical model 2329 according to an implementation is disclosed. The virtual anatomical model 2329 may be established utilizing any of the techniques disclosed herein. The virtual anatomical model 2329 may be associated with a virtual fracture pattern 2343 and/or virtual fracture volume 2347 (FIG. 60). In implementations, the fracture path 2350 (FIG. 58) may be established based on the virtual fracture pattern 2343 and/or virtual fracture volume 2347.

The virtual fracture pattern 2343 may include a first (e.g., outer) virtual fracture path 2343-1 and a second (e.g., inner) virtual fracture path 2343-2 (FIG. 60). The fracture paths 2343-1, 2343-2 may be spaced apart from each other. The virtual fracture volume 2347 may be bounded between the virtual fracture paths 2343-1, 2343-1.

The fracture paths 2343-1, 2343-2 may have various two-dimensional and/or three-dimensional geometries. Each of the fracture paths 2343-1, 2343-2 may include one or more undulations. Each of the fracture paths 2343-1, 2343-2 may include one or more segments 2343S. Each of the segments 2343S be a linear or non-linear path extending between two junctions 2343J. The outer and inner virtual fracture paths 2343-1, 2343-2 may be spaced apart from each other for an entirety, or at least majority, of their respective lengths. The outer fracture path 2343-1 may be dimensioned to substantially surround the inner fracture path 2343-2.

Various techniques may be utilized to establish the virtual fracture paths 2343-1, 2343-2. In implementations, the fracture paths 2343-1, 2343-2 may be established independently of each other. In other implementations, the inner fracture path 2343-2 may be established by a preselected offset distance 2343D from the outer fracture path 2343-1 (FIG. 60), or vice versa. The inner fracture path 2343-2 may be established by following the length of the outer fracture path 2343-1 at the preselected offset distance 2343D, or vice versa. The inner fracture path 2343-2 may have one or more segments 2343S offset from the outer fracture path 2343-1 by a distance 2343D' that may differ from the preselected offset distance 2343D (e.g., FIG. 63). Portions of the virtual fracture volume 2347 established by the distance 2343D' may be associated with a relatively weaker area than portions associated with the preselected offset distance 2343D, which may facilitate a reproducible break (e.g., fracture) in a targeted area of the physical anatomical model 2348.

Figure 63:
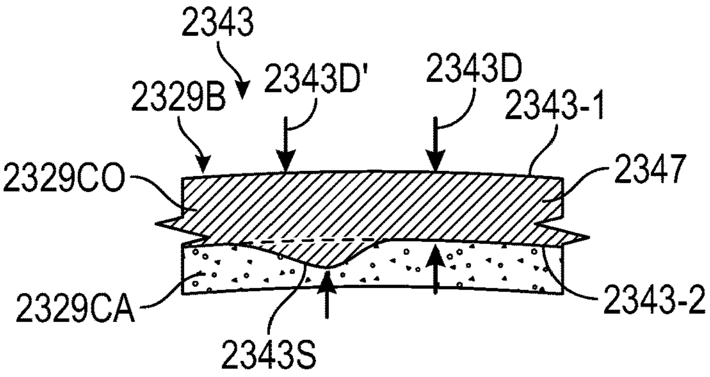
FIG. 63 discloses a sectional view of the virtual anatomical model and associated virtual fracture volume of FIG. 60.

The outer and inner virtual fracture paths 2343-1, 2343-2 may be established based on a profile of the virtual anatomical model 2329. The virtual fracture paths 2343-1, 2343-2 may be established relative to a bone volume 2343B, such as a cortical bone volume 2329CO and/or cancellous bone volume 2329CA (see, e.g., FIGS. 60 and 63). In implementations, the outer fracture path 2343-1 may be dimensioned to substantially follow a profile of the external wall of the bone volume 2343B, which may be associated with the cortical bone volume 2329CO. The inner fracture path 2343-2 may be dimensioned to substantially follow a profile of another portion of the virtual anatomical model 2329, such as an inner wall of the cortical bone volume 2329CO. The segment(s) 2343S of the inner fracture path 2343-2 may be established along the inner wall of the cortical bone volume 2329CO and/or at least partially in the cancellous bone volume 2329CA. In the implementation of FIG. 63, segment(s) 2343S of the inner fracture path 2343-2 may be spaced apart from (e.g., inward of) the inner wall of the cortical bone volume 2329CO.

Figure 61:
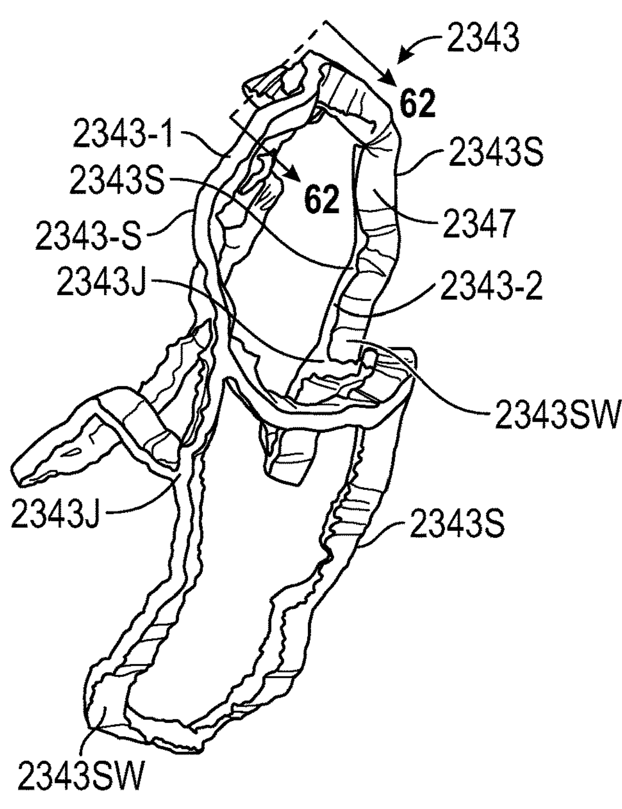
FIG. 61 discloses an isolated view of the virtual fracture volume of FIG. 60.
Figure 62:
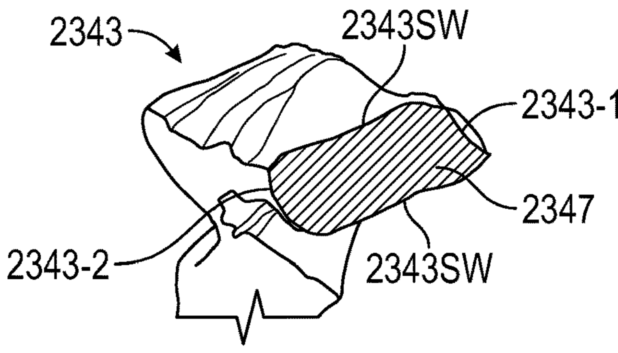
FIG. 62 discloses a sectional view of the virtual fracture volume of FIG. 60.

Referring to FIGS. 61-62, with continuing reference to FIGS. 59-60, each fracture path 2343-1, 2343-2 of the virtual fracture pattern 2343 may have a generally ribbon-shaped geometry. Each fracture path 2343-1, 2343-2 may have a width 2343W (FIG. 60) along its respective length. The width 2343W of each fracture path 2343-1, 2343-2 may be substantially constant or may differ along the respective length. Sidewalls 2343SW may be established between adjacent sides of the fracture paths 2343-1, 2343-2 to bound the virtual fracture volume 2347. In implementations, the sidewalls 2343SW may be established by one or more facets between the adjacent sides of the fracture paths 2343-1, 2343-2.

The virtual fracture volume 2347 may be assigned one or more characteristics that may be the same or may differ from adjacent portions of the virtual anatomical model 2329, including any of the characteristics disclosed herein such as the various material characteristics. In implementations, the virtual fracture volume 2347 may be associated with a relatively weaker material than a material associated with adjacent portion(s) of the virtual anatomical model 2329, such as the cortical bone volume 2329CO associated with cortical bone and/or the cancellous bone volume 2329CA associated with cancellous bone.

The novel devices and methods of this disclosure provide versatility in planning, rehearsing and training for surgical procedures utilizing physical anatomical models. The physical anatomical models may be representative of various anatomy, including anatomy associated with various fracture classifications. The surgeon may interact with the disclosed system to gain familiarity with the selected anatomy and various surgical procedures that may be utilized to implement a surgical plan, including the repair of fractures that may be associated with different fracture classifications. The physical anatomical models may be representative of various tissue types and may incorporate one or more indicators to facilitate training. The indicators may assist the surgeon in determining the accuracy of implementing surgical procedures on the physical anatomical model.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

It should be understood that like reference numerals identify corresponding or similar elements throughout the several drawings. It should further be understood that although a particular component arrangement is disclosed and illustrated in these exemplary embodiments, other arrangements could also benefit from the teachings of this disclosure.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A physical anatomical model comprising:

a main body including an external surface associated with an anatomical profile of a bone, and the main body including a fracture path that establishes one or more localized regions;

wherein the main body includes a first volume and a fracture volume comprising material, the fracture volume is established along the fracture path such that the fracture volume is at least partially embedded in the first volume, and the fracture volume is weaker than the first volume to establish a frangible connection between adjacent portions of the main body; and wherein the main body is severable along the fracture path and the associated fracture volume to establish one or more fragments associated with the one or more localized regions.

2. The physical anatomical model as recited in claim 1, wherein the fracture path includes one or more segments, and each of the one or more segments establishes a loop about the respective localized region.

3. The physical anatomical model as recited in claim 1, wherein the fracture path is established according to a predetermined fracture pattern.

4. The physical anatomical model as recited in claim 1, wherein:

the main body includes a second volume;

the first volume establishes the external surface of the main body and is representative of cortical bone; and the second volume is representative of cancellous bone.

5. The physical anatomical model as recited in claim 4, wherein:

the fracture path and the associated fracture volume extend along a boundary region between the first volume and the second volume.

6. The physical anatomical model as recited in claim 5, wherein the first volume has a first property, and the fracture volume has a second property that differs from the first property.

7. The physical anatomical model as recited in claim 6, wherein the first property includes a first material strength, and the second property includes a second material strength that is less than the first material strength.

8. The physical anatomical model as recited in claim 1, wherein:

the main body includes one or more indicators associated with the fracture path.

9. The physical anatomical model as recited in claim 1, wherein:

the fracture volume extends substantially through the main body such that the main body is severable along the fracture volume to establish the one or more fragments.

10. The physical anatomical model as recited in claim 9, wherein the fracture volume includes at least one indicator adapted to selectively communicate a state of the physical anatomical model in response to an external force.

11. The physical anatomical model as recited in claim 10, wherein the fracture volume includes a compressible material.

12. The physical anatomical model as recited in claim 1, wherein:

the first volume has a first property including a first material strength, and the fracture volume has a second property including a second material strength that is less than the first material strength.

13. An orthopaedic system comprising:

a physical anatomical model including a main body having a fracture path, wherein the main body includes a first volume and a fracture volume comprising material, the fracture volume is established along the fracture path such that the fracture volume is at least partially embedded in the first volume, and the fracture volume is weaker than the first volume to establish a frangible connection between adjacent portions of the main body; and a fracture tool adapted to cause the main body to sever along the fracture path and the associated fracture volume to establish one or more fragments.

14. The orthopaedic system as recited in claim 13, wherein:

the main body includes a second volume;

the first volume establishes an external surface of the main body and is representative of cortical bone; and the second volume is representative of cancellous bone.

15. The orthopaedic system as recited in claim 13, wherein:

the fracture tool includes a clamp having a first clamp element and a second clamp element;

the first clamp element includes a plurality of configurable engagement elements dimensioned to engage selectable contact points along the main body; and each of the engagement elements is adapted to cooperate with the second clamp element to apply a compressive force at the respective contact point to cause the main body to sever along the fracture path and the associated fracture volume to establish the one or more fragments.

16. A system for rehearsing a surgical procedure comprising:

a computing device including one or more processors coupled to memory; and an additive manufacturing device;

wherein the one or more processors are configured to execute a surgical environment, and the surgical environment is configured to:

access a virtual anatomical model from the memory, the virtual anatomical model associated with an anatomy;

cause the virtual anatomical model to be displayed in a graphical user interface;

assign a fracture pattern to the virtual anatomical model based on one or more parameters;

establish a fracture path based on the assigned fracture pattern;

establish a fracture volume that follows the fracture path, wherein the virtual anatomical model includes a main body having a first volume and the fracture volume at least partially embedded in the first volume, and the fracture volume is weaker than the first volume to establish a frangible connection between adjacent portions of the main body;

generate a configuration associated with a physical anatomical model representative of the virtual anatomical model; and communicate the configuration to the additive manufacturing device, wherein the additive manufacturing device is operable to form the physical anatomical model according to the configuration such that the physical anatomical model is severable along the fracture path and the associated fracture volume to establish one or more fragments.

17. The system as recited in claim 16, wherein:

the one or more parameters are associated with a predefined fracture classification scheme; and the surgical environment is configured to assign the fracture pattern to the virtual anatomical model in response to setting the one or more parameters associated with the predefined fracture classification scheme.

18. The system as recited in claim 16, wherein:

the virtual anatomical model includes a second volume;

the first volume is representative of cortical bone; and the second volume is representative of cancellous bone.

19. The system as recited in claim 16, wherein:

the fracture volume extends substantially through the main body.

20. The system as recited in claim 16, wherein:

the additive manufacturing device includes a three-dimensional printer.

* * * * *